US012680085B2

(12) United States Patent
Poon et al.

(10) Patent No.: US 12,680,085 B2
(45) Date of Patent: Jul. 14, 2026

(54) RECOMBINANT VIRUSES EXPRESSING ALPHA-1, 3-GALACTOSYLTRANSFERASE AND USES THEREOF

(71) Applicant: The University of Hong Kong, Hong Kong (CN)

(72) Inventors: Lit Man Poon, Hong Kong (CN); Li-Meng Yan, Hong Kong (CN); Pui Ngan Lau, Hong Kong (CN); Malik Peiris, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 982 days.

(21) Appl. No.: 17/791,678

(22) PCT Filed: Jan. 11, 2021

(86) PCT No.: PCT/CN2021/071079
§ 371 (c)(1),
(2) Date: Jul. 8, 2022

(87) PCT Pub. No.: WO2021/139810
PCT Pub. Date: Jul. 15, 2021

(65) Prior Publication Data
US 2023/0295581 A1 Sep. 21, 2023

Related U.S. Application Data

(60) Provisional application No. 62/959,581, filed on Jan. 10, 2020.

(51) Int. Cl.
*C12N 7/00* (2006.01)
*A61P 31/16* (2006.01)
(Continued)

(52) U.S. Cl.
CPC ............... *C12N 7/00* (2013.01); *A61P 31/16* (2018.01); *C12N 9/1051* (2013.01);
(Continued)

(58) Field of Classification Search
None
See application file for complete search history.

(56) References Cited

FOREIGN PATENT DOCUMENTS

CN       1756568 A       4/2006
CN       107787364 A     3/2018
WO    WO-2019081750 A1 *  5/2019  ............. A61K 39/12

OTHER PUBLICATIONS

Kotomina et al. (Human Vaccines and Immunotherapeutics. 14 (12); 2964-2970).*

(Continued)

*Primary Examiner* — Shanon A. Foley
(74) *Attorney, Agent, or Firm* — Pabst Patent Group LLP

(57) ABSTRACT

Disclosed are viruses, and vaccines comprised of and made from such viruses, that include a heterologous nucleic acid segment encoding α-1,3-galactosyltransferase (α-1,3-GT) such that the nucleic acid segment expresses α-1,3-GT when the virus infects a host cell. Such viruses produce proteins having α-1,3-galactose. The presence of α-1,3-galactose on proteins of infected cells can powerfully stimulate the immune response of the host against the viral proteins of the virus, thus enhancing the effect of the virus as a vaccine. Also disclosed are vaccines that include and/or are produced by such viruses. Also disclosed are methods of making and using such viruses and vaccines, such as administering to a subject in need thereof a vaccine as disclosed and such as making a vaccine that includes one or more viral proteins expressed by a virus as disclosed.

21 Claims, 22 Drawing Sheets

(51) Int. Cl.
    *C12N 9/10*       (2006.01)
    *A61K 39/00*     (2006.01)
(52) U.S. Cl.
    CPC ................. *A61K 2039/5254* (2013.01); *A61K 2039/5256* (2013.01); *A61K 2039/575* (2013.01); *C12Y 204/01087* (2013.01); *C12Y 302/01018* (2013.01)

(56) References Cited

OTHER PUBLICATIONS

Henion et al. (Vaccine. 1997; 15 (11): 1174-1182).*
Mandell et al. (Zoonoses and public health. Aug. 2009; 56 (6-7): 391-406).*
Chen et al. (PLoS One. Aug. 7, 2017; 12 (8): e0182683).*
Chng et al. (InMAbs Mar. 4, 2015; 7 (2): 403-412).*
Lantéri et al. (Glycobiology. Jan. 1, 2002 ;12 (12): 785-92).*
Liu et al. (Vaccine. 2009; 27: 6460-6463).*
Furusawa et al. (MBio. Oct. 29, 2019; 10 (5): 10-128).*
Henion et al. (Glycobiology. 1994; 4 (2): 193-201).*
Abdel-Motal, et al., "Increased immunogenicity of HIV-1 p24 and gp120 following immunization with gp120/p24 fusion protein vaccine expressing alpha-gal epitopes", Vaccine, 28:1758-1765 (2010).
Albertini, et al., "Phase I study to evaluate toxicity and feasibility of intratumoral injection of α-gal glycolipids in patients with advanced melanoma", Cancer Immunol. Immunother., 65:897-907 (2016).
Badgett et al., "Evolutionary dynamics of viral attenuation", J. Virol., 76:10524-10529 (2002).
Baker, et al., "Downregulating viral gene expression: codon usage bias manipulation for the generation of novel influenza A virus vaccines", Future Virol., 10(6):715-30 (2015).
Boudreau and Alter, "Extra-Neutralizing FcR-Mediated Antibody Functions for a Universal Influenza Vaccine", Front. Immunol., 10:440 (2019).
Condon, et al., J. Leukoc. "Lung dendritic cells at the innate-adaptive immune interface", Biol., 90:883-95 (2011).
Desch, et al., "CD103+ pulmonary dendritic cells preferentially acquire and present apoptotic cell-associated antigen", J. Exp. Med., 208:1789-1797 (2011).
Desch, et al., "Pulmonary dendritic cell development and antigen acquisition", Immunologic Research, 55:178-186 (2013).
Eisenbarth, "Dendritic cell subsets in T cell programming: location dictates function", Nat. Rev. Immunol., 19:89-103 (2019).
Fan, et al., "Generation of Live Attenuated Influenza Virus by Using Codon Usage Bias", J. Virol., 89:10762-73 (2015).
Furuhashi, et al., "Mouse lung CD103+ and CD11bhigh dendritic cells preferentially induce distinct CD4+ T-cell responses", Am. J. Respir. Cell Mol. Biol., 46:165-72 (2012).
Galili, "Anti-Gal: an abundant human natural antibody of multiple pathogeneses and clinical benefits", Immunology, 140:1-11 (2013).
Geurtsvankessel, et al., "Clearance of influenza virus from the lung depends on migratory langerin +CD11b– but not plasmacytoid dendritic cells", J. Exp. Med., 205:1621-34 (2008).
Guilliams, et al., "The function of Fcγ receptors in dendritic cells and macrophages", Nat. Rev. Immunol., 14: 94-108 (2014).
Heath and Carbone, "Dendritic cell subsets in primary and secondary T cell responses at body surfaces", Nat. Immunol., 10:1237 (2009).
Helft, et al., "Cross-presenting CD103+ dendritic cells are protected from influenza virus infection", J. Clin. Invest., 122:4037-47 (2012).
Henion, et al., "Synthesis of alpha-gal epitopes on influenza virus vaccines, by recombinant alpha 1,3galactosyltransferase, enables the formation of immune complexes with the natural anti-Gal antibody", Vaccine, 15: 1174-82 (1997).
Hoffmann et al., "A simple and fast system for cloning influenza A virus gene segments into pHW2000- and pCAGGS-based vectors", Proc. Natl. Acad. Sci. USA, 97:6108-6113 (2000).

Horton, et al., "Optimization and validation of an 8-color intracellular cytokine staining (ICS) assay to quantify antigen-specific T cells induced by vaccination", J. Immunol. Methods, 323:39-54 (2007).
Jegaskanda, et al., "Cross-reactive influenza-specific antibody-dependent cellular cytotoxicity antibodies in the absence of neutralizing antibodies", J. Immunol., 190:1837-1848 (2013).
Kim, et al., "Distinct dendritic cell subsets dictate the fate decision between effector and memory CD8(+) T cell differentiation by a CD24-dependent mechanism", Immunity, 40:400-13 (2014).
Kim, et al., "High cleavage efficiency of a 2A peptide derived from porcine teschovirus-1 in human cell lines, zebrafish and mice", PLoS One, 6:e18556 (2011).
Krammer, et al., "Influenza", Nat. Rev. Dis. Primers, 4:3 (2018).
LaTemple and Galili, "Adult and neonatal anti-Gal response in knock-out mice for alpha1,3galactosyltransferase", Xenotransplantation, 5:191-196 (1998).
Lehmann, et al., "DC subset-specific induction of T cell responses upon antigen uptake via Fcγ receptors in vivo", J. Exp. Med., 214:1509-1528 (2017).
Leung, et al., "Entry of influenza A Virus with a γ2,6-linked sialic acid binding preference requires host fibronectin", J. Virol., 86:10704-13 (2012).
Liu, B., et al., "Characterization of tectoRNA assembly with cationic conjugated polymers", J. Am. Chem. Soc., 126:4076-4077 (2004).
Loudon et al., "Preclinical safety testing of DISC-hGMCSF to support phase I clinical trials in cancer patients", J Gene Med., 3:458-467 (2001).
Manches, et al., "Anti-Gal-mediated targeting of human B lymphoma cells to antigen-presenting cells: a potential method for immunotherapy using autologous tumor cells", Haematologica, 90:625-34 (2005).
Merad, et al., "The dendritic cell lineage: ontogeny and function of dendritic cells and their subsets in the steady state and the inflamed setting", Annual Rev. Immunol., 31:563-604 (2013).
Mesnil, et al., "Resident CD11b(+)Ly6C(–) lung dendritic cells are responsible for allergic airway sensitization to house dust mite in mice", PLoS One, 7:e53242 (2012).
Misharin, et al., "Flow cytometric analysis of macrophages and dendritic cell subsets in the mouse lung", Am. J. Respir. Cell Mol. Biol., 49:503-10 (2013).
Paules, et al., "Chasing Seasonal Influenza—The Need for a Universal Influenza Vaccine", N. Engl. J. Med., 378:7-9 (2018).
Pfeiffer and Kirkegaard, "Increased fidelity reduces poliovirus fitness and virulence under selective pressure in mice", PLoS Pathog., 1:e11 (2005).
Plantinga, et al., "Conventional and monocyte-derived CD11b(+) dendritic cells initiate and maintain T helper 2 cell-mediated immunity to house dust mite allergen", Immunity, 38:322-335 (2013).
Rajao and Perez, "Universal Vaccines and Vaccine Platforms to Protect against Influenza Viruses in Humans and Agriculture", Front. Microbiol., 9:123 (2018).
Richards, et al., "Infection of HLA-DR1 transgenic mice with a human isolate of influenza a virus (H1N1) primes a diverse CD4 T-cell repertoire that includes CD4 T cells with heterosubtypic cross-reactivity to avian (H5N1) influenza virus", J. Virol., 83:6566-6577 (2009).
Tam, et al., "Intranasal influenza vaccine: Why does Canada have different recommendations from the USA on its use?", Paediatr. Child Health, 23:31-34 (2018).
Tearle, et al., "The alpha-1,3-galactosyltransferase knockout mouse. Implications for xenotransplantation" Transplantation, 61:13-9 (1996).
Ueki, et al., "In vivo imaging of the pathophysiological changes and neutrophil dynamics in influenza virus-infected mouse lungs", PNAS, 115:E6622-E6629 (2018).
Valkenburg et al., "IL-15 adjuvanted multivalent vaccinia-based universal influenza vaccine requires CD4+ T cells for heterosubtypic protection," Proc. Natl. Acad. Sci. USA, 111:5676-81 (2014).
Valkenburg et al., "Protection by universal influenza vaccine is mediated by memory CD4 T cells", Vaccine, 36:4198-4206 (2018).
Vignuzzi et al., "Quasispecies diversity determines pathogenesis through cooperative interactions in a viral population", Nature, 439:344-348 (2006).

(56)
References Cited

OTHER PUBLICATIONS

World Health Organization, website who. int/csr/disease/swineflu/assess/disease_swineflu_assess_20090511/en/; Accessed in Jul. 2019.

Wu, et al., "The infection attack rate and severity of 2009 pandemic H1N1 influenza in Hong Kong", Clin. Infect. Dis., 51:1184-91 (2010).

Yan, et al., "Combined use of live-attenuated and inactivated influenza vaccines to enhance heterosubtypic protection", Virology, 525:73-82 (2018).

Zhou, et al., "In Vitro Packaging of Adeno-Associated Virus DNA", J. Virol., 72(4):3241-7 (1998).

International Search Report received for PCT Application No. PCT/CN2021/071079, mailed on Apr. 15, 2021, 6 pages.

Huai, et al., "Characteristics of $\alpha$-Gal Epitope, Anti-Gal Antibody, $\alpha 1,3$ galactosyltransferase and its Clinical Exploitation (Review)", International Journal of Molecular Medicine, vol. 37, 2016, pp. 11-20.

Yan, et al., "Heterosubtypic Protection Induced by a Live Attenuated Influenza Virus Vaccine Expressing Galactose-$\alpha$-1,3-Galactose Epitopes in Infected Cells", American Society for Microbiology, mBio, vol. 11, No. 2, Mar. 3, 2020, pp. 1-17.

* cited by examiner

NAGT with Serum      NAGT without Serum 29.6%             55.7%

FSC-A

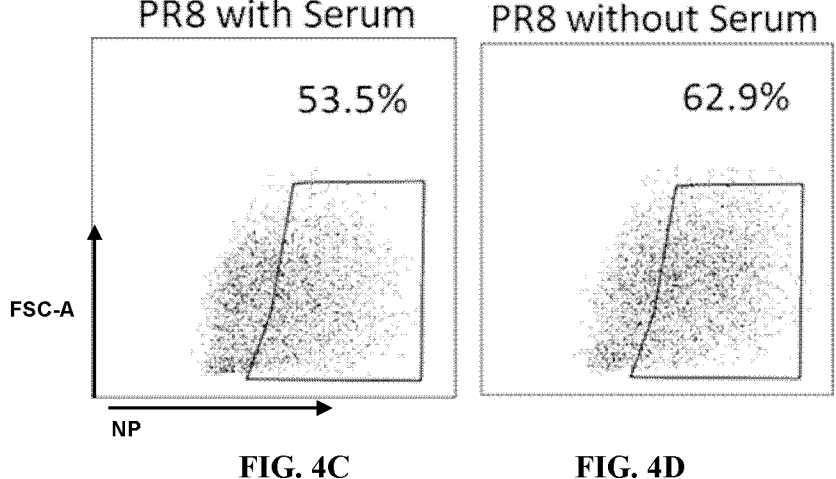
FIG. 4C                          FIG. 4D
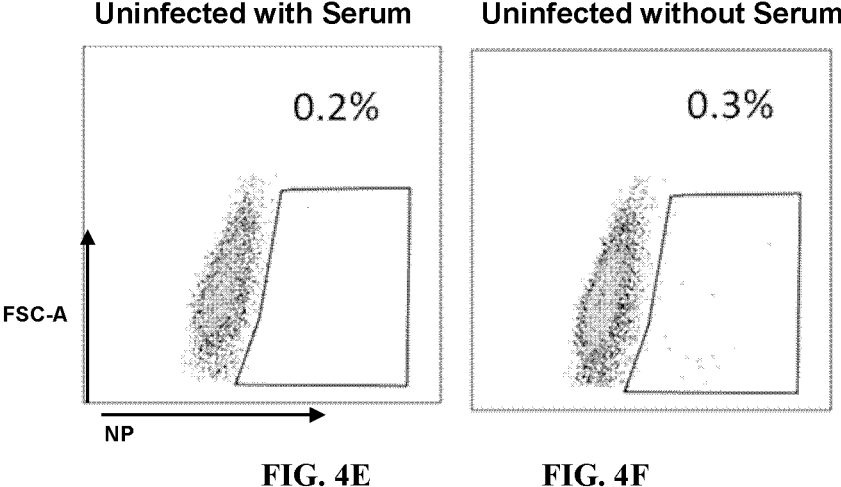
FIG. 4E                          FIG. 4F

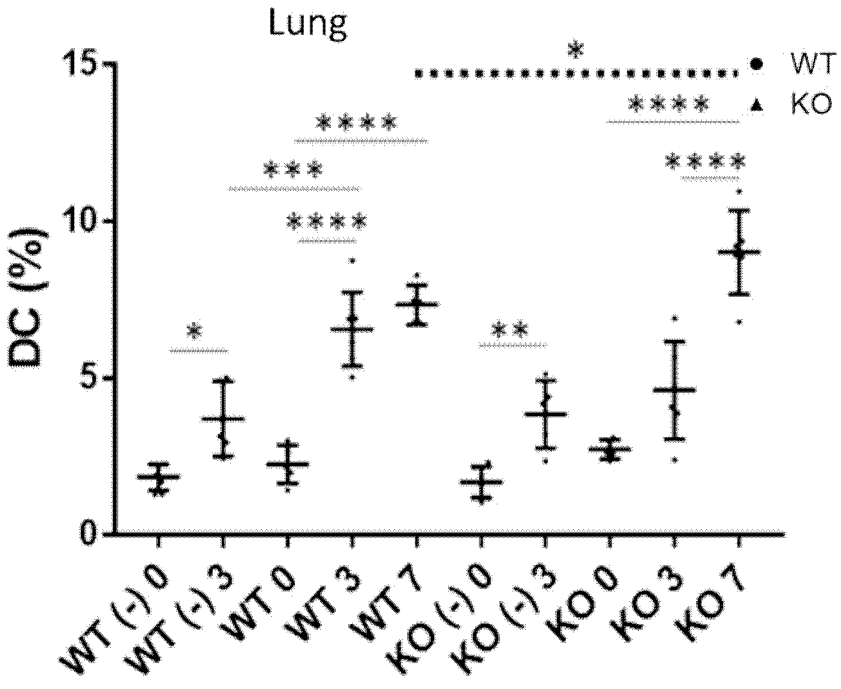
FIG. 18A
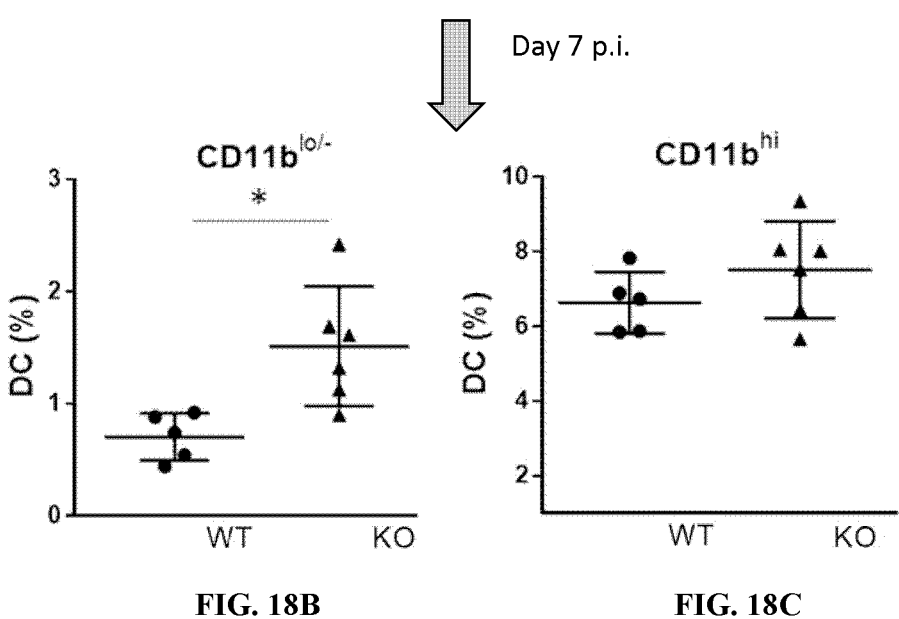
FIG. 18B     FIG. 18C

H3N2/HK68

RECOMBINANT VIRUSES EXPRESSING ALPHA-1, 3-GALACTOSYLTRANSFERASE AND USES THEREOF

This application is a National Phase application under 35 U.S.C. 371 of PCT/CN2021/071079, filed Jan. 11, 2021, which claims the benefit of the filing date of U.S. Provisional Patent Application No. 62/959,581 filed on Jan. 10, 2020, the entire content of which is incorporated by reference for all purpose.

FIELD OF THE INVENTION

The disclosed invention is generally in the field of vaccines and specifically in the area of live attenuated vaccines.

BACKGROUND OF THE INVENTION

Influenza is a highly contagious disease associated with a major impact on global public health (Krammer, et al., *Nat. Rev. Dis. Primers,* 4:3 (2018)). There are 16 HA and 9 NA subtypes identified in avian populations. These HA subtypes can be classified into 2 groups (Group 1: H1, H2, H5, H6, H8, H9, H11, H12 and H16; Group 2: H3, H4, H7, H14 and H15). Of these subtypes, only H1N1, H2N2 and H3N2 viruses are known to cause pandemics.

The secondary attack rate of seasonal and pandemic influenza in humans is estimated to be about 15% and 33%, respectively (World Health Organization, website who.int/csr/disease/swineflu/assess/disease_swineflu-_assess_20090511/en/ (Accessed in July 2019)). Given the fact that animal influenza viruses may have a potential to trigger pandemics, there is an urgent need for effective and "universal" strategies to control influenza. Of the existing control measures, vaccination is one of the most effective ways to prevent influenza infections. Currently, there are two major classes of influenza vaccines commercially available for human use, which are inactivated and live-attenuated vaccines (Rajao and Perez, *Front. Microbiol.,* 9:123 (2018); Paules, et al., *N. Engl. J. Med.,* 378:7-9 (2018)).

However, current commercial vaccines generally have poor vaccine effectiveness for drifted antigenic variants and short-lived vaccine induced protection. In addition, none of the currently available vaccines are designed for inducing broadly cross-protective immune responses against different animal influenza subtypes, a key feature of "universal influenza vaccine."

There remains a need to develop effective and safe "universal" influenza vaccine. There is also a need for strategies to provide effective and safe "universal" influenza vaccine.

Therefore, it is an object of the invention to provide improved vaccines for prevention of viral infections such as influenza, chicken pox, measles, respiratory syncytial virus, infectious mononucleosis, and Herpes simplex.

It is another object of the invention to provide virus vaccines that provide greater and more durable protection, especially for high risk populations that do not respond well to immunization.

It is another specific object of the invention to provide an improved influenza vaccine.

BRIEF SUMMARY OF THE INVENTION

Disclosed are viruses, and vaccines comprised of and made from such viruses, that include a heterologous nucleic acid segment encoding α-1,3-galactosyltransferase (α-1,3-

GT) such that the nucleic acid segment expresses α-1,3-GT when the virus infects a host cell. Such viruses produce proteins having α-1,3-galactose. The presence of α-1,3-galactose on proteins of infected cells can powerfully stimulate the immune response of the host against the viral proteins of the virus, thus enhancing the effect of the virus as a vaccine. Also disclosed are vaccines that include and/or are produced by such viruses. Also disclosed are methods of making and using such viruses and vaccines, such as administering to a subject in need thereof a vaccine as disclosed and such as making a vaccine that includes one or more viral proteins expressed by a virus as disclosed.

Disclosed are viruses that include a heterologous nucleic acid segment encoding α-1,3-galactosyltransferase (α-1,3-GT) such that the nucleic acid segment expresses α-1,3-GT when the virus infects a host cell. Generally, when such a virus infects a host cell, expression of α-1,3-GT results in proteins in the infected host cell having α-1,3-galactose. For example, in some forms, at least one protein exposed on the surface of the host cell when the virus infects the host cell will have α-1,3-galactose. Also disclosed are vaccines that include and/or are produced by such viruses. Also disclosed are methods of making and using such viruses and vaccines. The heterologous nucleic acid segment encoding α-1,3-GT can be (or be considered to be) a gene or coding portion of a gene encoding α-1,3-GT. The nucleic acid segment/gene generally should be capable of expressing (configured to express) α-1,3-GT when the virus infects a host cell such that the virus expresses α-1,3-GT when the virus infects a host cell.

In some forms, at least one viral protein expressed by the virus when the virus infects the host cell will have α-1,3-galactose. In some forms, the virus is live and attenuated. In some forms, the nucleic acid segment is incorporated into the genome of the virus.

In some forms, the nucleic acid segment is incorporated in frame into the reading frame of a viral coding region of the virus. In some forms, the nucleic acid segment is incorporated immediately before the stop codon of the reading frame of the viral coding region of the virus. In some forms, the virus further comprises a protease cleavage site encoded between the nucleic acid segment and the viral coding region of the virus.

In some forms, the virus is an influenza virus. In some forms, the nucleic acid segment is incorporated in frame into the reading frame of the neuraminidase (NA) coding region of the virus. In some forms, the nucleic acid segment is incorporated immediately before the stop codon of the reading frame of the NA coding region of the virus. In some forms, the virus further comprises a protease cleavage site encoded between the nucleic acid segment and the NA coding region of the virus. In some forms, the protease cleavage site is comprised in a 2A self-cleaving peptide. In some forms, the 2A self-cleaving peptide is derived from porcine teschovirus-1. In some forms, the 2A self-cleaving peptide is flanked by short peptide linkers. In some forms, the peptides linkers are GSG.

In some forms, the α-1,3-GT is a mammalian α-1,3-GT. In some forms, the α-1,3-GT is a mouse α-1,3-GT.

In some forms, the virus is attenuated by serial passage in cultured cells, serial passage in a heterologous host animal, gene deletion in the virus, site-directed mutagenesis of the virus, altering codon usage of the virus, selection of cold-adapted mutants, using a related virus from a heterologous host species, using a naturally occurring attenuated virus strain, or combinations thereof. In some forms, the virus is attenuated by serial passage in cultured cells, wherein the cultured cells are Madin-Darby Canine Kidney (MDCK) cells.

In some forms, the virus is an influenza virus, Influenza A virus, Influenza B virus, Human papillomavirus, Measles virus, Human immune deficiency virus, Rabies virus, Ebolavirus, Hantavirus, Marburg virus, Lassa virus, Dengue virus, Eastern equine encephalitis virus, Hepatitis C virus, Hepatitis A virus, Hepatitis B virus, Hepatitis E virus, Human herpesvirus, Human SARS coronavirus, Mumps virus, Polio virus, Rubella virus, Varicella-zoster virus, Rift valley fever virus, West Nile virus, Yellow fever virus, Human T-lymphotropic virus, or Merkel cell polyomavirus. In some forms, the virus is an influenza virus.

In some forms, the vaccine includes a virus as disclosed. In some forms, the virus is live and attenuated. In some forms, the vaccine includes one or more viral proteins expressed by a virus as disclosed, where the one or more viral proteins comprise $\alpha$-1,3-galactose.

In some forms, the method of using the disclosed vaccines includes administering to a subject in need thereof a vaccine as disclosed. In some forms, the vaccine is administered intranasally, pulmonarily, orally, subcutaneously, intramuscularly, intradermally, or intraperitoneally.

Also disclosed are methods of making a vaccine that includes one or more viral proteins expressed by a virus as disclosed, where the one or more viral proteins comprise $\alpha$-1,3-galactose. In some forms, the method includes infecting a cell with the virus, whereby the one or more viral proteins comprising $\alpha$-1,3-galactose are produced. In some forms, the method further includes purifying the one or more viral proteins.

Additional advantages of the disclosed method and compositions will be set forth in part in the description which follows, and in part will be understood from the description, or can be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIGS. 4A-4F are graphs showing antibody-dependent NK cell assay. Human A549 treated by PBS (FIGS. 4E and 4F), WT virus (FIGS. 4C and 4D) or NAGT (FIGS. 4A and 4B) were incubated with activated human NK cells in the presence (FIGS. 4A, 4C, and 4E) or absence (FIGS. 4B, 4D, and 4F) of heat-inactivated human sera. Percentages of influenza NP positive cells after incubating at different experimental conditions are as shown. These panels were representative FACS plots using a serum sample from a healthy donor.

FIG. 12A shows survival rates of different mouse groups assessed daily for 14 days after challenge (Log-rank test). Each vaccinated group had 16 mice. FIG. 12B shows weight loss of different mouse groups. FIG. 12C shows lung virus titres in mice at days 3 and 7 post-challenge. Data from vaccinated mice were highlighted by grey boxes.

FIG. 15A shows survival rates assessed daily for 14 days after challenge (Log-rank test). Each vaccinated group had ≥20 mice. FIG. 15B shows weight loss of different mouse groups. FIG. 15C shows lung virus titres in mice at days 3 and 7 post-challenge. Data from vaccinated mice were highlighted by grey boxes. FIG. 15D shows HK68-specific neutralizing antibody titres in mice before (3-week post-vaccination) and after challenge (days 7 and 14 post-challenge). Data from vaccinated mice were highlighted by grey boxes. Dotted line for comparison between KO and WT mice at the same time point (t-test). Data represent Mean±SD; *: p<0.05, : p<0.01, *: p<0.001, ****: p<0.0001.

FIGS. 18A-18C are graphs showing percentages of total (FIG. 18A), CD11b$^{lo/–}$ (FIG. 18B) and CD11b$^{hi}$ (FIG. 18C) DCs in infected lung tissues at day 7 post-challenge. Dotted line for comparison between KO and WT mice at the same time point (t-test). Data represent Mean±SD; *: p<0.05, : p<0.01, *: p<0.001, p<0.0001.

FIG. 19A shows survival rates assessed daily for 14 days after challenge (Log-rank test). Each vaccinated group had 10 mice. FIG. 19B shows lung virus titres in mice at day 7 post-challenge. FIG. 19C shows weight loss of different mouse groups. Data represent Mean±SD; *: p<0.05, : p<0.01, **: p<0.0001.

FIG. 20A shows survival rates of these mouse groups after a lethal HK68 virus challenge (10 $MLD_{50}$). Each group had 5 mice. FIG. 20B shows weight loss of different mouse groups. Data represent Mean±SD; *: p<0.05, : p<0.01, *: p<0.001, ****: p<0.0001.

FIG. 21A shows PR8-specific polyfunctional CD8$^+$ T cells in BAL at day 7 post-challenge. Data were re-analyzed from those presented in FIG. 13B. FIG. 21B shows HK68-specific polyfunctional CD4$^+$ T cells in BAL at day 7 post-challenge. Data are re-analyzed from those presented in FIG. 16A. Data represent Mean±SD; *: p<0.05, : p<0.01, *: p<0.001.

DETAILED DESCRIPTION OF THE INVENTION

Figure 1:
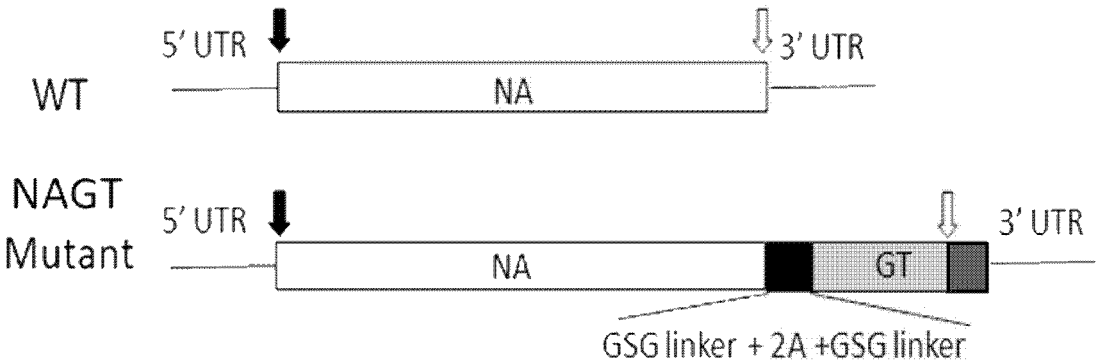
FIG. 1 is a schematic showing the WT and mutated NA segments in cRNA sense. A mouse $\alpha$-1,3-GT gene ORF was introduced immediately before the stop codon of NA ORF (open arrow). An autoproteolytic cleavage site of porcine teschovirus-1 flanked by two short peptide linkers (GSG) were introduced into the junction of NA and $\alpha$-1,3-GT ORF as shown. 5' and 3' untranslated regions (UTRs), and start codon (black arrow) are indicated. Red box represents the 5' end vRNA packaging signal sequence at the NA ORF region.

The disclosed method and compositions can be understood more readily by reference to the following detailed description of particular embodiments and the Example included therein and to the Figures and their previous and following description.

Influenza A viruses have multiple HA subtypes that are antigenically diverse. Classical influenza vaccines are subtype-specific and they cannot induce satisfactory heterosubtypic immunity against multiple influenza subtypes. Live and attenuated viruses that can generate α-Gal epitopes in infected cells and vaccines containing one or more of the viruses are disclosed herein. The disclosed viruses can increase vaccine immunogenicity and the breath of protection, thereby allowing broadly cross-reactive immune responses against different influenza subtypes.

Anti-α-Gal antibody is naturally produced by humans. Therefore, cells infected by the disclosed viruses can facilitate opsonization of the infected cells, resulting in enhanced vaccine-induced immune responses. For example, cells infected with an virus carrying a α-1,3-galactosyltransferase (α-1,3-GT) gene, can enhance phagocytosis of human macrophages and cytotoxicity of NK cells in vitro and can induce 100% protection against a lethal heterosubtypic Group 1 (e.g., H5) or Group 2 (e.g., H3) influenza challenge in vivo. By contrast, the heterosubtypic protective effect of the virus in mice that do not have anti-α-Gal antibody expression is only partial, demonstrating that the enhanced vaccine-induced protection involves anti-α-Gal antibody upon vaccination. Further, the disclosed vaccine can stimulate CD11b$^{lo/–}$ pulmonary dendritic cells, which are known to play a key role in the clearance of influenza virus.

It was discovered that viruses, and vaccines comprised of and made from such viruses, that include a heterologous nucleic acid segment encoding α-1,3-galactosyltransferase (α-1,3-GT) such that the nucleic acid segment expresses α-1,3-GT when the virus infects a host cell are useful because of the expression of α-1,3-GT. Such viruses produce proteins having α-1,3-galactose. The presence of α-1, 3-galactose on proteins of infected cells can powerfully stimulate the immune response of the host against the viral proteins of the virus (because human hosts produce antibodies to α-1,3-galactose), thus enhancing the effect of the virus as a vaccine. Also disclosed are vaccines that include and/or are produced by such viruses. Also disclosed are methods of making and using such viruses and vaccines, such as administering to a subject in need thereof a vaccine as disclosed and such as making a vaccine that includes one or more viral proteins expressed by a virus as disclosed.

It is to be understood that the disclosed method and compositions are not limited to specific synthetic methods, specific analytical techniques, or to particular reagents unless otherwise specified, and, as such, can vary. It is also to be understood that the terminology used herein is for the purpose of describing particular embodiments only and is not intended to be limiting.

As used herein, the term "robust immune response" refers to an antibody-mediated response, cell-mediated adaptive immune response, innate immune response, or a combination thereof, generated following administration of a virus, and generated at a level that provides immune protection to subsequent challenges with the same virus.

As used herein, the terms "immunologic response," "immunological response," or "immune response" refer to the development of a humoral (antibody mediated) response, a cellular (mediated by antigen-specific T cells or their secretion products) response, or both, directed against an antigen. Such a response can be an active response induced by administration of immunogen or a passive response induced by administration of antibody or primed T-cells. A cellular immune response is elicited by the presentation of polypeptide epitopes in association with Class I or Class II MHC molecules to activate antigen-specific $CD4^+$ T helper cells, $CD8^+$ cytotoxic T cells, or both. The response may also involve activation of monocytes, macrophages, NK cells, basophils, dendritic cells, astrocytes, microglia cells, eosinophils or other components of innate immunity. The presence of a cell-mediated immunological response can be determined by proliferation assays ($CD4^+$ T cells) or CTL (cytotoxic T lymphocyte) assays. The relative contributions of humoral and cellular responses to the protective or therapeutic effect of an immunogen can be distinguished by separately isolating antibodies and T-cells from an immunized syngeneic animal and measuring protective or therapeutic effect in a second subject.

As used herein, the term "immune protection" refers to an immunologic response established against one or more antigens of an infectious agent, the immunologic response protecting the host against future challenges by the agent by preventing development of a disease, or development one or more symptoms of a disease, from the future challenge by the agent for at least one year, at least two years, at least three years, at least five years, at least six years, at least seven years, at least eight years, at least nine years, or at least ten years, after the immunological response is established. The future challenges by the agent can be by an agent that is, for example, the same, similar, or different agent, agent subtype, agent strain, or agent particle as the agent used to establish the immune protection. For example, where the infectious agent is a virus, the future challenges by the virus can be by a virus that is, for example, the same, similar, or different virus, virus subtype, virus strain, or virus particle as the agent used to establish the immune protection.

As used herein, the term "live-attenuated virus", or "live attenuated virus", or "attenuated virus" refers to a virus that is altered from an original parental virus or wild type virus in such a way that its ability to infect a host, replicate within a host, be packaged, infect the host again, or a combination thereof, is attenuated. Such attenuation can be, in general, in several or all hosts of the virus, or in only one or several hosts of the virus. Thus, the attenuation of a live-attenuated virus (that is, its ability to infect a host, replicate within a host, be packaged, infect the host again, or a combination thereof, is attenuated) is generally relative to one or more hosts of the virus, with the live-attenuated virus not significantly or detectably attenuated in one of more other hosts of the virus. The live-attenuated viruses disclosed herein are generally genetically altered and can be referred to as mutated, mutant, genetically engineered, recombinant, or a combination.

As used herein, the term "live-attenuated vaccine", or "live attenuated vaccine", or "attenuated vaccine" refers to a pharmaceutical composition containing a live-attenuated pathogen, such as a virus. The pharmaceutical composition contains at least one immunologically active component that induces an immune response in a subject against viruses, protects the subject from or possible death due to viruses, or both, and optionally can include one or more additional components that enhance the immunological activity of the active component. A vaccine can additionally include further components typical to pharmaceutical compositions. The at least one immunologically active component is one or more of the live-attenuated viruses described herein.

As used herein, the term "homologous viral challenge" refers to a second or subsequent viral challenge of the same subject, where the virus is substantially the same virus, viral subtype, strain, or infective viral particle, genetically as that used in the first viral challenge. In a homologous viral challenge—where the second or subsequent viral challenge of the same subject is with a virus of a substantially the same, or similar, viral subtype as the virus used in the first challenge—a homologous immune protection can be obtained.

As used herein, the term "heterologous viral challenge" refers to a second or subsequent viral challenge of the same subject, wherein the virus is a substantially different virus, viral subtype, strain, or infective viral particle, genetically as that used in the first viral challenge. In a heterologous viral challenge—where the second or subsequent viral challenge of the same subject is with a virus of a substantially different viral subtype from the virus used in the first challenge—a heterosubtypic immune protection can be obtained.

As used herein, the term "replication" refers to genome replication. When referring to viruses, the term "replication" also means "viral replication," which encompasses the processes of replication of the viral genome, production of viral proteins, packaging of the viral genome, and formation of a new viral particle.

As used herein, the terms "unaltered replication," "substantially the same replication," and "similar replication," in the context of virus, refer to the replication of a virus that is comparable to or substantially the same as the replication of a reference virus of the same species. For example, when replication of a live-attenuated virus is comparable to or substantially the same as the replication of the replication of the wild type virus of the live-attenuated virus, such replication can be referred to as unaltered or similar replication. The replication can be measured by any technique used to measure viral replication in the art, such as by viral yield or by the rate of viral replication or production. For example, the replication can be measured by the number of plaque forming units, by the number of virions, by the number of viral particles, etc., per se, or per unit time, or per unit weight of an organ, or per unit weight of protein or nucleic acid, or per unit length of nucleic acid. For example, "substantially the same replication rate" refers to a change in the number of viral particles per unit weight of tissue, wherein the change in the number for one virus is substantially the same as the change in the number for another virus. As used herein, the term "substantially the same" refers to the same, or similar value, e.g., a value for replication, or a value for the change in the number of viruses. The values can be identical or can differ from each other within a range of 10%, when compared to each other.

As used herein, the terms "slow replication" and "attenuated replication" in the context of virus, refer to the replication of a virus that is slower or less than the replication of a reference virus of the same species. For example, when replication of a live-attenuated virus is slower or less than the replication of the replication of the wild type virus of the live-attenuated virus, such replication can be referred to as slow or attenuated replication. The replication can be measured by any techniques used to measure viral replication in the art, such as by viral yield or by the rate of viral replication or production. For example, the reduction in replication can be any reduction in the number of plaque forming units, in the number of virions, in the number of viral particles, etc. The reduction can range from, for example, 10% to 90% relative to the number plaque forming units, the number of virions, or the number of viral particles of the wild type virus.

As used herein, the terms "master strain" and "master virus" refer to a viral subtype or strain that can be allowed to recombine with another virulent subtype or strain of a virus to produce a hybrid virus.

As used herein, the term "synonymous substitution" refers to a change of a nucleotide in a genome of an organism that is in a coding region but that do not result in a change to the encoded amino acid sequence.

As used herein, the term "silent mutation" refers to a change of a nucleotide in a genome of an organism that does not significantly alter the phenotype of the organism. Silent mutations can occur in non-coding regions (outside of genes within introns), or they can occur within exons. When they occur within exons or coding regions they either do not result in a change to the encoded amino acid sequence (i.e. a synonymous substitution), or result in the insertion of an alternative amino acid with similar properties to that of the original amino acid, and in either case there is no significant change in phenotype.

As used herein, the term "mammalian host" refers, in the context of a virus, to any mammalian organism that is capable of being infected with and propagating the virus.

As used herein, the term "nucleic acid region" or "genomic region" refers to any region of the genome. The region can be a segment of a genome, a stretch of two or more nucleotides, or the entire genome.

As used herein, the term "involving packaging or splicing" refers, in the context of a virus, to a genomic region that encodes proteins responsible for packaging or splicing the genomic material, or a genomic region that has a nucleic acid sequence that defines sites of packaging or splicing, such as splice donor site and splice acceptor site.

The term "nucleic acid molecule" as used herein refers to any nucleic acid in any possible configuration, such as single stranded, double stranded or a combination thereof. Nucleic acids include for instance DNA molecules, RNA molecules, analogues of the DNA or RNA generated using nucleotide analogues or using nucleic acid chemistry, locked nucleic acid molecules (LNA), protein nucleic acids molecules (PNA) and tecto-RNA molecules (e.g. Liu, B., et al., *J. Am. Chem. Soc.,* 126:4076-4077 (2004)). A PNA molecule is a nucleic acid molecule in which the backbone is a pseudo-peptide rather than a sugar. Accordingly, PNA generally has a charge neutral backbone, in contrast to for example DNA or RNA. Nevertheless, PNA is capable of hybridizing at least complementary and substantially complementary nucleic acid strands, just as e.g. DNA or RNA (to which PNA is considered a structural mimic). An LNA molecule has a modified RNA backbone with a methylene bridge between C4' and O2', which locks the furanose ring in an N-type configuration, providing the respective molecule with a higher duplex stability and nuclease resistance. Unlike a PNA molecule an LNA molecule has a charged backbone. DNA or RNA can be of genomic or synthetic origin and can be single or double stranded. Such nucleic acid can be e.g. mRNA, cRNA, vRNA, synthetic RNA, genomic DNA, cDNA synthetic DNA, a copolymer of DNA and RNA, oligonucleotides, mixed polymers, both sense and antisense strands, or can contain non-natural or derivatized nucleotide bases. A respective nucleic acid can be a nucleic acid containing non-natural nucleotide analogues, a nucleic acid linked to an affinity tag or a label, or both. When referred to herein, the terms "nucleotide sequence(s)," "polynucleotide(s)," "nucleic acid sequence(s)," "nucleic acid(s)," and "nucleic acid molecule" are used interchangeably.

As used herein, the term "wild type virus" refers to a virus in its native form, as it occurs in nature, in its hosts, prior to genetic or other kinds of deliberate manipulations by man.

As used herein, the term "parent virus" refers to a virus prior to initial or further genetic or other kinds of deliberate manipulations by man.

As used herein, the terms "genetically engineered" and "genetically modified" refer to genetic manipulation of an organism, at a nucleotide, codon, gene, segment, frame, or chromosome level using biotechnology. A new nucleotide, base, base pair, or DNA can be inserted in the host genome by first isolating and copying the genetic material of interest using molecular cloning methods to generate a DNA sequence, or by synthesizing the DNA, and then inserting this construct into the host organism. A nucleotide, codon, gene, segment, frame, or chromosome can be removed ("knocked out," added ("knocked in"), or replaced. Genetically engineered organisms can also be referred to as mutated organisms, mutant organisms, recombinant organisms, or a combination. Generally, all of these terms will apply interchangeably to genetically engineered organisms.

As used herein, the term "conserved sites at the amino acid level" refers to sites in a genome of an organism that use the same amino acid at the site more than 90% of the time among different strains of the same organism or among different species of the same genus. As used herein, the term "semi-conserved sites at the amino acid level" refers to sites in a genome of an organism that use the same amino acid at the site more than 80% of the time among different strains of the same organism or among different species of the same genus.

As used herein, the term "host cell" refers to prokaryotic and eukaryotic cells into which the genetic material of a virus, or a recombinant expression vector, can be introduced.

As used herein, the terms "transformed" and "transfected" refer to the introduction of a nucleic acid (e.g. a vector) into a cell by a number of techniques known in the art.

As used herein, the term "immune cell" refers to a cell of hematopoietic origin and that plays a role in the immune response. Immune cells include lymphocytes (e.g., B cells and T cells), natural killer cells, and myeloid cells (e.g., monocytes, macrophages, eosinophils, mast cells, basophils, and granulocytes).

The term 'T cell" refers to a CD4+ T cell or a CD8+ T cell. The term T cell includes TH1 cells, TH2 cells and TH17 cells.

The term "T cell cytotoxicity" includes any immune response that is mediated by CD8+ T cell activation. Exemplary immune responses include cytokine production, CD8+ T cell proliferation, granzyme or perforin production, and clearance of an infectious agent.

As generally used herein "pharmaceutically acceptable" refers to those compounds, materials, compositions, dosage forms, or a combination thereof, which are, within the scope of sound medical judgment, suitable for use in contact with the tissues, organs, bodily fluids, or a combination thereof, of human beings and animals without excessive toxicity, irritation, allergic response, or other problems or complications commensurate with a reasonable benefit/risk ratio.

The terms "individual, "subject," and "patient" refer to any individual who is the target of treatment using the disclosed compositions. The subject can be a mammal. Thus, the subject can be a human. The subjects can be symptomatic or asymptomatic. The term does not denote a particular age or sex. Thus, adult and newborn subjects, whether male or female, are intended to be covered. A subject can include a control subject or a test subject.

As used herein, the term "polypeptide" refers to a chain of amino acids of any length, regardless of modification (e.g., phosphorylation or glycosylation).

As used herein, the terms "effective amount" and "therapeutically effective amount" refer to a dosage sufficient to provide treatment for a disorder, disease, or condition being treated, to induce or enhance an immune response, or to otherwise provide a desired pharmacologic effect, physiologic effect, or both. The precise dosage will vary according to a variety of factors such as subject-dependent variables (e.g., age, immune system health, etc.), the disease, the disease stage, and the treatment being effected.

As used herein, the term "carrier" or "excipient" refers to an organic or inorganic ingredient, natural or synthetic inactive ingredient in a formulation, with which one or more active ingredients are combined.

As used herein, the term "adjuvant" refers to an agent, a pharmacological, an immunological agent, or a combination thereof, that modifies the effect of other agents. Adjuvants can be added to vaccine to modify the immune response by boosting it such as to give a higher amount of antibodies and a longer-lasting protection, thus minimizing the amount of injected foreign material. Adjuvants can also be used to enhance the efficacy of vaccine by helping to subvert the immune response to particular cells type of immune system, for example by activating the T cells instead of antibody-secreting B cells depending on the type of the vaccine.

As used herein, the term "dosage regime" refers to vaccine administration regarding formulation, route of administration, vaccine dose, dosing interval and duration of immune protection.

"Effective amount" or "therapeutically effective amount" refers to that amount of a composition, virus, or vaccine, which, when administered to a mammal, preferably a human, is sufficient to effect treatment of a disease or condition, or prevention of a disease or condition, in the mammal, preferably a human. The amount of a compound, virus, or vaccine, which constitutes a "therapeutically effective amount" will vary depending on the compound, virus, or vaccine, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development; (iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" can be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

Materials

A. Viruses

Disclosed are viruses that include a heterologous nucleic acid segment encoding α-1,3-galactosyltransferase (α-1,3-GT) such that the nucleic acid segment expresses α-1,3-GT when the virus infects a host cell. Generally, when such a virus infects a host cell, expression of α-1,3-GT results in proteins in the infected host cell having α-1,3-galactose. For example, in some forms, at least one protein exposed on the surface of the host cell when the virus infects the host cell will have α-1,3-galactose. The heterologous nucleic acid segment encoding α-1,3-GT can be (or be considered to be) a gene or coding portion of a gene encoding α-1,3-GT. The nucleic acid segment/gene generally should be capable of expressing (configured to express) α-1,3-GT when the virus infects a host cell such that the virus expresses α-1,3-GT when the virus infects a host cell.

In some forms, at least one viral protein expressed by the virus when the virus infects the host cell will have α-1,3-galactose. In some forms, the virus is live and attenuated.

In some forms, the nucleic acid segment is incorporated into the genome of the virus. In some forms, the nucleic acid segment is incorporated in frame into the reading frame of a viral coding region of the virus. In some forms, the nucleic acid segment is incorporated immediately before the stop codon of the reading frame of the viral coding region of the virus. In some forms, the virus further comprises a protease cleavage site encoded between the nucleic acid segment and the viral coding region of the virus.

In some forms, the virus is an influenza virus. In some forms, the nucleic acid segment is incorporated in frame into the reading frame of the neuraminidase (NA) coding region of the virus. In some forms, the nucleic acid segment is incorporated immediately before the stop codon of the reading frame of the NA coding region of the virus. In some forms, the virus further comprises a protease cleavage site encoded between the nucleic acid segment and the NA coding region of the virus. In some forms, the protease cleavage site is comprised in a 2A self-cleaving peptide. In some forms, the 2A self-cleaving peptide is derived from porcine teschovirus-1. In some forms, the 2A self-cleaving peptide is flanked by short peptide linkers. In some forms, the peptides linkers are GSG.

In some forms, the α-1,3-GT is a mammalian α-1,3-GT. In some forms, the α-1,3-GT is a mouse α-1,3-GT.

In some forms, the virus is attenuated by serial passage in cultured cells, serial passage in a heterologous host animal, gene deletion in the virus, site-directed mutagenesis of the virus, altering codon usage of the virus, selection of cold-adapted mutants, using a related virus from a heterologous host species, using a naturally occurring attenuated virus strain, or combinations thereof. In some forms, the virus is attenuated by serial passage in cultured cells, wherein the cultured cells are Madin-Darby Canine Kidney (MDCK) cells.

Any virus can be used in and to make the disclosed viruses. Preferred are viruses that cause disease in humans. For example, the virus can be Aichi virus, Australian bat lyssavirus, Banna virus, Barmah forest virus, Bunyamwera virus, Bunyavirus La Crosse, Bunyavirus snowshoe hare, Cercopithecine herpesvirus, Chandipura virus, Chikungunya virus, Coxsackievirus, Crimean-Congo hemorrhagic fever virus, Dengue virus, Dhori virus, Dugbe virus, Duvenhage virus, Eastern equine encephalitis virus, Ebolavirus, Echovirus, Encephalomyocarditis virus, Epstein-Barr virus, European bat lyssavirus, Hantaan virus, Hendra virus, Hepatitis A virus, Hepatitis B virus, Hepatitis C virus, Hepatitis E virus, Hepatitis delta virus, Human adenovirus, Human astrovirus, Human coronavirus, Human cytomegalovirus, Human enterovirus 68, 70, Human herpesvirus 1, Human herpesvirus 2, Human herpesvirus 6, Human herpesvirus 7, Human herpesvirus 8, Human immunodeficiency virus, Human papillomavirus 1, Human papillomavirus 2, Human papillomavirus, Human papillomavirus 16, Human papillomavirus 18, Human parainfluenza, Human parvovirus, Human parvovirus B19, Human respiratory syncytial virus, Human rhinovirus, Human SARS coronavirus, Human T-lymphotropic virus, Human torovirus, Influenza virus, Influenza A virus, Influenza B virus, Influenza C virus, Isfahan virus, JC polyomavirus, Japanese encephalitis virus, Junin arenavirus, KI Polyomavirus, Kunjin virus, Lagos bat virus, Lake Victoria marburgvirus, Langat virus, Lassa virus, Lordsdale virus, Louping ill virus, Lymphocytic choriomeningitis virus, Machupo virus, Mayaro virus, MERS coronavirus, Measles virus, Mengo encephalomyocarditis virus, Merkel cell polyomavirus, Mokola virus, Molluscum contagiosum virus, Monkeypox virus, Mumps virus, Murray valley encephalitis virus, New York virus, Nipah virus, Norwalk virus, O'nyong-nyong virus, Orf virus, Oropouche virus, Pichinde virus, Poliovirus, Punta toro phlebovirus, Puumala virus, Rabies virus, Rift valley fever virus, Ross river virus, Rotavirus, Rotavirus A, Rotavirus B, Rotavirus C, Rubella virus, Sagiyama virus, Salivirus A, Sandfly fever sicilian virus, Sapporo virus, Semliki forest virus, Seoul virus, Sindbis virus, Southampton virus, St. louis encephalitis virus, Tick-borne powassan virus, Toscana virus, Uukuniemi virus, Varicella-zoster virus, Variola virus, Venezuelan equine encephalitis virus, Vesicular stomatitis virus, Western equine encephalitis virus, West Nile virus, Yellow fever virus, or Zika virus. Characteristics of some disease-causing human viruses are shown in Table 1.

Preferred viruses include Influenza virus, Influenza A virus, Influenza B virus, Human papillomavirus, Measles virus, Human immune deficiency virus, Rabies virus, Ebolavirus, Hantavirus, Marburg virus, Lassa virus, Dengue virus, Eastern equine encephalitis virus, Hepatitis C virus, Hepatitis A virus, Hepatitis B virus, Hepatitis E virus, Human herpesvirus, Human SARS coronavirus, Mumps virus, Polio virus, Rubella virus, Varicella-zoster virus, Rift valley fever virus, West Nile virus, Yellow fever virus, Human T-lymphotropic virus, and Merkel cell polyomavirus.

TABLE 1

Human Disease-Causing Viruses

| Virus | Genus, Family | Host | Disease |
|---|---|---|---|
| Aichi virus | Kobuvirus, Picornaviridae | Human | Gastroenteritis |
| Australian bat lyssavirus | Lyssavirus, Rhabdoviridae | Human, bats | Fatal encephalitis |
| Banna virus | Seadornavirus, Reoviridae | Human, cattle, pig, mosquitoes | Encephalitis |
| Barmah forest virus | Alphavirus, Togaviridae | Human, marsupials, mosquitoes | Fever, joint pain |
| Bunyamwera virus | Orthobunyavirus, Bunyaviridae | Human, mosquitoes | Encephalitis |
| Bunyavirus La Crosse | Orthobunyavirus, Bunyaviridae | Human, deer, mosquitoes, tamias | Encephalitis |
| Bunyavirus snowshoe hare | Orthobunyavirus, Bunyaviridae | Human, rodents, mosquitoes | Encephalitis |
| Cercopithecine herpesvirus | Lymphocryptovirus, Herpesviridae | Human, monkeys | Encephalitis |
| Chandipura virus | Vesiculovirus, Rhabdoviridae | Human, sandflies | Encephalitis |
| Chikungunya virus | Alphavirus, Togaviridae | Human, monkeys, mosquitoes | Fever, joint pain |
| Coxsackievirus | Enterovirus, Picornaviridae | Human | Meningitis, myocarditis, paralysis |
| Crimean-Congo hemorrhagic fever virus | Nairovirus, Bunyaviridae | Human, vertebrates, ticks | Hemorrhagic fever |
| Dengue virus | Flavivirus, Flaviviridae | Human, mosquitoes | Hemorrhagic fever |
| Dhori virus | Thogotovirus, Orthomyxoviridae | Human, ticks | Fever, encephalitis |
| Dugbe virus | Nairovirus, Bunyaviridae | Human, ticks | Thrombocytopaenia |
| Duvenhage virus | Lyssavirus, Rhabdoviridae | Human, mammals | Fatal encephalitis |
| Eastern equine encephalitis virus | Alphavirus, Togaviridae | Human, birds, mosquitoes | Encephalitis |
| Ebolavirus | Ebolavirus, Filoviridae | Human, monkeys, bats | Hemorrhagic fever |
| Echovirus | Enterovirus, Picornaviridae | Human | Common cold |
| Encephalomyocarditis virus | Cardiovirus, Picornaviridae | Human, mouse, rat, pig | Encephalitis |
| Epstein-Barr virus | Lymphocryptovirus, Herpesviridae | Human | Mononucleosis |

TABLE 1-continued

Human Disease-Causing Viruses

| Virus | Genus, Family | Host | Disease |
|---|---|---|---|
| European bat lyssavirus | Lyssavirus, Rhabdovirus | Human, bats | Fatal encephalitis |
| Hantaan virus | Hantavirus, Bunyaviridae | Human, rodents | Renal or respiratory syndrome |
| Hendra virus | Henipavirus, paramyxoviridae | Human, horse, bats | Encephalitis |
| Hepatitis A virus | Hepatovirus, picornaviridae | Human | Hepatitis |
| Hepatitis B virus | Orthohepadnavirus, Hepadnaviridae | Human, Chimpanzees | Hepatitis |
| Hepatitis C virus | Hepacivirus, Flaviviridae | Human | Hepatitis |
| Hepatitis E virus | Hepevirus, Unassigned | Human, pig, monkeys, some rodents, chicken | Hepatitis |
| Hepatitis delta virus | Deltavirus, Unassigned | Human | Hepatitis |
| Human adenovirus | Mastadenovirus, Adenoviridae | Human | Respiratory |
| Human astrovirus | Mamastrovirus, Astroviridae | Human | Gastroenteritis |
| Human coronavirus | Alphacoronavirus, Coronaviridae | Human | Respiratory |
| Human cytomegalovirus | Cytomegalovirus, Herpesviridae | Human | Mononucleosis, pneumonia |
| Human enterovirus 68, 70 | Enterovirus, Picornaviridae | Human | Diarrhea, neurological disorder |
| Human herpesvirus 1 | Simplexvirus, Herpesviridae | Human | Skin lesions |
| Human herpesvirus 2 | Simplexvirus, Herpesviridae | Human | Skin lesions |
| Human herpesvirus 6 | Roseolovirus, Herpesviridae | Human | Skin lesions |
| Human herpesvirus 7 | Roseolovirus, Herpesviridae | Human | Skin lesions |
| Human herpesvirus 8 | Rhadinovirus, Herpesviridae | Human | Skin lymphoma |
| Human immunodeficiency virus | Lentivirus, Retroviridae | Human | AIDS |
| Human papillomavirus 1 | Mupapillomavirus, Papillomaviridae | Human | Skin warts |
| Human papillomavirus 2 | Alphapapillomavirus, Papillomaviridae | Human | Skin warts |
| Human papillomavirus 16, 18 | Alphapapillomavirus, Papillomaviridae | Human | Genital warts, cervical cancer |
| Human parainfluenza | Respirovirus, Paramyxoviridae | Human | Respiratory |
| Human parvovirus B19 | Erythrovirus, Parvoviridae | Human | Skin lesion |
| Human respiratory syncytial virus | Orthopneumovirus, Pneumoviridae | Human | Respiratory |
| Human rhinovirus | Enterovirus, Picornaviridae | Human | Respiratory |
| Human SARS coronavirus | Betacoronavirus, Coronaviridae | Human, palm civet | Respiratory |
| Human T-lymphotropic virus | Deltaretrovirus, Retroviridae | Human | Leukemia |
| Human torovirus | Torovirus, Coronaviridae | Human | Gastroenteritis |
| Influenza A virus | Influenzavirus A, Orthomyxoviridae | Human, birds, pigs | Flu |
| Influenza B virus | Influenzavirus B, Orthomyxoviridae | Human | Flu |
| Influenza C virus | Influenzavirus C, Orthomyxoviridae | Human | Flu |
| Isfahan virus | Vesiculovirus, Rhabdoviridae | Human, sandflies, gerbils | Undocumented, encephalitis? |
| JC polyomavirus | Polyomavirus, Polyomaviridae | Human | Encephalitis |
| Japanese encephalitis virus | Flavivirus, Flaviviridae | Human, horses, birds, mosquitoes | Encephalitis |
| Junin arenavirus | Arenavirus, Arenaviridae | Human, rodents | Hemorrhagic fever |
| KI Polyomavirus | Polyomavirus, Polyomaviridae | Human | Encephalitis |
| Kunjin virus | Flavivirus, Flaviviridae | Human, horses, birds, mosquitoes | Encephalitis |
| Lagos bat virus | Lyssavirus, Rhabdoviridae | Human, mammals | Fatal encephalitis |
| Lake Victoria marburgvirus | Marburgvirus, Filoviridae | Human, monkeys, bats | Hemorrhagic fever |
| Langat virus | Flavivirus, Flaviviridae | Human, ticks | Encephalitis |
| Lassa virus | Arenavirus, Arenaviridae | Human, rats | Hemorrhagic fever |
| Lordsdale virus | Norovirus, Caliciviridae | Human | Gastroenteritis |
| Louping ill virus | Flavivirus, Flaviviridae | Human, mammals, ticks | Encephalitis |
| Lymphocytic choriomeningitis virus | Arenavirus, Arenaviridae | Human, rodents | Encephalitis |
| Machupo virus | Arenavirus, Arenaviridae | Human, monkeys, mouse | Encephalitis |
| Mayaro virus | Alphavirus, Togaviridae | Human, mosquitoes | Fever, joint pain |
| MERS coronavirus | Betacoronavirus, Coronaviridae | Human, Tomb bat | Respiratory |
| Measles virus | Morbilivirus, Paramyxoviridae | Human | Fever, rash |
| Mengo encephalomyocarditis virus | Cardiovirus, Picornaviridae | Human, mouse, rabbit | Encephalitis |
| Merkel cell polyomavirus | Polyomavirus, Polyomaviridae | Human | Merkel cell carcinoma |
| Mokola virus | Lyssavirus, Rhabdoviridae | Human, rodents, cat, dog shrew | Encephalitis |
| Molluscum contagiosum virus | Molluscipoxvirus, Poxviridae | Human | Skin lesions |
| Monkeypox virus | Orthopoxvirus, Poxviridae | Human, mouse, prairie dog | Skin lesions |

TABLE 1-continued

Human Disease-Causing Viruses

| Virus | Genus, Family | Host | Disease |
|---|---|---|---|
| Mumps virus | Rubulavirus, Paramyxoviridae | Human | Mumps |
| Murray valley encephalitis virus | Flavivirus, Flaviviridae | Human, mosquitoes | Encephalitis |
| New York virus | Hantavirus, Bunyavirus | Human, mouse | Hemorrhagic fever |
| Nipah virus | Henipavirus, Paramyxoviridae | Human, bats | Encephalitis |
| Norwalk virus | Norovirus, Caliciviridae | Human | Gastroenteritis |
| O'nyong-nyong virus | Alphavirus, Togaviridae | Human, mosquitoes | Fever, joint pain |
| Orf virus | Parapoxvirus, Poxviridae | Human, mammals | Skin lesions |
| Oropouche virus | Orthobunyavirus, Bunyaviridae | Human, wild animals(sloths) | Fever, joint pain |
| Pichinde virus | Arenavirus, Arenaviridae | Human, rat, guinea pig | Hemorrhagic fever |
| Poliovirus | Enterovirus, Picornaviridae | Human, mammals | Poliomyelitis |
| Punta toro phlebovirus | Phlebovirus, Bunyaviridae | Human, sandflies | Hemorrhagic fever |
| Puumala virus | Hantavirus, Bunyavirus | Human, bank vole | Hemorrhagic fever |
| Rabies virus | Lyssavirus, Rhabdoviridae | Human, mammals | Fatal encephalitis |
| Rift valley fever virus | Phlebovirus, Bunyaviridae | Human, mammals, mosquitoes, sandflies | Hemorrhagic fever |
| Ross river virus | Alphavirus, Togaviridae | Human, mosquitoes, marsupials | Fever, joint pain |
| Rotavirus A | Rotavirus, Reoviridae | Human | Gastroenteritis |
| Rotavirus B | Rotavirus, Reoviridae | Human | Gastroenteritis |
| Rotavirus C | Rotavirus, Reoviridae | Human | Gastroenteritis |
| Rubella virus | Rubivirus, Togaviridae | Human | Rubella |
| Sagiyama virus | Alphavirus, Togaviridae | Human, horse, pig, mosquitoes | Fever, joint pain |
| Salivirus A | Salivirus, Picornaviridae | Human | Gastroenteritis |
| Sandfly fever sicilian virus | Phlebovirus, Bunyaviridae | Human, sandflies | Hemorrhagic fever |
| Sapporo virus | Sapovirus, Caliciviridae | Human | Gastroenteritis |
| Semliki forest virus | Alphavirus, Togaviridae | Human, birds, hedgehog, mosquitoes | Fever, joint pain |
| Seoul virus | Hantavirus, Bunyavirus | Human, rats | Hemorrhagic fever |
| Sindbis virus | Alphavirus, Togaviridae | Human, birds, mosquitoes | Pogosta disease Fever, joint pain |
| Southampton virus | Norovirus, Caliciviridae | Human | Gastroenteritis |
| St. louis encephalitis virus | Flavivirus, Flaviviridae | Human, birds, mosquitoes | Encephalitis |
| Tick-borne powassan virus | Flavivirus, Flaviviridae | Human, ticks | Encephalitis |
| Toscana virus | Phlebovirus, Bunyaviridae | Human, mosquitoes | Hemorrhagic fever |
| Uukuniemi virus | Phlebovirus, Bunyaviridae | Human, ticks | Hemorrhagic fever |
| Varicella-zoster virus | Varicellovirus, Herpesviridae | Human | Varicella |
| Variola virus | Orthopoxvirus, Poxviridae | Human | Variola |
| Venezuelan equine encephalitis virus | Alphavirus, Togaviridae | Human, rodents, mosquitoes | Fever, joint pain |
| Vesicular stomatitis virus | Vesiculovirus, Rhabdoviridae | Human, cattle, horse, pig, flies | Encephalitis |
| Western equine encephalitis virus | Alphavirus, Togaviridae | Human, vertebrates, mosquitoes | Fever, joint pain |
| West Nile virus | Flavivirus, Flaviviridae | Human, birds, ticks, mosquitoes | Encephalitis |
| Yellow fever virus | Flavivirus, Flaviviridae | Human, monkeys, mosquitoes | Hemorrhagic fever |
| Zika virus | Flavivirus, Flaviviridae | Human, monkeys, mosquitoes | Fever, joint pain, rash |

Examples of viruses suitable for generating live-attenuated viruses include viruses of virus families Adenoviridae, Papillomaviridae, Parvoviridae, Herpesviridae, Poxviridae, Hepadnaviridae, Polyomaviridae, Anelloviridae, Reoviridae, Picornaviridae, Caliciviridae, Togaviridae, Arenaviridae, Flaviviridae, Orthomyxoviridae, Paramyxoviridae, Bunyaviridae, Rhabdoviridae, Filoviridae, Coronaviridae, Astroviridae, Bornaviridae, Arteriviridae, Hepeviridae. Viruses must generate mRNAs from their genomes to produce proteins and replicate themselves, but different mechanisms are used to achieve this in each virus family. Viral genomes may be single-stranded (ss) or double-stranded (ds), RNA or DNA, and may or may not use reverse transcriptase (RT). In addition, ssRNA viruses may be either sense (+) or antisense (−).

This classification places viruses into seven groups:

I: dsDNA viruses (e.g. Adenoviruses, Herpesviruses, Poxviruses)

II: ssDNA viruses (+ strand or "sense") DNA (e.g. Parvoviruses)

III: dsRNA viruses (e.g. Reoviruses)

IV: (+)ssRNA viruses (+ strand or sense) RNA (e.g. Picornaviruses, Togaviruses)

V: (−)ssRNA viruses (− strand or antisense) RNA (e.g. Orthomyxoviruses, Rhabdoviruses)

VI: ssRNA-RT viruses (+ strand or sense) RNA with DNA intermediate in life-cycle (e.g. Retroviruses)

VII: dsDNA-RT viruses (e.g. Hepadnaviruses)

Examples of DNA and RNA viruses are presented in Table 2 and Table 3.

yxoviridae include Influenza A virus, Influenza B virus and Influenza C virus. Bunyaviridae include Bunyamwera virus,

TABLE 2

Examples of DNA viruses useful for generating live-attenuated viruses.

| Virus Family | Examples (common names) | Virion naked/enveloped | Capsid Symmetry | Nucleic acid type | Group |
|---|---|---|---|---|---|
| 1. Adenoviridae | Adenovirus, Infectious canine hepatitis virus | Naked | Icosahedral | ds | I |
| 2. Papillomaviridae | Papillomavirus | Naked | Icosahedral | ds circular | I |
| 3. Parvoviridae | Parvovirus B19, Canine parvovirus | Naked | Icosahedral | ss | II |
| 4. Herpesviridae | Herpes simplex virus, varicella-zoster virus, Cytomegalovirus, Epstein-Barr virus | Enveloped | Icosahedral | ds | I |
| 5. Poxviridae | Smallpox virus, cow pox virus, sheep pox virus, orf virus, monkey pox virus, vaccinia virus | Complex coats | Complex | ds | I |
| 6. Hepadnaviridae | Hepatitis B virus | Enveloped | Icosahedral | circular, partially ds | VII |
| 7. Polyomaviridae | Polyoma virus; JC virus (progressive multifocal leukoencephalopathy) | Naked | Icosahedral | ds circular | I |
| 8. Anelloviridae | Torque teno virus | | | | |

TABLE 3

Examples of RNA viruses useful for generating live-attenuated viruses.

| Virus Family | Examples (common names) | Capsid naked/enveloped | Capsid Symmetry | Nucleic acid type | Group |
|---|---|---|---|---|---|
| 1. Reoviridae | Reovirus, Rotavirus | Naked | Icosahedral | ds | III |
| 2. Picornaviridae | Enterovirus, Rhinovirus, Hepatovirus, Cardiovirus, Aphthovirus, Poliovirus, Parechovirus, Erbovirus, Kobuvirus, Teschovirus, Coxsackie | Naked | Icosahedral | ss | IV |
| 3. Caliciviridae | Norwalk virus | Naked | Icosahedral | ss | IV |
| 4. Togaviridae | Rubella virus | Enveloped | Icosahedral | ss | IV |
| 5. Arenaviridae | Lymphocytic choriomeningitis virus | Enveloped | Complex | ss(−) | V |
| 6. Flaviviridae | Dengue virus, Hepatitis C virus, Yellow fever virus | Enveloped | Icosahedral | ss | IV |
| 7. Orthomyxoviridae | Influenza virus A, Influenza virus B, Influenza virus C, Isavirus, Thogotovirus | Enveloped | Helical | ss(−) | V |
| 8. Paramyxoviridae | Measles virus, Mumps virus, Respiratory syncytial virus, Rinderpest virus, Canine distemper virus | Enveloped | Helical | ss(−) | V |
| 9. Bunyaviridae | California encephalitis virus, Hantavirus | Enveloped | Helical | ss(−) | V |
| 10. Rhabdoviridae | Rabies virus | Enveloped | Helical | ss(−) | V |
| 11. Filoviridae | Ebola virus, Marburg virus | Enveloped | Helical | ss(−) | V |
| 12. Coronaviridae | Corona virus | Enveloped | Helical | ss | IV |
| 13. Astroviridae | Astrovirus | Naked | Icosahedral | ss | IV |
| 14. Bornaviridae | Borna disease virus | Enveloped | Helical | ss(−) | V |
| 15. Arteriviridae | Arterivirus, Equine Arteritis Virus | Enveloped | Icosahedral | ss | IV |
| 16. Hepeviridae | Hepatitis E virus | Naked | Icosahedral | ss | IV |

Viruses with a segmented genome are also suitable for forming live-attenuated viruses described herein. Viruses with segmented genomes include viruses of the family orthomyxoviridae, bunyaviridae and arenaviridae. Orthom- LaCrosse virus, California encephalitis virus, Rift-Valley-fever virus and hamtaviruses. Arenaviridae include Lymphocytic choriomeningitis virus (LCMV), Lassa virus, Juni virus (Argentine haemorrhagic fever).

1. Influenza Viruses

In some forms, the viruses described herein are influenza type A or influenza type B viruses. The influenza type A or influenza type B viruses disclosed herein can be classified according to the World Health Organization's revised system of nomenclature for influenza viruses (Bulletin of the World Health Organization, 58 (4):585-591 (1980)). The revised system of nomenclature is similar to the 1971 system in that it consists of two parts: (a) a type and strain designation, and (b) for influenza A viruses, a description of the antigenic specificity of the surface antigens (H and N).

The strain designation for influenza virus types A, B, and C contains the following information:

1. A description of the antigenic type of the virus based on the antigenic specificity of the NP antigen (type A, B, or C).

2. The host of origin. This is not indicated for strains isolated from human sources but is indicated for all strains isolated from non-human hosts, e.g., swine, horse (equine), chicken, and turkey. For viruses from non-human species, both the Latin binomial nomenclature and the common name of the host of origin are used, e.g., *Anas acuta* (pintail duck). Thereafter, the common name of the species is used for the strain, e.g., A/duck/USSR/695/76 (H2N3). When viruses are isolated from nonliving material, the nature of the material is specified, e.g., A/lake water/Wisconsin/1/79.

3. Geographical origin.

4. Strain number.

5. Year of isolation.

For influenza A viruses, the antigenic description, in parentheses, follows the strain designation and includes the following information.

(a) An index describing the antigenic character of the hemagglutinin, i.e., H1, H2, H3, H4, etc. The numbering of subtypes is a simple sequential system which applies uniformly to influenza viruses from all sources.

(b) An index describing the antigenic character of the neuraminidase, i.e., N1, N2, N3, N4, etc. As with the H antigen subtype, this is a simple sequential numbering system applied uniformly to all influenza A viruses.

An exemplary nomenclature for the Influenza type A viruses isolated from humans is presented in Table 4.

TABLE 4

Examples of reference strains and subtypes of
hemagglutinin and neuraminidase antigens of
influenza A viruses isolated from humans.

| H and N subtypes | Reference strains |
|---|---|
| H1N1 | A/PR/8/34 (H1N1) |
| | A/Weiss/43 (H1N1) |
| | A/FM1/47 (H1N1) |
| | A/England/1/51 (H1N1) |
| | A/Denver/1/57 (H1N1) |
| | A/New Jersey/8/76 (H1N1) |
| | A/USSR/90/77 (H1N1) |
| H2N2 | A/Singapore/1/57 (H2N2) |
| | A/Japan/305/57 (H2N2) |
| | A/England/12/64 (H2N2) |
| | A/Tokyo/3/67 (H2N2) |
| H3N2 | A/Hong Kong/1/68 (H3N2) |
| | A/England/42/72 (H3N2) |
| | A/Port Chalmers/1/73 (H3N2) |
| | A/Victoria/3/75 (H3N2) |
| | A/Texas/1/77 (H3N2) | i. Influenza Type A

A live, attenuated influenza A virus described herein, including, for example, a respective virus in a pharmaceutical composition, can be based on any influenza A virus such as a bird flu, human flu, swine influenza, equine influenza or a canine influenza. Various different influenza A virus subtypes exist, differing in the nature of the HA and NA glycoproteins on their surface. Influenza A viruses are accordingly usually categorized into subtypes based on the combination of protein forms of Hemagglutinin and Neuraminidase present, two proteins on the surface of the viral envelope. Eighteen Hemagglutinin forms (H1 to H18) and eleven Neuraminidase forms (N1 to N11) have been identified.

Suitable virus strains include, but are not limited to H1N1, H1N2, H1N3, H1N4, H1N5, H1N6, H1N7, H1N8, H1N9, H2N1, H2N2, H2N3, H2N4, H2N5, H2N6, H2N7, H2N8, H2N9, H3N1, H3N2, H3N3, H3N4, H3N5, H3N6, H3N7, H3N8, H3N9, H4N1, H4N2, H4N3, H4N5, H4N6, H4N7, H4N8, H5N1, H5N2, H5N3, H5N4, H5N6, H5N7, H5N8, H5N9, H6N1, H6N2, H6N3, H6N4, H6N5, H6N7, H6N8, H6N9, H7N1, H7N2, H7N3, H7N4, H7N5, H7N6, H7N7, H7N8, H7N9, H8N1, H8N2, H8N3, H8N4, H8N5, H8N6, H8N7, H9N1, H9N2, H9N3, H9N4, H9N5, H9N6, H9N7, H9N8, H9N9, H10N1, H10N2, H10N3, H10N4, H10N5, H10N6, H10N7, H10N8, H10N9, H11N1, H11N2, H11N3, H11N4, H11N5, H11N6, H11N7, H11N8, H11N9, H12N1, H12N2, H12N3, H12N4, H12N5, H12N6, H12N7, H12N8, H12N9, H13N1, H13N2, H13N3, H13N4, H13N5, H13N6, H13N8, H14N3, H14N5, H14N6, H15N8, H15N9, H16N3. In some forms the influenza virus is one of the strains H1N1, H1N2, H2N2, H3N1, H3N2, H5N1 and H7N7.

An example of a H1N1 strain is Influenza A virus strain A/Brisbane/59/2007 (H1N1), A/Puerto Rico/8/1934(H1N1) with Gene bank accession number NC 002016, NC 002017, NC 002018, NC 002019, NC 002020, NC 002021, NC 002022, NC 002023. Further examples of a H1N1 strain are Influenza A strain A/Brevig Mission/i/1918 H1N1) (Influenza A virus (strain A/South Carolina/i/1918 H1N1), Influenza A strain A/Russia:St.Petersburg/8/2006 H1N1, Influenza A strain A/USA:Texas/UR06-0195/2007 H1N1-strain A/Brevig Mission/i/1918 H1N1, Influenza A strain A/South Carolina/i/1918 H1N1, Influenza A strain A/Swine/Iowa/15/1930 H1N1, Influenza A strain A/Wilson-Smith/1933 H1N1, Influenza A strain A/WS/1933 H1N1, and strain A/USA: Phila/1935 H1N1. A further example of a H1N1 strain is Influenza A virus strain A/New Zealand:South Canterbury/35/2000 H1N1. An example of a H1N2 strain is Influenza A virus strain A/Xianfeng/3/1989 H1N2. Two examples of a H1N3 strain are Influenza A/duck/NZL/160/1976 H1N3 and strain A/Whale/Pacific ocean/19/1976 H1N3. An example of a H1N4 strain is Influenza A virus strain A/mallard/Netherlands/30/2006 H1N4. An example of a H1N5 strain is Influenza A virus strain A/pintail duck/ALB/631/1981 H1N5. An example of a H1N6 strain is Influenza A virus strain A/murre/Alaska/305/1976 H1N6. An example of a H1N7 strain is Influenza A virus A/swine/England/191973/92 H1N7. An example of a H1N8 strain is strain A/Egyptian goose/South Africa/AI1448/2007. An example of a H2N1 strain is Influenza A virus strain A/Japan/Bellamy/57 H2N1. An example of a H2N2 strain is Influenza A virus strain A/Korea/426/68 H2N2 with Gene bank accession numbers NC 007366, NC 007367, NC 007368, NC 007369, NC 007370, NC 007374, NC 007375, NC 007376, NC 007377, NC 007378, NC 007380, NC 007381 and NC 007382. Three further examples of a H2N2 strain are Influenza A strain A/Japan/305/1957 H2N2, A/Czech Republic/1/1966 H2N2 and strain A/Singapore/1/1957 H2N2. An example of a H2N3 strain is Influenza A virus strain A/mallard/Minnesota/Sg-00692/2008 H2N3. An example of a H2N4 strain is A/mallard/Alberta/149/2002 H2N4. An example of a H2N5 strain is Influenza A virus strain A/tern/Australia/1/04 H2N5. An example of a H2N6 strain is Influenza A virus strain A/thick-billed murre/Alaska/44145-199/2006 H2N6. An example of a H2N7 strain is Influenza A virus strain A/northern shoveler/California/HKWF1128/2007 H2N7. An example of a H2N8 strain is Influenza A virus strain A/turkey/CA/1797/2008 H2N8. An example of a H2N9 strain is Influenza A virus strain A/duck/Germany/1972 H2N9. An example of a H3N1 strain is Influenza A virus strain A/mallard duck/ALB/26/1976 H3N1. An example of a H3N2 strain is Influenza A virus strain A/New York/392/2004 H3N2 with Gene bank accession numbers NC 007371, NC 007372 and NC 007373. Five further example of a H3N2 strain are Influenza A virus strain NX-31 H3N2, strain A/Hong Kong/5/1983 H3N2, A/Rio/6/69 H3N2, A/Hong Kong/MA/1968 H3N2 and Influenza A virus strain A/Shanghai/N12/2007 H3N2. An example of a H3N3 strain is Influenza A virus strain A/duck/Hong Kong/22A/1976 H3N3. An example of a H3N4 strain is Influenza A virus strain A/mallard duck/ALB/1012/1979 H3N4. An example of a H3N5 strain is Influenza A virus strain A/northern shoveler/California/HKWF1046/2007 H3N5. An example of a H3N6 strain is Influenza A virus strain A/Chicken/Nanchang/9-220/2000 H3N6. Examples of a H3N8 strain are Influenza A strain A/Equine/Miami/1/1963 H3N8 and strain A/Duck/Ukraine/1/1963 H3N8. An example of a H3N9 strain is Influenza A virus strain A/swan/Shimane/227/01 H3N9.

An example of a H4N1 strain is Influenza A virus strain A/chicken/Singapore/1992(H4N1). An example of a H4N2 strain is Influenza A virus strain A/duck/Hong Kong/24/1976(H4N2). An example of a H4N3 strain is Influenza A virus strain A/mallard/Sweden/65/2005(H4N3). An example of a H4N4 strain is Influenza A virus strain A/Grey teal/Australia/2/1979 H4N4. An example of a H4N5 strain is Influenza A virus strain A/duck/Hokkaido/1058/2001 (H4N5). Two examples of a H4N6 strain are Influenza A virus strain A/Duck/Czechoslovakia/1956 H4N6 and Influenza A virus strain A/Duck/Alberta/28/1976 H4N6. An example of a H4N7 strain is Influenza A virus strain A/duck/Mongolia/583/02 H4N7. An example of a H4N8 strain is Influenza A virus strain A/Chicken/Alabama/1/1975 H4N8. An example of a H4N9 strain is Influenza A virus strain A/WDk/ST/988/2000(H4N9). An example of a H5N1 strain is Influenza A virus (A/Goose/Guangdong/1/96(H5N1)) with Gene bank accession numbers NC 007357, NC 007358, NC 007359, NC 007360, NC 007362, NC 007363, and NC 007364. Further examples of a H5N1 strain are Influenza A strain A/Duck/Hong Kong/2986.1/2000 H5N1, Influenza A strain A/Silky Chicken/Hong Kong/SF189/2001 H5N1, Influenza A strain A/Chicken/Hong KongNU562/2001 H5N1, Influenza A strain A/Chicken/Hong Kong/FY150/2001 H5N1, Influenza A strain A/Chicken/Hong Kong/715.5/2001 H5N1, Influenza A strain A/Guinea fowl/Hong Kong/38/2002 H5N1, Influenza A strain A/Chicken/Hong Kong/31.2/2002 H5N1, Influenza A strain A/Chicken/Hong Kong/37.4/2002 H5N1, Influenza A strain A/Silky Chicken/Hong KongNU100/2002 H5N1, Influenza A strain A/Chicken/Hong Kong/96.1/2002 H5N1, Influenza A strain A/Chicken/Hong KongNU22/2002 H5N1, Influenza A strain A/Teal/China/2978.1/2002 H5N1, Influenza A strain A/Hong Kong/212/2003 H5N1, Influenza A strain A/Chicken/Shantou/4231/2003 H5N1, and Influenza A strain A/Goose/Guangxi/345/2005 H5N1. An example of a H5N2 strain is Influenza A strain A/Chicken/Pennsylvania/1370/1983 H5N2. An example of a H5N3 strain is Influenza A strain A/duck/Malaysia/F119-3/97 H5N3. An example of a H5N4 strain is Influenza A strain A/environment/New York/200269-18/2002 H5N4. An example of a H5N5 strain is Influenza A strain A/duck/Massachusetts/Sg-00440/2005 H5N5. An example of a H5N6 strain is A/duck/Potsdam/2216-4/1984 H5N6. An example of a H5N7 strain is A/mallard/Denmark/64650/03 H5N7. An example of a H5N8 strain is strain A/Duck/Ireland/113/1983 H5N8. Two examples of a H5N9 strain are Influenza A strain A/Turkey/Ontario/7732/1966 H5N9 and strain A/chicken/Italy/22AM 998 H5N9.

An example of a H6N1 strain is A/chicken/Taiwan/PF1/02(H6N1). An example of a H6N2 strain is Influenza A strain A/chicken/California/1316/2001(H6N2). An example of a H6N5 strain is Influenza A strain A/Shearwater/Australia/1972 H6N5. An example of a H6N8 strain is Influenza A strain A/Turkey/Minnesota/501/1978 H6N8. An example of a H7N1 strain is Influenza A strain A/Fowl plague virus/Rostock/8/1934 H7N1. An example of a H7N2 strain is Influenza A strain A/duck/Hong Kong/293/1978(H7N2). An example of a H7N3 strain is Influenza A strain A/Turkey/Oregon/1971 H7N3. Five examples of a H7N7 strain are Influenza A strain A/Equine/C.Detroit/1/1964 H7N7, Influenza A strain A/Equine/Cambridge/1/1973 H7N7 and Influenza A strain A/Equine/Sao Paulo/1/1976 H7N7, Influenza A virus strain A/Equine/Prague/1/1956 H7N7 and Influenza A virus strain A/Chicken/Weybridge H7N7. An example of a H8N2 strain is Influenza A strain A/duck/Alaska/702/1991 (H8N2). An example of a H8N4 strain is Influenza A strain A/Turkey/Ontario/6118/1968 H8N4. An example of a H8N4 strain is Influenza A strain A/duck/Tsukuba/255/2005 (H8N5). An example of a H8N7 strain is Influenza A strain A/duck/Alaska/702/1991(H8N7).

An example of a H9N1 strain is Influenza A virus A/Duck/Shantou/2030/00(H9N1). An example of a H9N2 strain is Influenza A virus A/Hong Kong/1073/99(H9N2) with Gene bank accession numbers NC 004905, NC 004906, NC 004907, NC 004908, NC 004909, NC 004910, NC 004911, and NC 004912. An example of a H9N3 strain is Influenza A virus A/duck/Viet Nam/340/2001 H9N3. An example of a H9N4 strain is Influenza A virus A/shorebird/DE/231/2003 H9N4. An example of a H9N5 strain is Influenza A virus A/Duck/Hong Kong/702/79 H9N5. An example of a H9N7 strain is A/turkey/Scotland/70(H9N7). An example of a H9N8 strain is A/chicken/Korea/04164/2004(H9N8). An example of a H9N9 strain is A/turkey/France/03295/2003 H9N9. An example of a H10N1 strain is Influenza A virus A/duck/Hong Kong/938/80 H10N1. An example of a H10N2 strain is Influenza A virus A/duck/Alaska/658/1991 H10N2. An example of a H10N5 strain is Influenza A virus A/duck/Hong Kong/15/1976 H10N5. Examples of a H10N7 strain are Influenza A strain A/Chicken/Germany/n/1949 H10N7, strain A/Duck/Germany/1949 H10N7, and strain A/Duck/Manitoba/1/1953 H10N7. An example of a H10N7 strain is Influenza A virus strain A/Duck/Germany/1949 H10N7. An example of a H11N1 strain is Influenza A virus strain A/duck/Miyagi/47/1977 H11N1. An example of a H11N2 strain is A/duck/Yangzhou/906/2002 H11N2. An example of a H11N3 strain is A/duck/Thailand/CU5388/2009 H11N3. An example of a H11N6 strain is Influenza A virus strain A/Duck/England/i/1956 H11N6. An example of a H11N8 strain is strain A/Duck/Ukraine/2/1960 H11N8. Two examples of a H11N9 strain are Influenza A strain A/Duck/Ukraine/i/1960 H11N9 and Influenza A strain A/Tern/Australia/G70C/1975 H11N9. An example of a H12N1 strain is A/mallard duck/Alberta/342/1983(H12N1). An example of a H12N2 strain is A/duck/Primorie/3691/02 H12N2. An example of a H12N3 strain is A/whooper swan/Mongolia/232/2005 H12N3. An example of a H12N5 strain is Influenza A virus strain A/Duck/Alberta/60/1976 H12N5. An example of a H12N6 strain is A/mallard/Alberta/221/2006 H12N6. An example of a H12N7 strain is A/duck/Victoria/30a/1981 H12N7. An example of a H12N8 strain is A/mallard/Netherlands/20/2005 H12N8. An example of a H12N9 strain is A/red-necked stint/Australia/5745/1981 H12N9.

An example of a H13N1 strain is A/bird feces/Illinois/185997-30/2007 H13N1. An example of a H13N2 strain is Influenza A virus strain A/Whale/Maine/328/1984 H13N2. An example of a H13N3 strain is A/shorebird/NJ/840/1986 H13N3. Two examples of a H13N6 strain are Influenza A virus strain A/Gull/Maryland/704/1977 H13N6 and strain A/Gull/Minnesota/945/1980 H13N6. An example of a H13N8 strain is A/black-headed gull/Sweden/i/2005 H13N8. An example of a H14N3 strain is A/mallard/Gur/263/82 H14N3. Three examples of a H14N5 strain are A/mallard/Gurjev/263/1982 H14N5, A/mallard/Astrakhan/266/1982 H14N5 and A/herring gull/Astrakhan/267/1982 H14N5. An example of a H14N6 strain is strain A/Mallard/Gurjev/244/1982 H14N6. An example of a H15N8 strain is A/duck/Australia/341/1983 H15N8. An example of a H15N9 strain is A/shearwater/West Australia/2576/79 H15N9. An example of a H16N3 strain is A/black-headed gull/Sweden/2/99 H16N3.

Such virus subtypes are distinguishable serologically, which means that antibodies specific for one subtype do not bind to another subtype with comparable high affinity. Nevertheless the nucleic acid positions characterizing the genes of an Influenza A virus according to the present invention apply to any Influenza A virus strain.

ii. Influenza Type B

The live-attenuated virus described herein can also be influenza type B virus. The live-attenuated influenza type B virus, including live-attenuated influenza type B virus in a pharmaceutical composition, can be based on any influenza B virus strain. Suitable virus strains include, but are not limited to Influenza B virus strain B/Maryland/1959, strain B/Yamagata/1/1973, strain B/Victoria/3/1985, strain B/USSR/100/1983, strain B/Tokyo/942/1996, strain B/Texas/4/1990, strain B/Singapore/222/1979, strain B/South Dakota/5/1989, strain B/Paris/329/1990, strain B/Leningrad/179/1986, strain B/Hong Kong/8/1973, strain B/Fukuoka/80/1981, strain B/Bangkok/163/1990, strain B/Beijing/1/1987, strain B/Switzerland/9359/99, strain B/Wisconsin/6/2006, strain B/West Virginia/01/2009, strain B/Washington/08/2009, strain B/Uruguay/NG/02, strain B/Texas/18/2001, strain B/Taiwan/S117/2005, strain B/Taiwan/3799/2006, strain B/Spain/WV45/2002, strain B/Seoul/232/2004, strain B/Rio Grande do Sul/57/2008, strain B/Quebec/517/98, strain B/Philippines/5072/2001, strain B/Oslo/1871/2002, strain B/Osaka/983/1997, strain B/Milan/05/2006, strain B/Johannesburg/116/01 or strain B/Arizona/12/2003.

B. Attenuation

When the disclosed virus is to be used as or in a vaccine, it is useful to attenuate the virus. This is because the virus will be designed and expected to infect host cells, replicate, and produce viral proteins but to not cause the disease. An attenuated virus is a virus created by reducing the virulence of the virus, but still keeping it viable (or "live") (Badgett et al., J. Virol. 76(20):10524-10529 (2002)). Attenuation takes the virus and alters it so that it becomes harmless or less virulent. These viruses contrast to those produced by "killing" the virus (inactivated vaccine).

There are a number of approaches to attenuate viruses. Each has useful elements, but most approach has some limitations in their use or usefulness. Examples of forms of attenuation include serial passage in cultured cells, serial passage in a heterologous host animal, gene deletion in the virus, site-directed mutagenesis of the virus, altering codon usage of the virus, selection of cold-adapted mutants, using a related virus from a heterologous host species, using a naturally occurring attenuated virus strain, or combinations thereof. In some forms, the virus is attenuated by serial passage in cultured cells, wherein the cultured cells are Madin-Darby Canine Kidney (MDCK) cells. Classes of attenuation include empirically attenuated virus, replication defective virus, single cycle virus, replication fidelity attenuated virus, codon deoptimized virus, miRNA-controlled virus, and Zinc finger nuclease (ZFN)-controlled virus.

Empirically attenuated virus is typically produced by blind passage in different cell types. By adapting to a new environment, the virus accumulates mutations that mediate attenuation. Host immunity is able to limit that virulence and spread of the attenuated virus. Empirically attenuated virus has excellent immunogenicity, with few doses required. Only some viruses can be empirically attenuated and empirically attenuated virus is prone to reversion to wild type and breakthrough disease.

Replication defective virus is typically produced by deleting one or several genes required for genome replication from the virus. The virus vaccine can then be produced in a helper cell line that expresses the missing protein(s) in trans (Dudek and Knipe, Virology 344:230-239 (2006)). The administered virus is unable to replicate its genome. Replication defective virus typically provides good immunogenicity, with a known mechanism of attenuation. Effectiveness of replication defective virus might be limited because replication in the host is limited to the inoculation site.

Single cycle virus is typically produced by deleting one or several genes required for viral assembly and spread from the virus. Single cycle virus is distinguished from replication defective viruses by their competence for genome replication (Loudon et al., J Gene Med. 3:458-467 (2001)). Single cycle virus is able to replicate its genome, but is defective for assembly or spread. Single cycle virus typically provides good immunogenicity, with a known mechanism of attenuation. Effectiveness of replication defective virus might be limited because replication in the host is limited to the inoculation site.

Replication fidelity attenuated virus is typically produced by engineering or selecting virus resistant to nucleoside analogues. The resistant virus has higher replication fidelity, which results in virus progeny with less diversity, which results in attenuation (e.g., host is more effective in attacking virus) (Vignuzzi et al., Nature 439:344-348 (2006); Pfeiffer and Kirkegaard, PLoS Pathog. 1:e11 (2005)). Replication fidelity attenuated virus typically provides strong immunogenicity, with a known mechanism of attenuation, and is not susceptible to antigenic shift/drift. Replication fidelity attenuated virus is limited to RNA viruses only. Reversion to wildtype is possible. Safety of virus with higher replication fidelity is not yet clearly established.

Codon deoptimized virus is typically produced by changing codons in the virus to synonymous codons that are less favored in the host (Baker et al., Future Virology 10(6):715-730 (2015)). Loss of expression efficiency of codon deoptimized virus leads to lower viral production. Codon deoptimized virus typically provides strong immunogenicity, no reversion to wild type, and is applicable to many viruses. Possible safety concerns. Safety of codon deoptimized virus is not yet clearly established.

miRNA-controlled virus is typically produced by adding miRNA sequences in the virus (Fay and Langlois, Non-Coding RNA 4(4):25 (2018)). The miRNA sequences are chosen to limit in which cells of host the virus can replicate (e.g., altered tropism). miRNA-controlled virus can provide strong immunogenicity, with a known mechanism of attenuation, and can prevent latent infection. miRNA-controlled virus is limited to some RNA viruses. Safety of miRNA-controlled virus is not yet clearly established.

Zinc finger nuclease (ZFN)-controlled virus is typically produced by introducing sequences encoding ZFNs that target sequences in the virus for viral replication and other essential viral processes. Following inoculation, both immunogenic viral genes and virus-specific ZFNs would be expressed. While the viral proteins would stimulate a natural immune response, the ZFNs would cleave viral DNA, and limit replication. ZFN-controlled virus produce strong immunogenicity, with a known mechanism of attenuation, and can prevent latent infection. ZFN-controlled virus are limited to non-integrating DNA viruses. Safety of ZFN-controlled virus is not yet clearly established.

C. Vaccines

One composition disclosed herein is a vaccine. The vaccine can contain nucleic acids, amino acids or a combination thereof. A vaccine (or an immunogenic composition) including an immunogenic amount (preferably an effective or protective amount) of a composition, such as an outer membrane protein, (either isolated or purified, or present in an outer membrane vesicle, ghost or killed, live, or live-attenuated whole cell preparation) in a pharmaceutically acceptable excipient, and an optional adjuvant. In this context, immunogenic amount can be defined as a sufficient quantity of protein to elicit an antibody response in a host. A preferred vaccine is a vaccine that includes and/or is produced by the disclosed viruses.

An immunogenic amount of one of the disclosed compositions can be formulated in a pharmaceutically acceptable excipient, and an optional adjuvant, to prevent or treat infectious diseases. Vaccines can be used to induce an immune response in a mammal susceptible to infection by a pathogen by administering to the mammal an effective amount of the vaccine (an effective amount being an amount capable of protecting a host to some degree against an infection). A vaccine can also prevent an infection by administration to a mammal in an effective amount.

Vaccines are capable of eliciting a cross-protective immune response against a large variety of viruses.

The vaccines described herein are typically generated based on fundamental information about the pathogen, such as how it infects cells and how the immune system responds to it, as well as practical considerations, such as regions of the world where the vaccine is to be used. The vaccines described herein can be, for example, live, attenuated vaccines; inactivated vaccines; subunit vaccines; toxoid vaccines; conjugate vaccines; DNA vaccines; or recombinant vector vaccines.

Generally, the live-attenuated viruses described herein can be used in live, attenuated vaccines. An exemplary vaccine includes a live-attenuated influenza virus vaccine that can effectively protect a host against influenza by immunization with a single effective dose.

Vaccines can elicit a humoral response, cell-mediated immune response or a combination thereof. Ideally, the immune response provides protection upon subsequent challenge with the unattenuated virus of the same or a different subtype or strain. The live-attenuated viruses described herein, when used as vaccines, can provide homosubtypic immune protection, heterosubtypic immune protection, or both.

i. Live-Attenuated Vaccines

Live, attenuated vaccines contain a version of the living virus that has been weakened in the lab so it can't cause disease. Because a live, attenuated vaccine is the closest thing to a natural infection, these vaccines are good "teachers" of the immune system: They elicit strong cellular and antibody responses and often confer lifelong immunity with only one or two doses.

Despite the advantages of live, attenuated vaccines, there are some downsides. It is the nature of living things to change, or mutate, and the organisms used in live, attenuated vaccines are no different. The remote possibility exists that an attenuated virus in the vaccine could revert to a virulent form and cause disease. However, this possibility is significantly reduced by the introduction of a large number of mutations within a viral genome. Also, not everyone can safely receive live, attenuated vaccines. For their own protection, people who have damaged or weakened immune systems-because they've undergone chemotherapy or have HIV, for example—cannot be given live vaccines.

Another limitation is that live, attenuated vaccines usually need to be refrigerated to stay potent. If the vaccine needs to be shipped overseas and stored by healthcare workers in developing countries that lack widespread refrigeration, a live vaccine may not be the best choice.

ii. Inactivated Vaccines

Inactivated vaccines are produced by killing the disease-causing pathogen with chemicals, heat, or radiation. Such vaccines are more stable and safer than live vaccines: The dead pathogen can't mutate back to their disease-causing state. Inactivated vaccines usually don't require refrigeration, and they can be easily stored and transported in a freeze-dried form, which makes them accessible to people in developing countries.

Most inactivated vaccines, however, stimulate a weaker immune system response than do live vaccines. So it would likely take several additional doses, or booster shots, to maintain a person's immunity. This could be a drawback in areas where people don't have regular access to health care and can't get booster shots on time.

iii. Subunit Vaccines

Instead of the entire pathogen, subunit vaccines include only the antigens that best stimulate the immune system. In some cases, these vaccines use epitopes—the very specific parts of the antigen that antibodies or T cells recognize and bind to. Because subunit vaccines contain only the essential antigens and not all the other molecules that make up the microbe, the chances of adverse reactions to the vaccine are lower.

Subunit vaccines can contain 1 antigen, 20 antigens, any number of antigens between 1 to 20 antigens, or more than 20 antigens. Once the antigens that can best stimulate the immune system are identified, they can be made into subunit vaccines in one of two ways: 1) the pathogens are grown in the laboratory and then chemicals are used to break them apart and gather the important antigens; or 2) the antigens can be manufactured using recombinant DNA technology. Vaccines produced this way are called "recombinant subunit vaccines."

iv. Toxoid Vaccines

The toxoid vaccines are useful for pathogens that secrete toxins. These vaccines are used when a pathogen's toxin is the main cause of illness. The toxins are usually inactivated by treating them with formalin, a solution of formaldehyde and sterilized water. Such "detoxified" toxins, called toxoids, are safe for use in vaccines.

When the immune system receives a vaccine containing a harmless toxoid, it learns how to fight off the natural toxin. The immune system produces antibodies that lock onto and block the toxin. Vaccines against diphtheria and tetanus are examples of toxoid vaccines.

v. Conjugate Vaccines

Conjugate vaccines are usually made when the pathogen possesses an outer coating of polysaccharides, as many harmful bacteria do. Polysaccharide coatings disguise bacterium's antigens so that the immature immune systems of infants and younger children can't recognize or respond to them. Conjugate vaccines, a special type of subunit vaccine, get around this problem.

When making a conjugate vaccine, the antigens or toxoids from a pathogen that an infant's immune system can recognize are usually linked to the polysaccharides. The linkage helps the immature immune system react to polysaccharide coatings and defend against the disease-causing bacterium.

vi. DNA Vaccines

DNA vaccines use the genes of the pathogen that code for immunogenic antigens. It was found that when the genes for a pathogen's antigens are introduced into the body, some cells take up that DNA. The DNA then instructs those cells to make the antigen molecules. The cells secrete the antigens and display them on their surfaces. A DNA vaccine against a pathogen would evoke a strong antibody response to the free-floating antigen secreted by cells, and the vaccine also would stimulate a strong cellular response against the microbial antigens displayed on cell surfaces. In addition, DNA vaccines are relatively easy and inexpensive to design and produce.

So-called naked DNA vaccines consist of DNA that is administered directly into the body. These vaccines can be administered with a needle and syringe or with a needle-less device that uses high-pressure gas to shoot microscopic gold particles coated with DNA directly into cells. Sometimes, the DNA is mixed with molecules that facilitate its uptake by the cells.

vii. Recombinant Vector Vaccines

The recombinant vector vaccines are similar to DNA vaccines, but they use an attenuated virus or bacterium to introduce microbial DNA to cells of the body. "Vector" refers to the virus or bacterium used as the carrier. The carrier viruses ferry pathogen's DNA to cells. Recombinant vector vaccines closely mimic a natural infection and therefore stimulating the immune system.

Attenuated bacteria also can be used as vectors. In this case, the inserted genetic material causes the bacteria to display the antigens of other microbes on its surface. In effect, the harmless bacterium mimics a harmful microbe, provoking an immune response.

1. Carriers

Pharmaceutical compositions can be formulated in a conventional manner using one or more physiologically acceptable carriers including excipients and auxiliaries which facilitate processing of the active compounds into preparations which can be used pharmaceutically. Proper formulation is dependent upon the route of administration chosen. In one form, administration is through upper or lower airway mucosa by inhalation. Typical formulations include a carrier such as sterile saline or a phosphate buffered saline. Viscosity modifying agents and preservatives are also frequently added.

Optional pharmaceutically acceptable excipients especially for enteral, topical and mucosal administration, include, but are not limited to, diluents, binders, lubricants, disintegrants, colorants, stabilizers, and surfactants. Diluents, also referred to as "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (POLYPLASDONE® XL from GAF Chemical Corp).

Stabilizers are used to inhibit or retard decomposition reactions which include, by way of example, oxidative reactions.

Surfactants can be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-b-alanine, sodium N-lauryl-b-iminodipropionate, myristoamphoacetate, lauryl betaine and lauryl sulfobetaine.

If desired, the compositions can also contain minor amount of nontoxic auxiliary substances such as wetting or emulsifying agents, dyes, pH buffering agents, or preservatives.

2. Adjuvants

In one form the adjuvant is the synthetic glycolipid alpha-galactosylceramide (αGalCer). Dendritic cells presenting antigens in the context of CD1d can lead to rapid innate and prolonged production of cytokines such as interferon and IL-4 by natural killer T cells (NKT cells). CD1d is a major histocompatibility complex class I-like molecule that presents glycolipid antigens to a subset of NKT cells. Advantageously, αGalCer is not toxic to humans and has been shown to act as an adjuvant, priming both antigen-specific CD4+ and CD8$^+$ T cell responses. For example, it has been shown that αGalCer in conjunction with a malaria vaccine can lead to cytotoxic responses against infected cells, which is an ideal scenario for vaccines against infectious diseases. In addition to αGalCer, other glycolipids that function as adjuvants to activate NKT cell-mediated immune responses can be used.

In another form the adjuvant can be, but is not limited to, one or more of the following: oil emulsions (e.g., Freund's adjuvant); saponin formulations; virosomes and viral-like particles; bacterial and microbial derivatives including, but not limited to carbohydrates such as lipopolysachharide (LPS); immunostimulatory oligonucleotides; ADP-ribosylating toxins and detoxified derivatives; alum; BCG; mineral-containing compositions (e.g., mineral salts, such as aluminum salts and calcium salts, hydroxides, phosphates, sulfates, etc.); bioadhesives, mucoadhesives, or both; microparticles; liposomes; polyoxyethylene ether and polyoxyethylene ester formulations; polyphosphazene; muramyl peptides; imidazoquinolone compounds; and surface active substances (e.g. lysolecithin, pluronic polyols, polyanions, peptides, oil emulsions, keyhole limpet hemocyanin, and dinitrophenol).

Adjuvants can also include immunomodulators such as cytokines, interleukins (e.g., IL-1, IL-2, IL-4, IL-5, IL-6, IL-7, IL-12, etc.), interferons (e.g., interferon-.gamma.), macrophage colony stimulating factor, and tumor necrosis factor; and co-stimulatory molecules, such as those of the B7 family. Such proteinaceous adjuvants can be provided as the full-length polypeptide or an active fragment thereof, or in the form of DNA, such as plasmid DNA.

D. Kits

Also provided is a kit or kits for immunization of a subject with a live attenuated virus described herein. The kit can comprises, for example, the live attenuated virus, a pharmaceutically acceptable carrier, an adjuvant, an applicator, and an instructional material for the use thereof. In further forms, the live-attenuated virus can be one or more poliovirus, one or more rhinovirus, one or more influenza virus, etc. More than one virus may be preferred where it is desirable to immunize a host against a number of different isolates of a particular virus. The instructions can provide any information that is useful for directing the administration of the live attenuated viruses.

Methods

Disclosed are methods of making and using viruses and vaccines as disclosed.

A. Methods of Making Viruses

Methods of making recombinant viruses with segmented or singular genomes are generally known in the art. These include methods with standard reverse genetic techniques and genomic manipulation in molecular biology (Hoffmann et al., *Proc. Natl. Acad. Sci. USA*, 97(11):6108-6113 (2000);

Zhou et al., *J. Virol.*, 72(4):3241-3247 (1998)). All the synthetic genes are usually subcloned into expression constructs. The constructs are then used to contact, i.e., infect, the same host cell in vitro. The host cell then produces the packaged viruses containing the manipulated genome. The packaged viruses are then harvested and their titer determined using standard virology techniques, and used for further characterization.

Methods of quantifying viral particles are known in the art. Examples include plaque-based assays for determining virus concentration in terms of infectious dose. Viral plaque assays determine the number of plaque forming units (pfu) in a virus sample, which is one measure of virus quantity. The focus forming assay (FFA) is a variation of the plaque assay, but instead of relying on cell lysis in order to detect plaque formation, the FFA employs immunostaining techniques using fluorescently labeled antibodies specific for a viral antigen to detect infected host cells and infectious virus particles before an actual plaque is formed. The FFA is particularly useful for quantifying classes of viruses that do not lyse the cell membranes, as these viruses would not be amenable to the plaque assay. Another assay is Endpoint Dilution Assay (50% Tissue Culture Infective Dose (TCID$_{50}$)). TCID$_{50}$ is the measure of infectious virus titer. This endpoint dilution assay quantifies the amount of virus required to kill 50% of infected hosts or to produce a cytopathic effect in 50% of inoculated tissue culture cells.

Viral proteins of viruses can be isolated or purified from viruses produced as described herein. Method of doing so are generally known.

B. Administration of Viruses and Vaccines

The disclosed viruses can be used for the prophylactic treatment of viral infections, therapeutic treatment of viral infections, or both; that is, it can be used for the treatment of viral infections, prevention of viral infections, or both. The viruses can be administered as a pharmaceutical composition through any route that is known in the art. Generally, the pharmaceutical compositions can be administered, for example, intravenously, subcutaneously, intramuscularly or, intranasally. For such purposes, the virus of the pharmaceutical composition can be provided in a suitable injectable or inhalable form. A live-attenuated virus of the present disclosure can, in some forms, be included in a device for applying the virus in an inhalable or injectable form to a subject.

A pharmaceutical composition that includes a virus of the present disclosure can be manufactured in a manner that is itself known, e.g., by means of conventional mixing, dissolving, granulating, dragée-making, levigating, emulsifying, encapsulating, entrapping or lyophilising processes. The composition can be an immunogenic composition such as a vaccine. The respective vaccine forming the main constituent of the vaccine composition of the disclosure can include a single antigen, a combination of antigens, a single virus, or a combination of viruses—for example, at least two or three viruses of the same species, including one or more reassortant(s).

Certain forms of any of the instant immunization and therapeutic methods further comprise administering to the subject at least one adjuvant. Numerous adjuvants, including particulate adjuvants, suitable for use with both protein- and nucleic acid-based vaccines, and methods of combining adjuvants with antigens, are well known to those skilled in the art. Suitable adjuvants for nucleic acid based vaccines include, but are not limited to, Quil A, imiquimod, resiquimod, and interleukin-12 delivered in purified protein or nucleic acid form. Adjuvants suitable for use with protein immunization include, but are not limited to, alum, Freund's incomplete adjuvant (FIA), saponin, Quil A, and QS-21.

Exemplary routes of administration of a pharmaceutical composition of the disclosure include oral, transdermal, and parenteral delivery. Suitable routes of administration can, for example, include depot, oral, rectal, transmucosal, or intestinal administration; parenteral delivery, including intramuscular, subcutaneous, intravenous, intramedullary injections, as well as intrathecal, direct intraventricular, intraperitoneal, intranasal, or intraocular injections.

As an illustrative example, for injection, a pharmaceutical composition according to the present disclosure can be formulated as an aqueous solution, for example in physiologically compatible buffers such as Hanks's solution, Ringer's solution, or physiological saline buffer. For oral administration, a respective pharmaceutical composition can be formulated readily by combining the virus with pharmaceutically acceptable carriers well known in the art. Such carriers enable a virus of the invention to be formulated as tablets, pills, lozenges, dragées, capsules, liquids, gels, syrups, slurries, suspensions and the like, for oral ingestion by a patient to be treated.

Pharmaceutical preparations for oral use can be obtained by adding a solid excipient, optionally grinding a resulting mixture, and processing the mixture of granules, after adding suitable auxiliaries, if desired, to obtain tablets or dragée cores. Suitable excipients are, in particular, fillers such as sugars, including lactose, glucose, sucrose, mannitol, or sorbitol; starches and derivatives thereof, such as, corn starch, dextrin and wheat starch, rice starch, potato starch, hydroxypropyl starch, wheat starch, gelatine, gum tragacanth, methyl cellulose, hydroxypropylmethyl-cellulose, sodium carboxymethylcellulose, polyvinylpyrrolidone (PVP), or combinations thereof; cellulose preparations such as, for example, methylcellulose, carboxylmethylcellulose and hydroxypropylcellulose; inorganic compounds, such as sodium chloride, boric acid, calcium sulfate, calcium phosphate and precipitated calcium carbonate. If desired, disintegrating agents can be added, such as the cross-linked polyvinyl pyrrolidone, agar, or alginic acid or a salt thereof such as sodium alginate.

Dragée cores are provided with suitable coatings. For this purpose, concentrated sugar solutions can be used which may optionally contain gum arabic, talc, polyvinyl pyrrolidone, carbopol gel, polyethylene glycol, titanium dioxide, or combinations thereof, lacquer solutions; and suitable organic solvents or solvent mixtures. Dyestuffs or pigments can be added to the tablets or dragée coatings for identification or to characterize different combinations of virus doses. Suitable fluidizing agents include, but are not limited to, magnesium oxide, synthetic aluminium silicate, metasilicic acid, magnesium aluminium oxide, hydrous silicic acid, anhydrous silicic acid, talc, magnesium stearate, and kaolin. Suitable binding agents include, but are not limited to, polyethylene glycol, polyvinyl pyrrolidine, polyvinyl alcohol, gum arabic, tragacanth, sodium alginate, gelatine, and gluten. Suitable stabilisers include, but are not limited to, proteins, such as albumin, protamine, gelatine and globulin; and amino acids and salts thereof. Suitable thickeners include, but are not limited to, sucrose, glycerine, methylcellulose, and carboxymethylcellulose. Suitable pH adjusting agents include, but are not limited to, hydrochloric acid, sodium hydroxide, phosphates, citrates, and carbonates.

Pharmaceutical compositions that can be used orally include, but are not limited to, push-fit capsules made of gelatine, as well as soft, sealed capsules made of gelatine and a plasticiser, such as glycerol or sorbitol. The push-fit capsules can contain the live-attenuated virus in admixture with filler such as lactose, binders such as starches, lubricants (such as talc or magnesium stearate), or both, and, optionally, stabilizers. In soft capsules, the virus(es) can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, a respective pharmaceutical composition can take the form of tablets or lozenges formulated in conventional manner.

For administration by inhalation, a pharmaceutical composition for use according to the present disclosure may conveniently be delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges of, for example, gelatin, for use in an inhaler or insufflator can be formulated containing a powder mix of the virus and a suitable powder base such as lactose or starch.

A respective pharmaceutical composition can be formulated for parenteral administration by injection, e.g., by bolus injection or continuous infusion. Formulations for injection can be presented in unit dosage form, e.g., in ampules or in multi-dose containers, with an added preservative. The compositions can take such forms as suspensions, solutions or emulsions in oily or aqueous vehicles, and can contain formulatory agents such as suspending agents, stabilizing agents, dispersing agents, or combinations thereof.

Pharmaceutical formulations for parenteral administration include aqueous solutions of the virus in water-soluble form. Additionally, suspensions of the virus can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances that increase the viscosity of the suspension, such as sodium carboxymethyl cellulose, sorbitol, or dextran.

In some forms an active ingredient, such as a virus as described herein, can be in powder form for constitution with a suitable vehicle, e.g., sterile pyrogen-free (SPF) water, before use.

Examples of suitable mammals include, but are not limited to, a mouse, a rat, a cow, a goat, a sheep, a pig, a dog, a cat, a horse, a guinea pig, a canine, a hamster, a mink, a seal, a whale, a camel, a chimpanzee, a rhesus monkey and a human.

Dosages and desired concentrations of the attenuated viruses of the present disclosure can vary depending on the particular use envisioned. The determination of the appropriate dosage or route of administration is well within the skill of an ordinary physician. Animal experiments provide reliable guidance for the determination of effective doses for human prophylactic and therapeutic use. Interspecies scaling of effective doses can be performed following the principles laid down by Mordenti, J. and Chappell, W. "The use of interspecies scaling in toxicokinetics" In Toxicokinetics and New Drug Development, Yacobi et al., Eds., Pergamon Press, New York 1989, pp. 42-96.

The amount or dose of the material administered should be sufficient to affect a therapeutic or prophylactic response in a subject over a reasonable time frame. For example, the dose of the material should be sufficient to prevent a symptomatic infection by the unattenuated wild type virus. The dose should be sufficient to stimulate the immune response, to treat or prevent wild type virus infections, or both.

Many assays for determining an administered dose are known in the art. For purposes of the present methods, an assay which includes comparing the anti-viral antibodies and immune cell types present in response to several different doses of the attenuated virus administered to a set of mammals can be performed. The dose also can be determined by the existence, nature and extent of any adverse side effects that might accompany the administration. A variety of factors, such as age, body weight, general health, diet, sex, material to be administered, route of administration, and the severity of the condition being treated can be considered when determining dosage.

The dosage of a live-attenuated virus vaccine for a subject such as a mammalian adult organism can be from about $10^2$ to about $10^{15}$, e.g., about $10^3$ to about $10^{12}$, about $10^3$ to about $10^{10}$, about $10^3$ to about $10^8$, about $10^5$ to about $10^8$, about $10^3$ to about $10^6$, about $10^4$ to about $10^8$, about $10^4$ to about $10^7$, about $10^4$ to about $10^6$ or about $10^4$ to about $10^5$ plaque forming units (PFU)/kg, or any range or value therein. However, the dosage should be a safe and effective amount as determined by conventional methods, using existing vaccines as a starting point.

A pharmaceutical composition for use in accordance with the present disclosure can be formulated in conventional manner using one or more pharmacologically acceptable carriers that include excipients and auxiliaries, which facilitate processing of the virus into preparations that can be used pharmaceutically. Proper formulation is dependent upon the selected route of administration. A composition, including its components, is said to be "pharmacologically acceptable" if its administration can be tolerated by a recipient subject. Such an agent is said to be administered in a "therapeutically effective amount" if the amount administered is physiologically significant. A composition of the present disclosure is physiologically significant if its presence results in a detectable change in the physiology of a recipient subject, e.g., enhances at least one primary or secondary humoral or cellular immune response against at least one strain of an infectious virus.

In some forms, the effective dose of the live-attenuated viruses and pharmaceutical compositions described herein can generally include about $10^2$ p.f.u., $10^3$ p.f.u., $10^4$ p.f.u., $10^5$ p.f.u., $10^6$ p.f.u., $10^7$ p.f.u., $10^8$ p.f.u., $10^9$ p.f.u., or more per dose per administration. The rate of administration can vary. Generally, the rate of administration can be, for example, from once a month, once every three months, once every six months, annually, or as needed for buster vaccinations.

As used herein, an "immunogen" or "immunogenic amount" refers to the ability of a substance (antigen) to induce an immune response. An immune response is an alteration in the reactivity of an organism's immune system in response to an antigen, in vertebrates, this may involve antibody production, induction of cell-mediated immunity, complement activation or development of immunological tolerance.

As used herein, an "adjuvant" is a substance that increases the ability of an antigen to stimulate the immune system.

As used herein, "attenuation" refers to refers to procedures that weaken an agent of disease (a pathogen). The term "attenuated" in the context of such an agent of disease refers to such an agent of disease that has been weakened. For example, an attenuated virus is a weakened, less vigorous virus. A vaccine against a viral disease can be made from an attenuated, less virulent strain of the virus, a virus capable of stimulating an immune response and creating immunity but not causing illness or less severe illness. Attenuation can be achieved by chemical treatment of the pathogen, through radiation, or by genetic modification, using methods known to those skilled in the art. Attenuation may result in decreased proliferation, attachment to host cells, or decreased production or strength of toxins.

The term "in need of treatment" as used herein refers to a judgment made by a caregiver (e.g. physician, nurse, nurse practitioner, or individual in the case of humans; veterinarian in the case of animals, including non-human mammals) that a subject requires or will benefit from treatment. This judgment is made based on a variety of factors that are in the realm of a care giver's expertise, but that include the knowledge that the subject is ill, or will be ill, as the result of a condition that is treatable by the disclosed compounds.

As used herein, "subject" includes, but is not limited to, animals, plants, bacteria, viruses, parasites and any other organism or entity. The subject can be a vertebrate, more specifically a mammal (e.g., a human, horse, pig, rabbit, dog, sheep, goat, non-human primate, cow, cat, guinea pig or rodent), a fish, a bird or a reptile or an amphibian. The subject can be an invertebrate, more specifically an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

By "treatment" and "treating" is meant the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. It is understood that treatment, while intended to cure, ameliorate, stabilize, or prevent a disease, pathological condition, or disorder, need not actually result in the cure, amelioration, stabilization or prevention. The effects of treatment can be measured or assessed as described herein and as known in the art as is suitable for the disease, pathological condition, or disorder involved. Such measurements and assessments can be made in qualitative and/or quantitative terms. Thus, for example, characteristics or features of a disease, pathological condition, or disorder and/or symptoms of a disease, pathological condition, or disorder can be reduced to any effect or to any amount.

A cell can be in vitro. Alternatively, a cell can be in vivo and can be found in a subject. A "cell" can be a cell from any organism including, but not limited to, a bacterium.

In one aspect, the compounds described herein can be administered to a subject comprising a human or an animal including, but not limited to, a mouse, dog, cat, horse, bovine or ovine and the like, that is in need of alleviation or amelioration from a recognized medical condition.

By the term "effective amount" of a compound as provided herein is meant a nontoxic but sufficient amount of the compound to provide the desired result. As will be pointed out below, the exact amount required will vary from subject to subject, depending on the species, age, and general condition of the subject, the severity of the disease that is being treated, the particular compound used, its mode of administration, and the like. Thus, it is not possible to specify an exact "effective amount." However, an appropriate effective amount can be determined by one of ordinary skill in the art using only routine experimentation.

The dosages or amounts of the compounds described herein are large enough to produce the desired effect in the method by which delivery occurs. The dosage should not be so large as to cause adverse side effects, such as unwanted cross-reactions, anaphylactic reactions, and the like. Generally, the dosage will vary with the age, condition, sex and extent of the disease in the subject and can be determined by one of skill in the art. The dosage can be adjusted by the individual physician based on the clinical condition of the subject involved. The dose, schedule of doses and route of administration can be varied.

The efficacy of administration of a particular dose of the compounds or compositions according to the methods described herein can be determined by evaluating the particular aspects of the medical history, signs, symptoms, and objective laboratory tests that are known to be useful in evaluating the status of a subject. These signs, symptoms, and objective laboratory tests will vary, depending upon the particular disease or condition being treated or prevented, as will be known to any clinician who treats such patients or a researcher conducting experimentation in this field. For example, if, based on a comparison with an appropriate control group and/or knowledge of the normal progression of the disease in the general population or the particular individual: (1) a subject's physical condition is shown to be improved (e.g., a tumor has partially or fully regressed), (2) the progression of the disease or condition is shown to be stabilized, or slowed, or reversed, or (3) the need for other medications for treating the disease or condition is lessened or obviated, then a particular treatment regimen will be considered efficacious.

By "pharmaceutically acceptable" is meant a material that is not biologically or otherwise undesirable, i.e., the material can be administered to a subject along with the selected compound without causing any undesirable biological effects or interacting in a deleterious manner with any of the other components of the pharmaceutical composition in which it is contained.

Any of the compounds having the formula I can be used therapeutically in combination with a pharmaceutically acceptable carrier. The compounds described herein can be conveniently formulated into pharmaceutical compositions composed of one or more of the compounds in association with a pharmaceutically acceptable carrier. See, e.g., *Remington's Pharmaceutical Sciences*, latest edition, by E.W. Martin Mack Pub. Co., Easton, PA, which discloses typical carriers and conventional methods of preparing pharmaceutical compositions that can be used in conjunction with the preparation of formulations of the compounds described herein and which is incorporated by reference herein. These most typically would be standard carriers for administration of compositions to humans. In one aspect, humans and non-humans, including solutions such as sterile water, saline, and buffered solutions at physiological pH. Other compounds will be administered according to standard procedures used by those skilled in the art.

The pharmaceutical compositions described herein can include, but are not limited to, carriers, thickeners, diluents, buffers, preservatives, surface active agents and the like in addition to the molecule of choice. Pharmaceutical compositions can also include one or more active ingredients such as antimicrobial agents, antiinflammatory agents, anesthetics, and the like.

The compounds and pharmaceutical compositions described herein can be administered to the subject in a number of ways depending on whether local or systemic treatment is desired, and on the area to be treated. Thus, for example, a compound or pharmaceutical composition described herein can be administered as an ophthalmic solution and/or ointment to the surface of the eye. Moreover, a compound or pharmaceutical composition can be administered to a subject vaginally, rectally, intranasally, orally, by inhalation, or parenterally, for example, by intradermal, subcutaneous, intramuscular, intraperitoneal, intrarectal, intraarterial, intralymphatic, intravenous, intrathecal and intratracheal routes. Parenteral administration, if used, is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

Preparations for parenteral administration include sterile aqueous or non-aqueous solutions, suspensions, and emulsions which can also contain buffers, diluents and other suitable additives. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like can be necessary or desirable.

Compositions for oral administration can include powders or granules, suspensions or solutions in water or non-aqueous media, capsules, sachets, or tablets. Thickeners, flavorings, diluents, emulsifiers, dispersing aids or binders can be desirable.

The terms "high," "higher," "increases," "elevates," or "elevation" refer to increases above basal levels, e.g., as compared to a control. The terms "low," "lower," "reduces," or "reduction" refer to decreases below basal levels, e.g., as compared to a control.

The term "modulate" as used herein refers to the ability of a compound to change an activity in some measurable way as compared to an appropriate control. As a result of the presence of compounds in the assays, activities can increase or decrease as compared to controls in the absence of these compounds. Preferably, an increase in activity is at least 25%, more preferably at least 50%, most preferably at least 100% compared to the level of activity in the absence of the compound. Similarly, a decrease in activity is preferably at least 25%, more preferably at least 50%, most preferably at least 100% compared to the level of activity in the absence of the compound. A compound that increases a known activity is an "agonist." One that decreases, or prevents, a known activity is an "antagonist."

The term "inhibit" means to reduce or decrease in activity or expression. This can be a complete inhibition of activity or expression, or a partial inhibition. Inhibition can be compared to a control or to a standard level. Inhibition can be 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%.

The term "monitoring" as used herein refers to any method in the art by which an activity can be measured.

The term "providing" as used herein refers to any means of adding a compound or molecule to something known in the art. Examples of providing can include the use of pipettes, pipettemen, syringes, needles, tubing, guns, etc. This can be manual or automated. It can include transfection by any mean or any other means of providing nucleic acids to dishes, cells, tissue, cell-free systems and can be in vitro or in vivo.

The term "preventing" as used herein refers to administering a compound prior to the onset of clinical symptoms of a disease or conditions so as to prevent a physical manifestation of aberrations associated with the disease or condition.

The disclosed compositions and methods can be further understood through the following numbered paragraphs.

1. A virus comprising a heterologous nucleic acid segment encoding α-1,3-galactosyltransferase (α-1,3-GT), wherein the nucleic acid segment expresses α-1,3-GT when the virus infects a host cell, wherein at least one protein exposed on the surface of the host cell when the virus infects the host cell comprises α-1,3-galactose.

2. The virus of paragraph 1, wherein at least one viral protein expressed by the virus when the virus infects the host cell comprises α-1,3-galactose.

3. The virus of paragraph 1 or 2, wherein the virus is live and attenuated.

4. The virus of any one of paragraphs 1-3, wherein the nucleic acid segment is incorporated into the genome of the virus.

5. The virus of any one of paragraphs 1-4, wherein the nucleic acid segment is incorporated in frame into the reading frame of a viral coding region of the virus.

6. The virus of paragraph 5, wherein the nucleic acid segment is incorporated immediately before the stop codon of the reading frame of the viral coding region of the virus.

7. The virus of paragraph 6, wherein the virus further comprises a protease cleavage site encoded between the nucleic acid segment and the viral coding region of the virus.

8. The virus of any one of paragraphs 1-7, wherein virus is an influenza virus.

9. The virus of paragraph 8, wherein the nucleic acid segment is incorporated in frame into the reading frame of the neuraminidase (NA) coding region of the virus.

10. The virus of paragraph 9, wherein the nucleic acid segment is incorporated immediately before the stop codon of the reading frame of the NA coding region of the virus.

11. The virus of paragraph 10, wherein the virus further comprises a protease cleavage site encoded between the nucleic acid segment and the NA coding region of the virus.

12. The virus of any one of paragraphs 7-11, wherein the protease cleavage site is comprised in a 2A self-cleaving peptide.

13. The virus of paragraph 12, wherein the 2A self-cleaving peptide is derived from porcine teschovirus-1.

14. The virus of paragraph 12 or 13, wherein the 2A self-cleaving peptide is flanked by short peptide linkers.

15. The virus of paragraph 14, wherein the peptides linkers are GSG.

16. The virus of any one of paragraphs 1-15, wherein the α-1,3-GT is a mammalian α-1,3-GT.

17. The virus of any one of paragraphs 1-16, wherein the α-1,3-GT is a mouse α-1,3-GT.

18. The virus of any one of paragraphs 1-17, wherein the virus is attenuated by serial passage in cultured cells, serial passage in a heterologous host animal, gene deletion in the virus, site-directed mutagenesis of the virus, altering codon usage of the virus, selection of cold-adapted mutants, using a related virus from a heterologous host species, using a naturally occurring attenuated virus strain, or combinations thereof.

19. The virus of paragraph 18, wherein the virus is attenuated by serial passage in cultured cells, wherein the cultured cells are Madin-Darby Canine Kidney (MDCK) cells.

20. The virus of any one of paragraphs 1-19, wherein the virus is an influenza virus, Influenza A virus, Influenza B virus, Human papillomavirus, Measles virus, Human immune deficiency virus, Rabies virus, Ebolavirus, Hantavirus, Marburg virus, Lassa virus, Dengue virus, Eastern equine encephalitis virus, Hepatitis C virus, Hepatitis A virus, Hepatitis B virus, Hepatitis E virus, Human herpesvirus, Human SARS coronavirus, Mumps virus, Polio virus, Rubella virus, Varicella-zoster virus, Rift valley fever virus, West Nile virus, Yellow fever virus, Human T-lymphotropic virus, or Merkel cell polyomavirus.

21. The virus of paragraph 20, wherein the virus is an influenza virus.

22. A vaccine comprising the virus of any one of paragraphs 1-21, wherein the virus is live and attenuated.

23. A vaccine comprising one or more viral proteins expressed by the virus of any one of paragraphs 1-21, wherein the one or more viral proteins comprise α-1,3-galactose.

24. A method of vaccination, the method comprising administering to a subject in need thereof a vaccine of paragraph 22 or 23.

25. The method of paragraph 24, wherein the vaccine is administered intranasally, pulmonarily, orally, subcutaneously, intramuscularly, intradermally, or intraperitoneally.

26. A method of making the vaccine of paragraph 23, the method comprising infecting a cell with the virus, whereby the one or more viral proteins comprising α-1,3-galactose are produced.

27. The method of paragraph 26 further comprising purifying the one or more viral proteins.

The recombinant influenza virus PR8/NAGT described herein was deposited under terms in accordance with the Budapest Treaty in the American Type Culture Collection (ATCC) having an address of P.O. Box 1549, Manassas, VA 20110 USA on Aug. 22, 2019, with the following deposit number: PTA-125887. Viability of the deposited material was validated as of Aug. 22, 2019.

EXAMPLES

Example 1. Characterization of a NA-Mutant Expressing α-1,3-Galactosyltransferase In Vitro Materials and Methods Generation of NAGT Mutant Mouse α-1,3-GT gene RT-PCR amplified from spleen tissues of a Balb/c mouse was introduced into a plasmid expressing PR8 NA vRNA (pHW2000-PR8-NA)(34) as shown in FIG. 1. Recombinant PR8 WT and NAGT viruses were generated by standard reverse genetic technologies (Hoffmann, et al., *PNAS*, 97:6108-6113 (2000)). Rescued viruses were cultured in 10-day-old embryonated chicken eggs for further amplification. Viral sequences of rescued viruses were confirmed by standard Sanger sequencing.

Western Blotting Analyses

Infected A549 cells (MOI=1) were harvested at 24 hours post-infection. Cell lysates were resolved in 12% resolving PAGE gels. 1000× diluted rabbit anti-neuraminidase antibody (ab21304; Abcam) and 2000× diluted horseradish peroxidase (HRP) goat anti-rabbit IgG (ab205718; Abcam) were used as primary antibody and secondary antibody, respectively, in the assay.

Immunofluorescence Staining Assays

Infected cells (MOI=1) were fixed in 4% paraformaldehyde solution in PBS at 24 hour post-infection as described in Leung, et al., *J. Virol.*, 86:10704-13 (2012). 5× diluted mouse anti-α-Gal monoclonal IgM (M86, Enzo life sciences) and 2000× diluted fluorescent-dye conjugated goat anti-mouse IgG/IgA/IgM antibody (10667, Invitrogen) were used as primary antibody and secondary antibody, respectively, in the assay. DAPI was used as a nuclear counterstain (Invitrogen). Human A549 cell infected by WT or NAGT virus at 24 hours post-infection were stained for α-Gal epitopes. For detection of α-Gal epitopes on non-permeabilized cells, human A549 cells treated with NAGT mutant or PBS (control) were stained. The staining protocol is as described above, except that Triton X-100 was not used in the initial cell fixation.

Viral Replication Kinetics Assays

MDCK cells were infected with influenza virus (MOI=0.001) in triplicate. Infected cells were briefly washed by acidified PBS (pH 2.0) once and PBS (pH 7.0) twice after a 1-hour virus adsorption period at 37° C., followed by supplementing with virus culture medium as described in Leung, et al., *J. Virol.*, 86:10704-13 (2012). The titres of progeny virus were determined by standard plaque assays.

Antibody-Dependent NK Cell Assays

Human A549 cell were infected with NAGT or WT PR8 virus at MOI of 10 for 5 hours as described in Jegaskanda, et al., *J. Immunol.*, 190:1837-1848 (2013). Infected cells were stained by PE-Cy7 anti-human HLA-A, B, C antibody (clone W6/32, Biolegend). PBS-treated cells were used as a negative control. Treated A549 cells were incubated with anti-human CD107a APC (clone LAMP-1, Biolegend)-treated CD16.NK92 cells (Fox Chase Cancer Centre) in the presence of heat-inactivated human serum (1:20 dilution) for 5 hours. After the incubation, cell mixtures were stained by anti-human CD56-PE antibody (clone MEM188, Biolegend) and fixed. Treated cell mixtures were then stained by anti-NP-FITC (Abcam) antibodies. Signals for NK cell activation (CD56$^+$CD107a$^+$) and those for infected A549 cells (NP$^+$HLA$^+$) were acquired by BD LSR Fortessa. Signals generated infected cells without pre-incubating with human serum and those from mock-infected cells with/without pre-incubating with human serum were used as controls. All data were analysed using FlowJo. The fold of reduction (%) in infected cells due to α-Gal expression was equal to:

$$\left| \frac{\% \text{ of } NP + HLA + \text{cells in the presence of serum} - }{\dfrac{\% \text{ of } NP + HLA + \text{cells in the absence of serum}}{\% \, NP + HLA + \text{cells in the absence of plasma}}} \right| * 100\%$$

ADCC

A commercial luciferase reporter assay kit was used for measuring ADCC activities (ADCC Receptor Bioassay Kit, Promega). In brief, A549 cells were infected by WT or NAGT mutant (10 MOI). At 5 hours post-infection, cells were co-incubated with diluted human serum and recombinant Jurkat effector cells for 6 hours. Cell mixtures without addition of human serum were used as controls. Luciferase activities of effector cells induced by infected cells were measured by standard luciferase assays. The fold of induction of ADCC response was equal to:

$$\frac{\text{Relative luminometer units from reaction in the presence of human serum}}{\text{Relative luminometer units from reaction in the absence of human serum}}$$

Phagocytosis Assays

Human monocyte derived macrophages were prepared as described in Manches, et al., *Haematologica*, 90:625-34 (2005). The day prior to the experiment, A549 cells were infected by WT or NAGT virus (MOI=1), followed by an overnight culture. Infected cells were incubated with human serum on the day of experiment at 4° C. for 30 mins. Serum-treated cells were added to the macrophages in 3:1 ratio and the cell mixture was incubated at 37° C. for 2 hours. Incubated cell mixtures were washed with PBS, fixed in 4% paraformaldehyde and then stained with Giemsa. Stained macrophages were examined under a standard light microscope. Work for collecting primary human monocytes and human serum samples were approved by a local RB.

Statistical Analyses

Unless stated otherwise, One-way ANOVA was used to determine the effect on the magnitude of cellular immune responses and cell population profiles.

Results

Antigen uptake by professional antigen presenting cells (APCs) such as dendritic cells (DCs) plays a key role in adaptive immunity. The antigen uptake process can be enhanced by opsonization of antigens and a high level of pre-existing antibodies specific for the antigen can facilitate this process (Boudreau and Alter, *Front. Immunol.*, 10:440 (2019)). The expression of galactose-alpha-1,3-galactose (α-Gal) epitopes on membrane surface can enhance their opsonization leading to phagocytosis by APCs mediated by anti-Gal antibodies which are naturally expressed in healthy individuals. This results in enhancing phagocytosis of infected cells by professional APCs (Galili, *Immunology*, 140:1-11 (2013)). Human polyclonal anti-α-Gal antibodies exist in different forms (IgA, IgG and IgM) and they are abundantly expressed in healthy individuals (about 1% of circulating immunoglobulins). α-Gal epitopes are expressed by a wild range of living organisms. This epitope is presented by surface glycoproteins or glycolipids after the enzymatic reaction of α-1,3-galactosyltransferase (α-1,3-GT) within the endoplasmic reticulum (Galili, Immunology, 140:1-11 (2013)). However, humans, apes and old world monkeys have a defective α-1,3-GT gene and they are unable to express this epitope (Galili, Immunology, 140:1-11 (2013)). Because of the continuous stimulation with α-Gal epitopes in foods and normal bacteria flora, a high level of anti-α-Gal antibodies is naturally produced by these primates throughout their lifetime.

The use of α-Gal epitope to stimulate T and B cells responses through enhancing antigen uptake has been demonstrated in cancer therapy and experimental vaccines (Albertini, et al., *Cancer Immunol. Immunother.*, 65:897-907 (2016); Abdel-Motal, et al., *Vaccine*, 28:1758-65 (2010); Henion, et al., *Vaccine*, 15:1174-82 (1997)). Previous viral vaccine studies were based on inactivated viral antigens artificially coated with α-Gal epitopes and these vaccines were shown to enhance adaptive immune response against a homologous virus infection. However, this strategy requires additional enzymatic processing to generate α-Gal epitopes on these antigens, thereby reducing antigen yields and cost effectiveness. Here, an attenuated influenza virus that contains a α-1,3-GT gene in order to express α-Gal epitopes in infected cells was generated.

Figure 2:
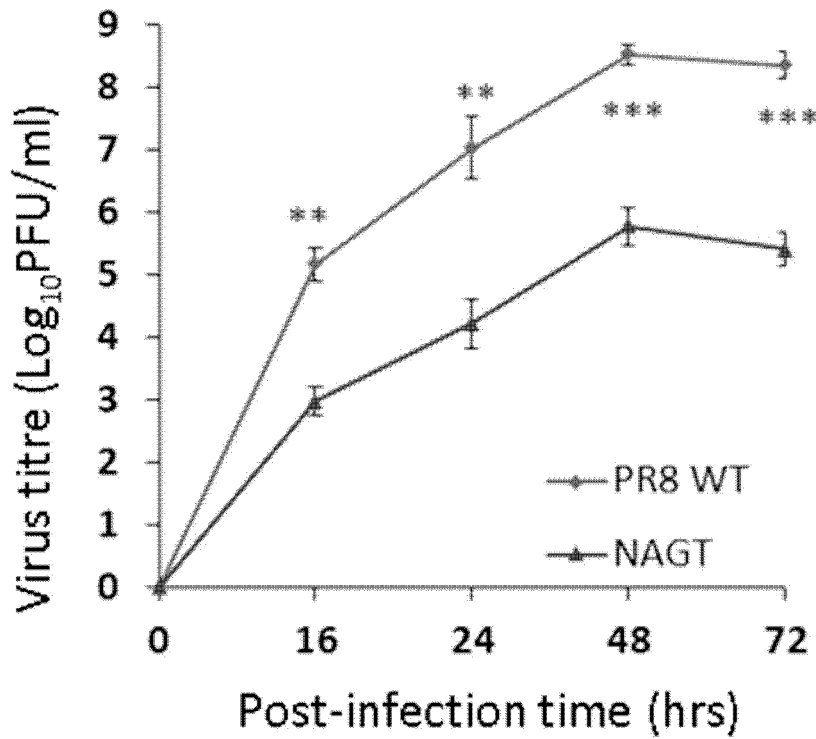
FIG. 2 is a graph showing replication kinetics of NAGT mutant in MDCK cells (MOI: 0.001). Progeny virus titres were determined using standard plaque assays. Mean SD; : p<0.01, *: p<0.001.

To express α-gal epitopes in infected cells, a recombinant A/PR/8/34 H1N1 (PR8) virus carrying a mouse α-1,3-GT gene in its neuraminidase (NA) vRNA segment was made (hereafter called NAGT mutant) (FIG. 1). The α-1,3-GT gene was inserted immediately before the stop codon of the NA open reading frame (ORF) in the same sense. A 2A peptide derived from porcine teschovirus-1 flanked by short peptide linkers (GSG) was inserted into the junction of NA and α-1,3-GT ORFs in order to allow an efficient cleavage of NA/α-1,3-GT polypeptide into NA and α-1,3-GT proteins (Kim, et al., *PLoS One*, 6:e18556 (2011)). The cleavage of NA/α-1,3-GT polypeptide into NA and α-1,3-GT proteins was demonstrated in the detection of influenza NA protein infection by Western blotting, where human A549 cells infected by WT and NAGT viruses (MOI of 1) were harvested at 48 hours post-infection (data not shown). The packing signal at the 5' end of NA vRNA (UTR and 157 nt at ORF region) was inserted next to the stop codon of NA/GT ORF sequence. The NAGT mutant was attenuated in MDCK cells (about 2.5 log reduction in virus titre), but it was still able to achieve a relatively robust replication in infected cells with a maximum titre of about 5.8e5 pfu/ml (FIG. 2). Preliminary mouse infection studies showed that the NAGT mutant was attenuated in mice (MLD50 of WT=178 pfu; MLD50 of NAGT=2700 pfu). The NAGT mutant is about 15 times less virulent than its WT control in mice. Although this virus background (PR8) is lethal in mice, it is a standard master strain for making seasonal influenza vaccines. Further attenuation of mutant might be needed, for example, by using codon bias to fine-turn the level of virus attenuation (Fan, et al., *J. Virol.*, 89:10762-73 (2015)). Therefore the level of attenuation of NAGT mutant can be adjusted by using this strategy or other approaches.

Human cells infected by the NAGT mutant, but not the WT virus, could express α-Gal epitopes both in cytoplasm and on cell surface, as demonstrated by the immunofluorescent staining of α-Gal epitopes in human A549 cells infected by WT or NAGT virus at 24 hours post-infection (data not shown).

Figure 3:
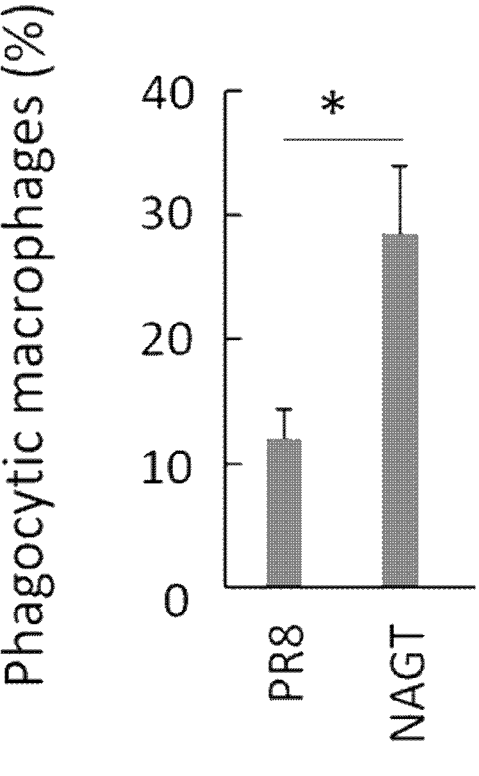
FIG. 3 is a bar graph showing enhance phagocytic activities of human monocyte-derived macrophages by human A549 cells infected by NAGT virus. Mean SD; *: p<0.05.
Figure 5:
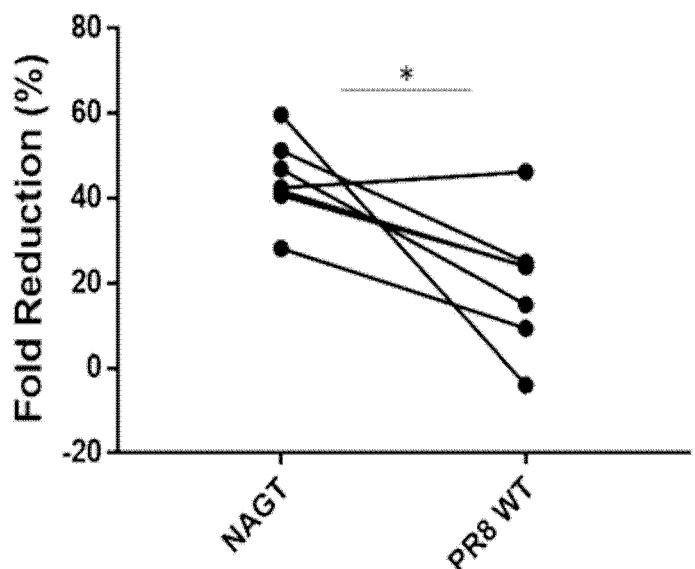
FIG. 5 is a graph showing the stimulating effect of all tested human sera on NK cells to kill WT and NAGT infected A549 cells (fold reduction in NP+A549 cells; N=6; paired t-test). Mean±SD; *: p<0.05.
Figure 6:
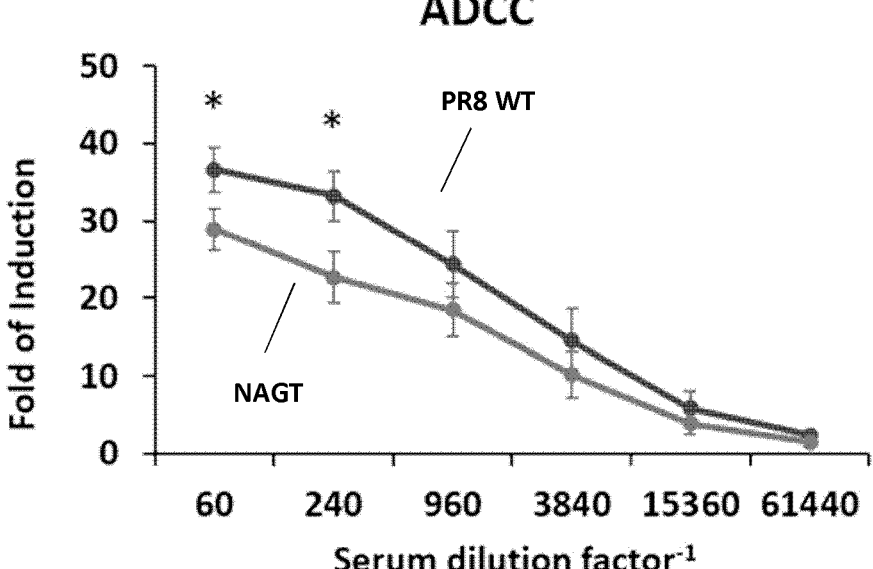
FIG. 6 is a graph showing luciferase reporter assay for ADCC activity. A549 cells infected by WT or NAGT were first treated with serially diluted human serum samples and then tested by ADCC assays. Each data point represents the average reading of 6 different human serum samples. Mean±SD; *: p<0.05.

The expression of α-Gal epitopes by the NAGT mutant can lead to binding of human anti-α-Gal antibody to infected cells, enhancing opsonization of infected cells by APCs, thereby boosting vaccine-induced adaptive responses. To demonstrate this, cells infected with WT and NAGT viruses were treated with normal human sera and the ability of primary human monocyte-derived macrophages to engulf these cells was accessed. As shown in FIG. 3, human A549 cells infected by NAGT mutants could significantly enhance the phagocytic activity of human macrophages (p<0.05). Cells infected by NAGT mutant were more susceptible to be killed by NK cells after incubating with human sera (FIG. 4A and FIG. 4B). This enhanced killing effect was much less in cells infected by WT virus (FIG. 4C and FIG. 4D). The lower killing effect stimulated by the WT virus-infected cells could be contributed to the presence of influenza virus antibodies commonly found in normal individuals. Of 6 human sera tested, cells infected by the NAGT mutant were more likely to be killed by NK cells than those infected by WT virus in 5 samples (FIG. 5; p<0.05). The stimulating effect of NAGT mutant on immune effector cells was confirmed by using an Antibody-Dependent Cellular Cytotoxicity (ADCC) reporter assay (FIG. 6).

Overall, the above results show that the expression of α-Gal epitopes by NAGT-infected cells can stimulate phagocytosis of APCs, NK cell-mediated cytotoxicity and ADCC. These enhanced effects demonstrate that the opsonization of infected cells by anti-α-Gal antibody can enhance vaccine-induced responses.

Example 2. Characterization of α-1,3-GT Knockout Mice after Vaccinated with Nagt Mutant Materials and Methods
α-1,3-GT KO mouse model and immunization studies WT C57BL/6 and its α-1,3-GT KO mice (Tearle, et al., *Transplantation*, 61:13-9 (1996)) were purchased from Shanghai Model Organisms Center Inc, China. To induce anti-α-Gal antibody in KO mice, mice were intraperitoneally injected with rabbit RBC membranes (3×10^8 in 100p PBS) at 4 and 6 weeks of age (LaTemple and Galili, *Xenotransplantation*, 5:191-6 (1998)). Sera from treated mice was collected at 4, 6 and 8 weeks of age. Serum anti-α-Gal IgG1 antibody levels in treated mice were measured by ELISA as described below. For vaccination, NAGT virus (150 pfu in 25 μl PBS) was given intranasally to KO and WT mice at 8 weeks of age. Mock vaccinated (PBS) WT and KO mice were used as controls.
ELISA
Galα1-3Galβ1-4GlcNAc-BSA (3 atom spacer, Dextra), recombinant NP or HA (Sino Biological) was coated on 96-ELISA plates (Nunc MaciSorp) at 4° C. overnight. Pooled serum samples (N≥4 per group) were 2-fold serially diluted, starting from 1:40. Anti-mouse IgG1 HRP conjugated antibody (31430, Invitrogen) was used as the secondary antibody. Absorbance at 450 nm was measured. Each sample was tested in duplicate. Endpoint titre≥4-fold difference was considered to be significance.
Cell Profiling in Infected Samples
Mouse lung and spleen tissues were harvested at days 1, 3, 5 and 21 post-vaccination, as well as days 3 and 7 post-infection (n≥5) using protocol described in Valkenburg, et al., *PNAS*, 111:5676-81 (2014). After haemolysis with RBC lysis buffer (eBioscience), cells were stained by Zombie Aqua (Biolegend) and then stained for different cell markers (Fc block by anti-CD16/CD32, BD biosciences; anti-CD11b-FITC, CD11c-PerCP/Cy5.5, Ly6G-APC, F4/80-PE, MHC II-PB, Biolegend). Stained cells were fixed (BD Cytofix/cytoperm buffer) as described in Valkenburg, et al., *PNAS,* 111:5676-81 (2014). Markers for DCs (CD11c+ MHCIIhiLy6G-F4/80–), neutrophils (Ly6GhiCD11bhi), alveolar macrophages (CD11c+F4/80+) in lungs, and macrophages (CD11b+F4/80+) in spleens were studied. Signal acquisition was performed on BD LSR Fortessa and data were analyzed by FlowJo. Gating strategies for these cells were shown in corresponding figures.

ICS Assays

CD4+ and CD8+ T-cell recall responses were determined as described in Horton, et al., *J. Immunol. Methods,* 323: 39-54 (2007) and Yan, et al., *Virology,* 525:73-82 (2018). The production of type 1 (IFN-γ, TNF-α, IL-2) and type 2 (IL-4) cytokines of T cells was detected. Splenocytes and cells from BAL (n≥3 per group) were harvested at day 7 post-infection. After RBC lysis, isolated lymphocytes were stimulated by PR8 or HK68 virus, and co-incubated with anti-CD28, anti-CD49d (BD biosciences), IL-2 (Roche) for 6 hours, followed by an incubation with Golgi plug (Brefeldin A, BD biosciences) overnight. For splenocytes at 3-week after vaccination, PR8, HK68, H1N1/Brisbane/07 (H1N1) and HK/MPF461/07 (H5N2) viruses were used to stimulate the cells. Treated cells were first stained by Zombie Aqua™ (Biolegend) and followed by T cell markers (Fc block by anti-CD16/CD32, BD biosciences; anti-CD4 APC/Cy7, CD8 PerCP/Cy5.5, Biolegend). Stained cells were then fixed by Cytofix/cytoperm buffer (BD) and followed by intracellular cytokine staining (IFN-7 FITC, TNF-α APC, IL-2 PE, IL-4 PE/Cy7, Biolegend). Signal acquisition was performed on BD LSR Fortessa and data were analyzed by FlowJo.

Statistical Analyses

Unless stated otherwise, One-way ANOVA was used to determine the effect on the magnitude of cellular immune responses and cell population profiles.

Results

Figure 7:
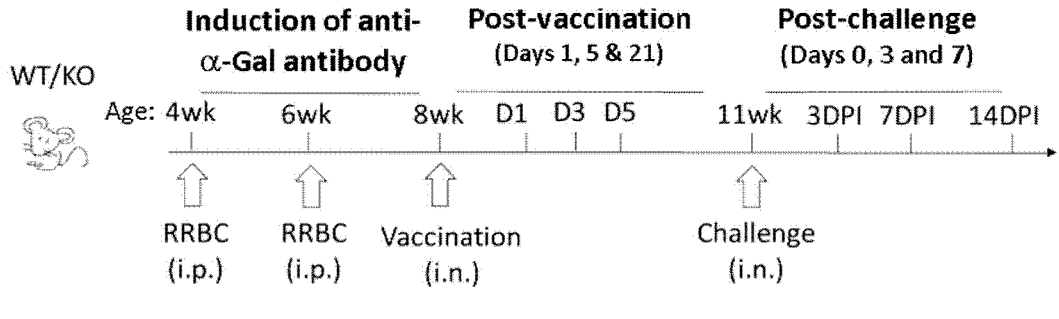
FIG. 7 is a schematic showing the vaccination and virus challenge. Mice were primed and boosted by rabbit RBCs via intraperitoneal route at 4 and 6 weeks of age. Mice were vaccinated by NAGT mutant at 8 week of age and then challenged by a lethal dose of influenza virus via intranasal route. Relevant samples were collected at 4, 6 and 8 weeks of age and at various post-vaccination (days 1, 5 and 11)/post-challenge (days 0, 3 and 7) time points.

WT laboratory mice have a functional α-1,3-GT gene and they do not produce anti-α-Gal antibodies so as to avoid autoimmunity. A α-1,3-GT knockout (KO) mouse strain was therefore used to evaluate the vaccine potential of NAGT mutant (FIG. 7) (Tearle, et al., *Transplantation,* 61:13-9 (1996)). These KO mice were first intraperitoneally injected with rabbit RBCs twice to stimulate anti-α-Gal antibody production (LaTemple and Galili, *Xenotransplantation,* 5:191-6 (1998)). A high level of anti-α-Gal antibody could be stably produced and maintained by the RBC treated KO mice (Weeks 8-11) (Table 5). By contrast, no anti-α-Gal antibody could be detected in RBC-treated WT mice.

TABLE 5

Anti-α-Gal antibody titres in different experimental groups before virus challenge in week 11.

| Group | Mice | RBC injections | Vaccination | Anti-α-Gal antibody titre | | |
| | | | | Wk 4 | Wk 8 | Wk 11 |
| WT | WT | + | + | <10 | <10 | <10 |
| KO | KO | + | + | <10 | 160 | 160 |
| KO (–) | KO | + | – | <10 | 160 | 160 |

Figure 8:
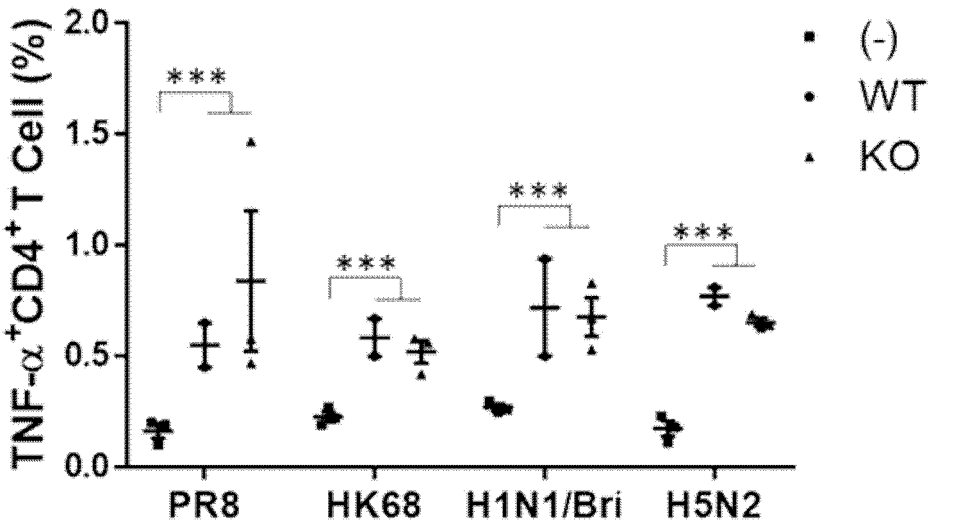
FIG. 8 is a graph showing splenic CD4$^+$ T-cell recall responses against different influenza viruses (H1N1/PR8, H3N2/HK68, H1N1/Brisbane/07 and H5N2/HK/MPF461/ 07). T cells were studied by ICS. Percentages of activated T cells (TNF$\alpha^+$) are shown. Data represent Mean±SD; ***: p<0.001.
Figure 9:
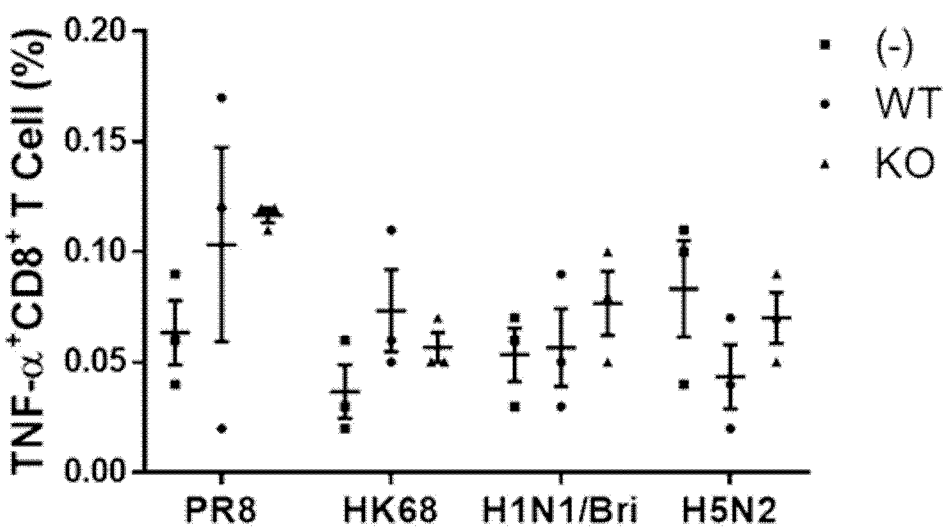
FIG. 9 is a graph showing splenic CD8$^+$ T-cell recall responses against different influenza viruses (H1N1/PR8, H3N2/HK68, H1N1/Brisbane/07 and H5N2/HK/MPF461/ 07). T cells were studied by ICS. Percentages of activated T cells (TNF$\alpha$*) are shown. Data represent Mean±SD; ***: p<0.001.

With a predetermined intra-nasal vaccination dose (150 pfu), both WT and KO vaccinated mice could produce high levels of neutralizing antibody titres against H1N1, but not H3N2, virus at 3 weeks post-vaccination (Table 6), demonstrating that the vaccine virus by itself did not stimulate heterosubtypic neutralizing antibody production. Influenza virus-specific CD4+ or CD8+ T-recall responses (TNF-α+) in spleen tissues of vaccinated mice against different influenza virus subtypes were measured in vitro using intracellular cytokine staining (ICS) assays. In comparison to the results from mock vaccinated KO mice, splenic CD4+ T cells from both vaccinated WT and KO mice could be stimulated by different viral subtypes (H1N1, H3N2 and H5N2; p<0.05) (FIG. 8), demonstrating that there were cross-reactive CD4+ T-cell responses in vaccinated mice. Cross-reactive CD8+ T-cell responses could not be observed in vaccinated mice, although both vaccinated WT and KO mice have some, yet insignificant, CD8+ recall responses against the homologous virus (PR8) (FIG. 9). Hence, the antibody and T-cell responses between vaccinated WT and KO mice at day 21 post-vaccination were similar.

TABLE 6

H1N1 and H3N2 virus-specific neutralizing antibody titres in different experimental groups before virus challenge in week 11.

| group | Mouse | RBC injections | Vaccination | Neutralizing antibody titre | |
| | | | | PR8 (H1N1) | HK68 (H3N2) |
| WT | WT | + | + | 160 | <10 |
| KO | KO | + | + | 160 | <10 |
| KO (–) | KO | + | – | <10 | <10 |

Figure 10A:
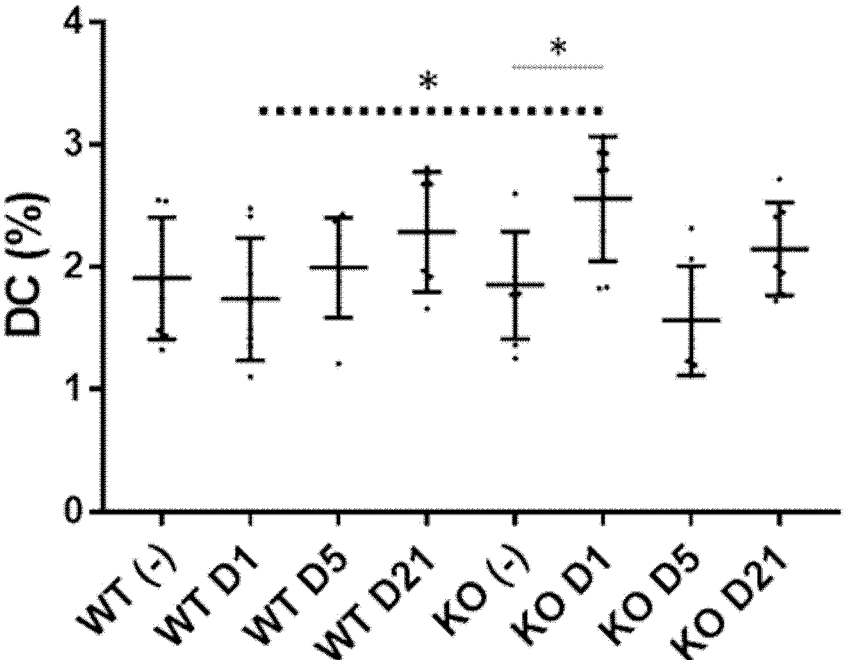
FIGS. 10A-10C are graphs showing professional antigen presenting cells (DCs and macrophages) and neutrophils in spleen after vaccination. Vaccinated WT and KO mice were harvested at days 1, 5 and 21 post-vaccination. Unvaccinated mice (–) were used as controls. Representative FACS plots and percentages of DCs (FIG. 10A), neutrophils (FIG. 10B) and macrophages (FIG. 10C) of all studied samples are shown. Data from vaccinated mice were highlighted by grey boxes. Dot line for comparison between KO and WT mice at the same time point (t-test). Data represent Mean±SD; *: p<0.05, **: p<0.01.
Figure 10B:
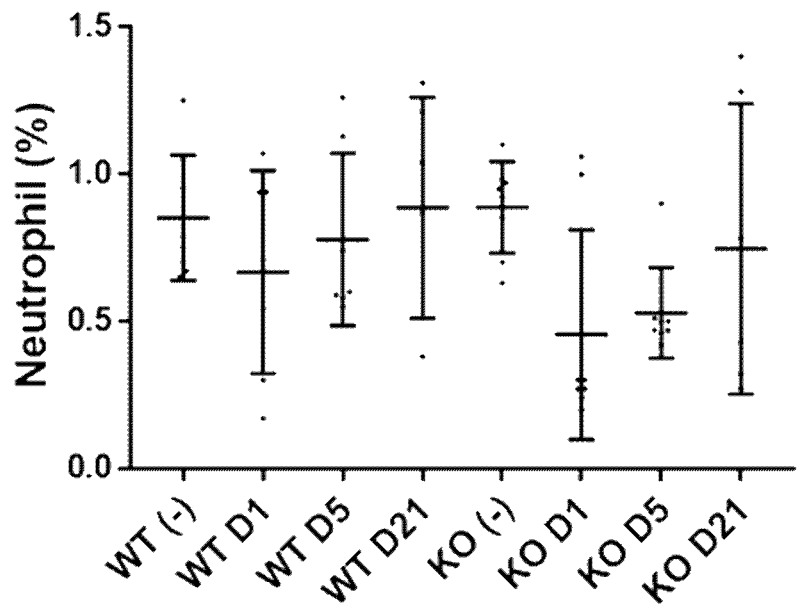
Figure 10C:
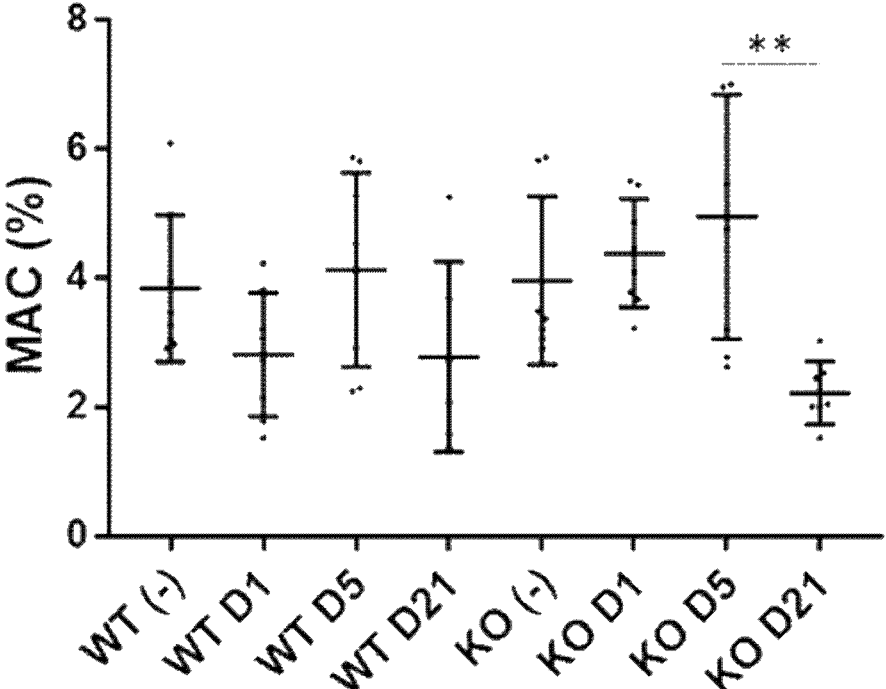

To determine whether the NAGT mutant can induce more robust responses in other immune cells, the frequencies of DCs, macrophages and neutrophils in the spleen (FIGS. 10A-10C) and lung (FIGS. 11A-11E) of vaccinated mice were studied at days 1, 5 and 21 post-vaccination. An elevation of DC population (CD11c+MHCII$^{hi}$Ly6G⁻F4/80⁻) was observed in the spleen tissues of KO mice at day 1 post-vaccination (FIG. 10A), demonstrating that this mutant can stimulate the migration of DCs into the spleen. By contrast, the neutrophils or macrophages profiles in the spleens of these WT and KO mice at these time points were similar (FIG. 10B and FIG. 10C).

Figures 11A, 11B:
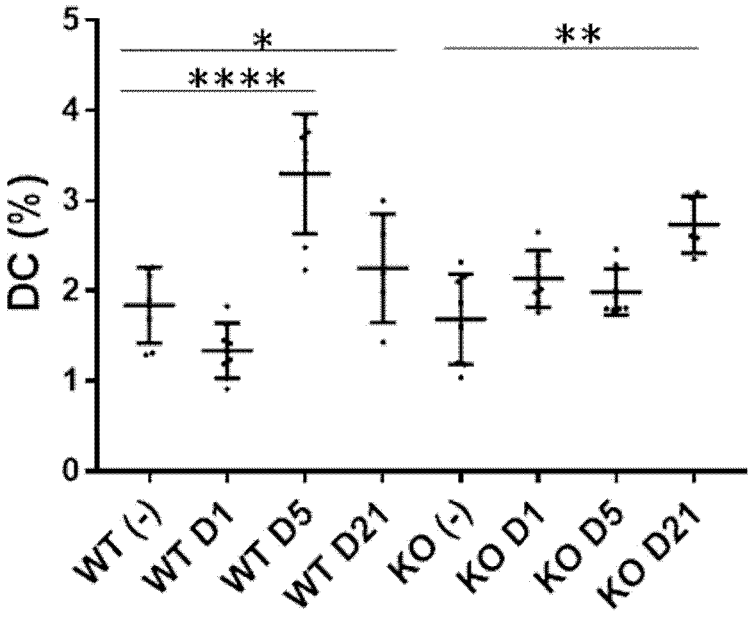
FIGS. 11A-11E are graphs showing professional antigen presenting cells (DCs and alveolar macrophages) and neutrophils in lung after vaccination. Vaccinated WT and KO mice were harvested at days 1, 5 and 21 post-vaccination. Unvaccinated mice (–) were used as controls. Representative FACS plots and percentages of DCs (FIG. 11A), CD11b$^{lo/-}$ DCs (FIG. 11B) and CD11b$^{hi}$ DCs (FIG. 11C), neutrophils (FIG. 11D) and alveolar macrophages (FIG. 11E) observed from all studied samples. Data from vaccinated mice were highlighted by grey boxes. Data represent Mean±SD; *: p<0.05, : p<0.01, *: p<0.001, ****: p<0.0001.
Figure 11C:
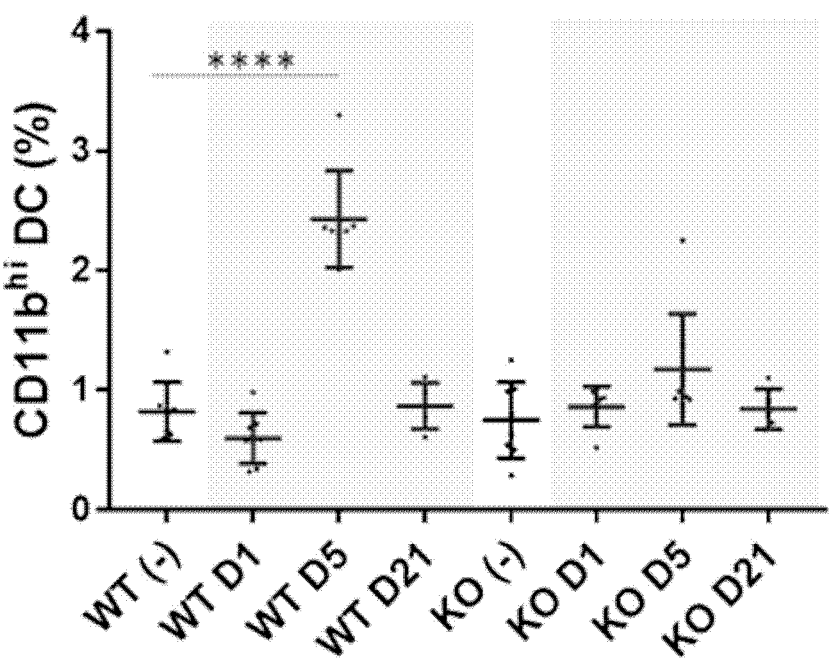
Figure 11D:
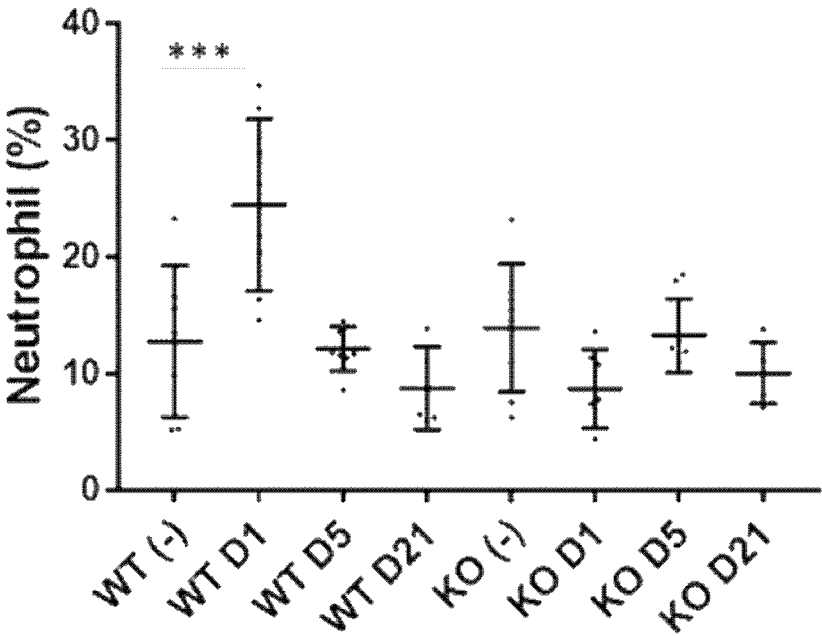
Figure 11E:
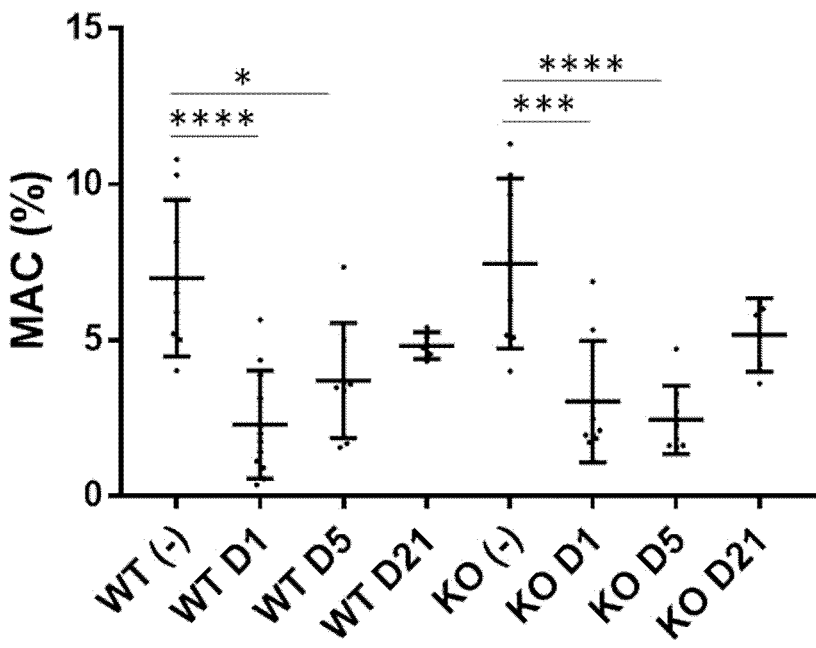

Increased frequency of pulmonary DCs (CD11c+ MHCII$^{hi}$Ly6G⁻F4/80⁻) in these vaccinated mice was observed, peaking at day 5 and day 21 in vaccinated WT and KO mice, respectively (FIG. 11A). Apart from the difference in kinetics, the studied DC populations in the WT and KO mice at these time points were slightly different (CD11b$^{hi}$ vs CD11b$^{lo/-}$) (FIG. 11B and FIG. 11C). The increased DC population of vaccinated KO mice was primarily CD11b$^{lo/-}$ (FIG. 11B). By contrast, a substantial increase of CD11b$^{hi}$ DC population (FIG. 11C) and a marginal increase of CD11b$^{lo/-}$ (insignificant to the unvaccinated control) could be detected in vaccinated WT mice at day 5 post-vaccination (FIG. 11B). An elevated neutrophil frequency in vaccinated WT mice at day 1 post-vaccination was observed (FIG. 11D), demonstrating that the NAGT mutant caused relatively more severe inflammatory responses in WT mice because of the lack of anti-α-Gal antibody in these mice to control the infection (Ueki, et al., *PNAS,* 115:E6622-E6629 (2018)). Both vaccinated WT and KO mice had reduced levels of alveolar macrophages after vaccination (FIG. 11E), but the reductions were indistinguishable.

DCs are vital for immune surveillance. This cell population can help to eliminate pathogens via adaptive immune responses. Opsonized immune complexes can be efficiently internalized by monocyte derived DCs via interactions between the Fc portion of antibodies and Fc receptors of DCs (Guilliams, et al., *Nat. Rev. Immunol.,* 14:94-108 (2014)). Antigen loaded DCs can migrate to draining lymph nodes to activate T cells. Increasing such DC-T cell interactions in lymphoid systems are expected to enhance immune memory responses against influenza virus (Eisenbarth, *Nat. Rev. Immunol.,* 19:89-103 (2019); Lehmann, et al., *J. Exp. Med.,* 214:1509-1528 (2017)). Pulmonary mouse lung DCs (CD11c$^+$MHCII$^{hi}$) can be divided into two major subpopulations: CD11b$^{lo/-}$ and CD11b$^{hi}$ DCs (Condon, et al., *J. Leukoc. Biol.,* 90:883-95 (2011)). In this study, both vaccine groups had increased total DC populations in lung tissues after vaccination, but the increased DC subsets in these vaccinated mice were different. The increased DC population in vaccinated KO mice was entirely CD11b$^{lo/-}$, whereas the increased DC population in vaccinated WT mice was predominantly CD1 1b$^{hi}$ (FIG. 11B). This demonstrates that the NAGT mutant can modulate protective DC responses in these mouse groups.

Overall, these results show that the NAGT mutant can direct DC and other APC responses in WT and KO mice after vaccination.

Health individuals are regularly exposed to α-Gal epitopes via exogenous sources (e.g., food). These regular exposures also explain why different forms of α-Gal antibodies, including serum IgG, are being maintained at high levels in normal individuals. Further test on the safety aspect of this vaccine approach is warranted, such as any side effects in healthy individuals with repeated immunizations of NAGT mutant.

Example 3. NAGT Mutant can Protect Mice Against a Lethal Virus Challenge

Material and Methods
Virus Challenge Studies

NAGT virus (150 pfu in 25 μl PBS) was given intranasally to KO and WT mice at 8 weeks of age. Mock vaccinated (PBS) WT and KO mice were used as controls. Treated mice were anesthetized and challenged intranasally by a lethal dose (H1: 40 MLD$_{50}$; H3 or H5: 10 MLD$_{50}$) of influenza virus 3 weeks after vaccination as described in Valkenburg, et al., *PNAS,* 111:5676-81 (2014). Influenza viruses used in this study were: PR8 (A/Puerto Rico/8/1934; H1N1), mouse-adapted HK68 (A/Hong Kong/1/68; H3N2), or highly pathogenic avian H5N1 (A/Vietnam/1203/2004; H5N1) viruses. Morbidity and weight loss were monitored for 14 days, and survival curves were recorded. Thirty percent of weight loss was set as the humane endpoint for euthanasia. Tissue samples from representative mice were collected at various time points as specified. All H5 studies were performed in biosafety level 3 facilities. All animal experiments were approved by the Committee on the Use of Live Animals in Teaching and Research (CULATR) of HKU.

Viral Load Assays

Lungs from challenged mice were harvested at days 3 and 7 post-infection (N≥3), followed by mechanical homogenization. The virus loads were titrated by TCID$_{50}$ assays in MDCK cells using the Reed-Muench formula.

Serological Assays

Heat-treated serum before and after virus challenge were studied by ELISA and microneutralization (MN) assay to measure influenza virus-specific antibody titres as described (Valkenburg et al., Proc. Natl. Acad. Sci. USA 111:5676-81 (2014); Valkenburg et al., Vaccine 36:4198-4206 (2018)).

ELISA was performed as described above. For MN assays, pooled RDE-treated serum samples (n≥3 per group) were 2-fold serially diluted, starting from 1:10, and tested against PR8 or HK68 virus. The neutralization antibody titres were expressed in geometric mean titre values.

Statistical Analyses

Unless stated otherwise, One-way ANOVA was used to determine the effect on the magnitude of cellular immune responses, cell population profiles, as well as viral loads within WT or KO groups, while t-test was used to for the same purpose between WT and KO mice at the same time point. Survival curves based on weight loss were analyzed by GraphPad Prism. Log-rank test was used to compare the survival rates between groups.

Results

NAGT Mutant can Protect Mice Against a Lethal Homologous Challenge

Figure 12A:
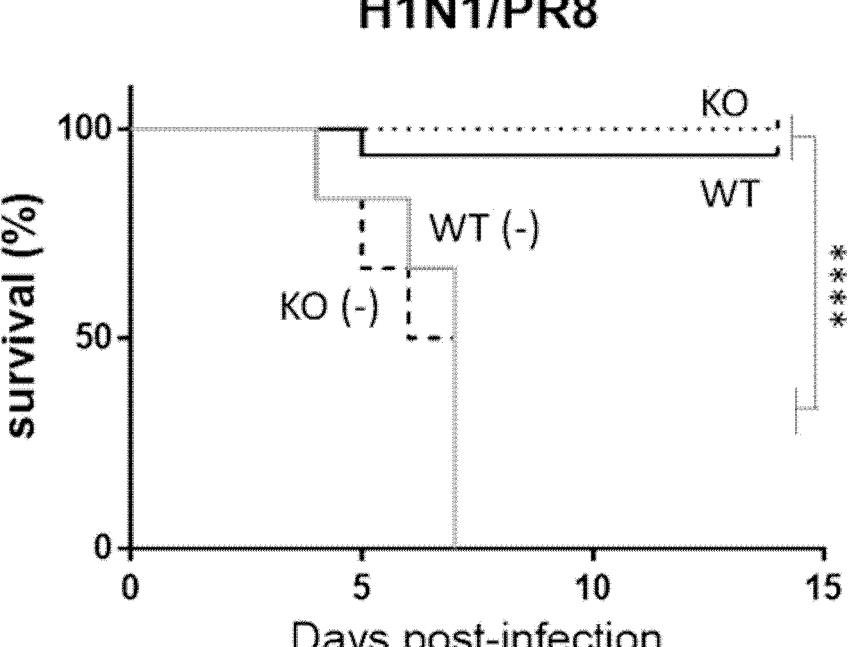
FIGS. 12A-12C are graphs showing protection of mice by NAGT mutant against a lethal homologous challenge. Vaccinated and unvaccinated (–) mice were challenged with a lethal dose of H1N1 (A/PR/8/34; 40 $MLD_{50}$) at 3 weeks post-vaccination.
Figure 12B:
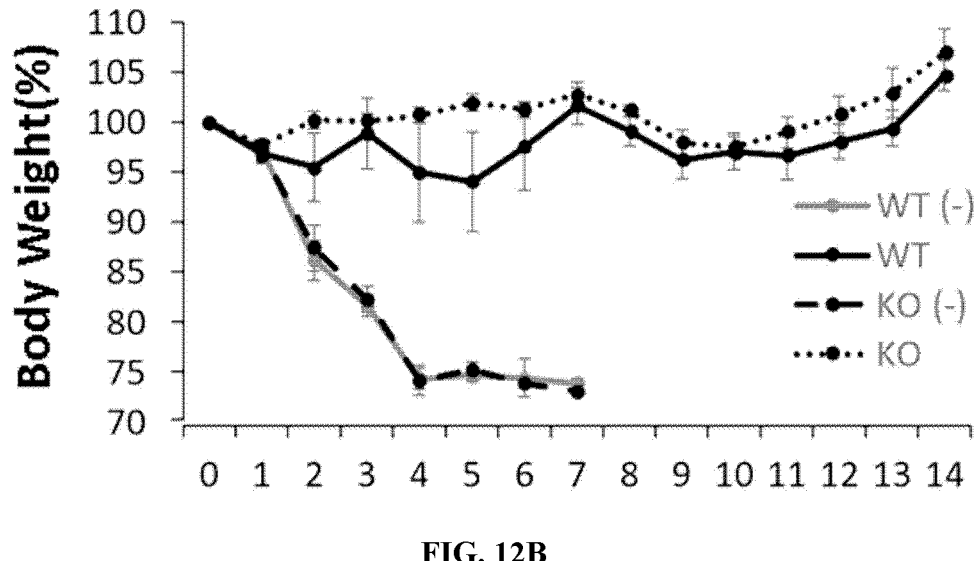
Figure 12C:
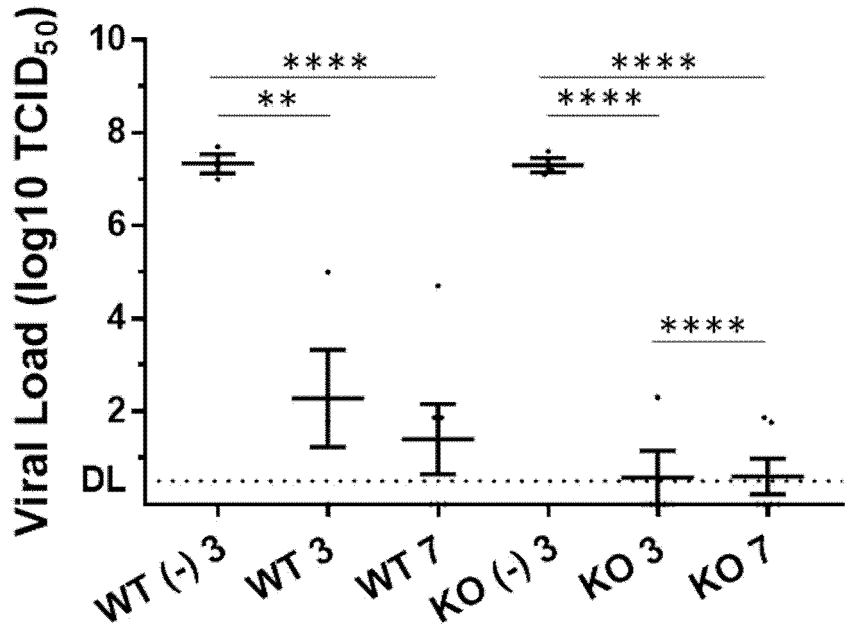

The vaccine potential of NAGT mutant was first tested by a homologous challenge. Rabbit RBC-primed WT and KO mice were challenged by a lethal dose of WT PR8 virus (10 MLD$_{50}$) at day 21 post-vaccination. All mock-vaccinated WT and KO mice died from the infection as expected. All and 94% of vaccinated KO and WT mice, respectively, survived from the challenge (FIG. 12A), with no apparent weight loss in the vaccinated KO mouse group (FIG. 12B). Both vaccinated groups mounted good antibody responses against influenza NP protein after challenge (Table 7). Although both vaccinated groups had much reduced virus lung titres than the unvaccinated control groups, vaccinated KO mice had a faster virus clearance rate than vaccinated WT mice (FIG. 12C).

Figure 13A:
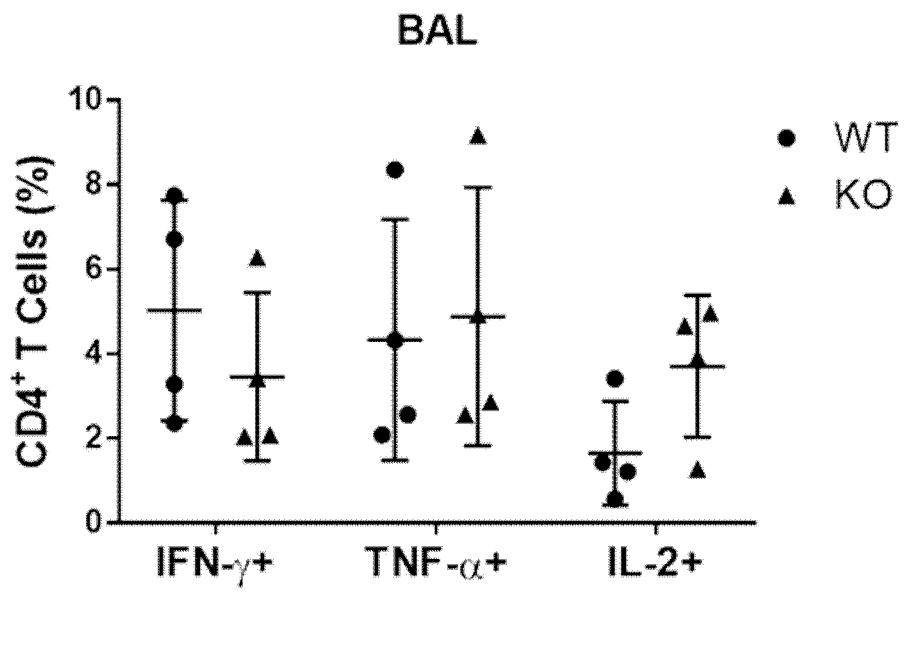
FIGS. 13A-13B are graphs showing PR8-specific CD4$^+$ (FIG. 13A) and CD8$^+$ (FIG. 13B) T-cell recall responses in BAL of infected mice at day 7 post-infection. Activities were determined by ICS assays. Data represent Mean±SD; *: p<0.05, : p<0.01, *: p<0.001, ****: p<0.0001.
Figure 13B:
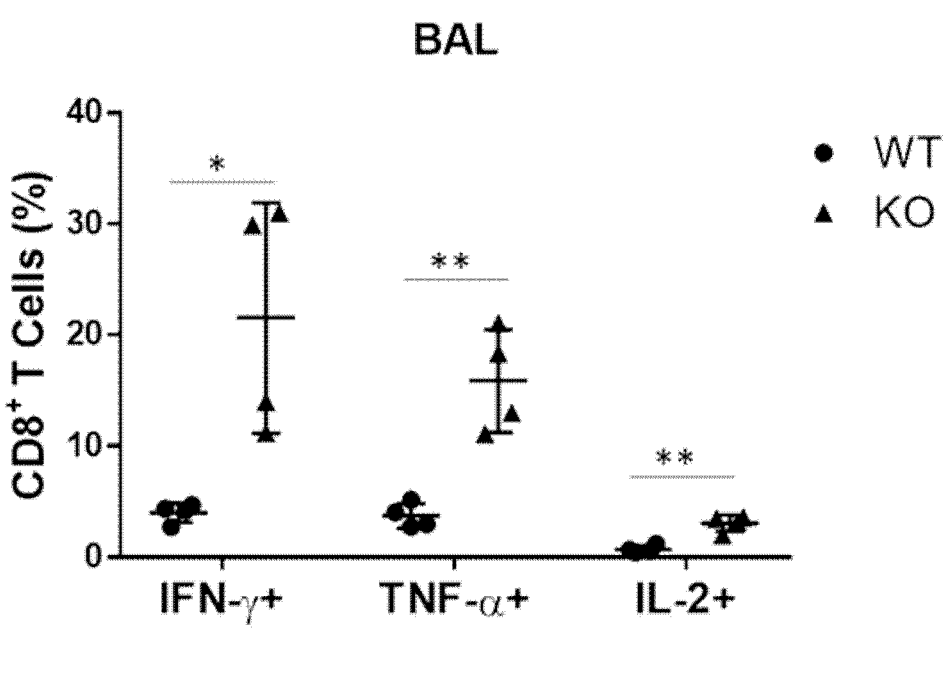
Figure 14A:
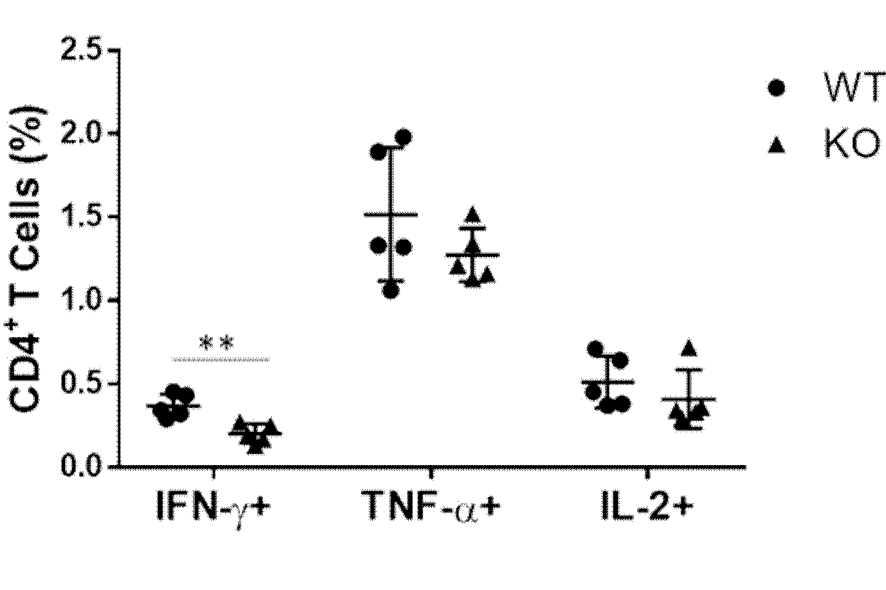
FIGS. 14A-14B are graphs showing PR8-specific CD4$^+$ (FIG. 14A) and CD8$^+$ (FIG. 14B) T-cell recall responses in spleen of infected mice at day 7 post-infection. Activities were determined by ICS assays. Data represent Mean± SD; *: p<0.05, : p<0.01, *: p<0.001, ****: p<0.0001.
Figure 14B:
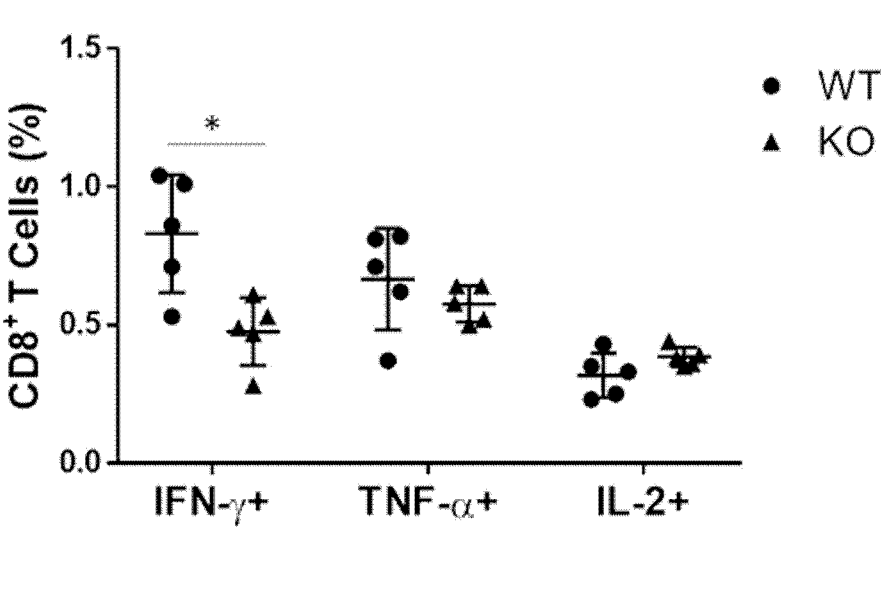

Vaccine-induced influenza-specific T-cell responses in the respiratory (bronchoalveolar lavage, BAL) and spleen samples of treated mice were measured at day 7 post-challenge. Influenza-specific CD4$^+$ and CD8$^+$ T-cell responses were measured by IFN-γ ICS assays after an ex vivo stimulation with PR8. In BAL, CD8$^+$ T-cell responses of KO mice were much higher than those of WT mice (e.g., IFN-γ$^+$ and TNF-α$^+$) (FIG. 13B). In spleen, both IFN-γ$^+$ CD4$^+$ and CD8$^+$ T-cell responses from WT mice were only slightly, yet significantly, better than those of KO mice (FIG. 14A and FIG. 14B). The profiles of DCs, neutrophils and macrophages in lung and spleen tissues were also determined at days 0, 3 and 7 post-challenge, but no significant difference between these mice was detected.

TABLE 7

| Mouse | Vaccination | Days Post-infection | Endpoint titer against NP |
|---|---|---|---|
| | NP-specific antibody titres in mice at days 0, 7, and 14 days after virus challenge[a]. | | |
| WT | – | 0 | <40 |
| | + | 0 | <40 |
| | + | 7 | 2560 |
| | + | 14 | 160 |
| KO | – | 0 | <40 |
| | + | 0 | <40 |
| | + | 7 | 640 |
| | + | 14 | 80 |

[a]antibody levels were studied by ELISA assays.

In short, the rapid virus clearance and the highly robust CD8+ T-cell responses as observed in the vaccinated KO mice demonstrate that the NAGT mutant, in the presence of anti-Gal antibody, can induce enhanced immune responses in this mouse model, which expresses a high level of anti-α-Gal antibody in vivo.

NAGT Mutant can Protect Mice Against a Lethal Hetero-subtypic H3N2 Challenge

Figure 15A:
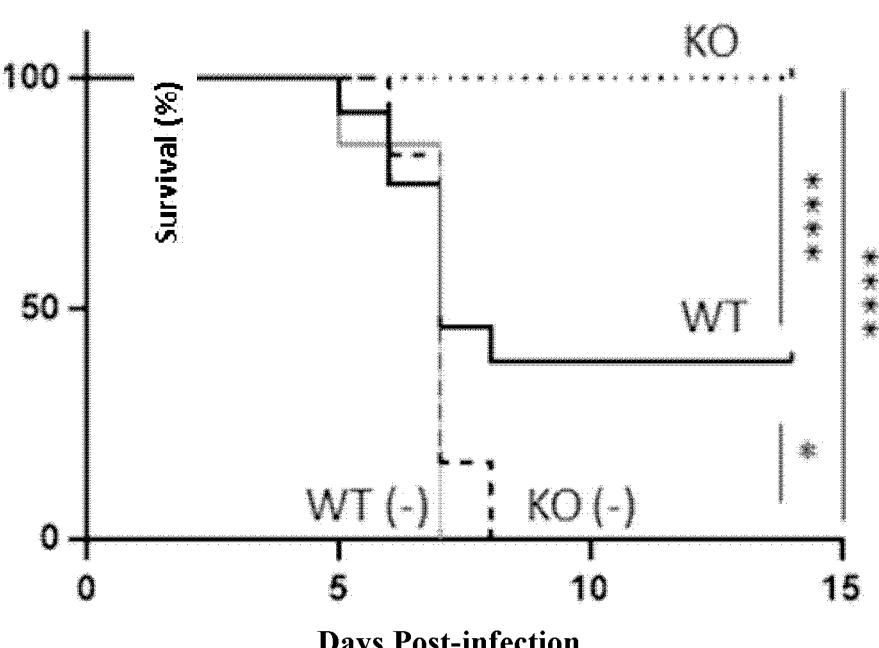
FIGS. 15A-15D are graphs showing protection of mice by NAGT mutant against a lethal heterosubtypic H3N2 challenge. Vaccinated and unvaccinated (–) mice were challenged with a lethal dose of H3N2 virus (HK68; 10 $MLD_{50}$) at 3 weeks post-vaccination.
Figure 15B:
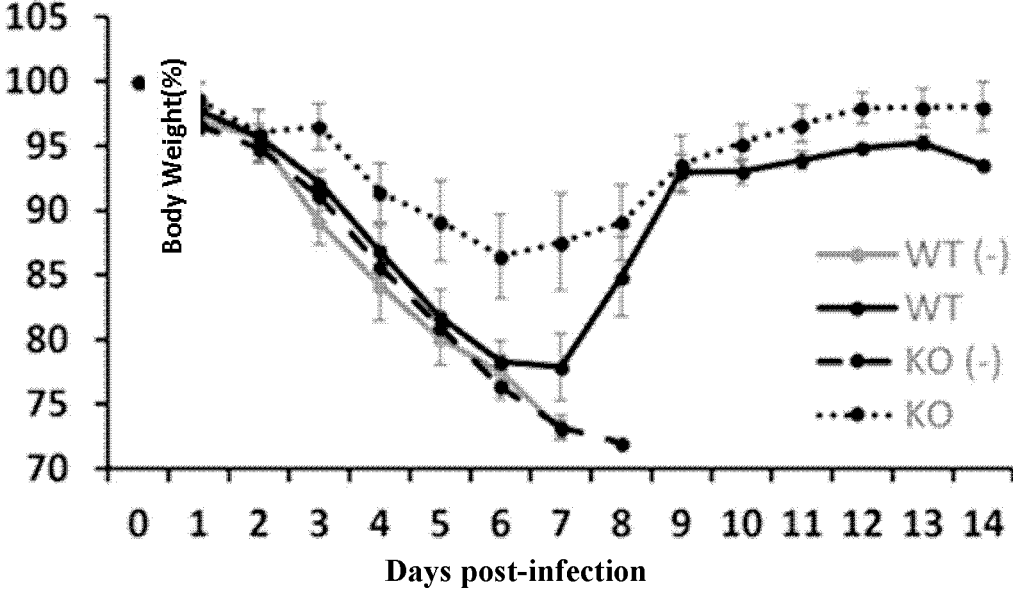

To determine the protective effect of NAGT mutant against heterosubtypic infection, a mouse-adapted A/HK/1/68 H3N2 (HK68; 10 10 $MLD_{50}$) virus was used in the virus challenge. All vaccinated KO mice survived, whereas 38% of vaccinated WT mice and all unvaccinated mice died from the infection (FIG. 15A). In addition, vaccinated KO mice had less weight loss (FIG. 15B) and faster virus clearance in lung (FIG. 15C) than the controls. Robust H3N2 virus-specific neutralizing antibody and NP-specific antibody responses could be detected in vaccinated KO mice, but not in vaccinated WT mice, at day 7 post-challenge (FIG. 15D and Table 8). Furthermore, surviving vaccinated WT mice had much less NP-specific antibody than those of vaccinated KO mice at day 14 post-challenge. These results show that the NAGT mutant can mount potent heterosubtypic antibody responses in KO mice against H3N2 virus. Such enhanced heterosubtypic protection was confirmed to require the presence of anti-α-Gal antibody in KO mice (see Example 4 below).

Figure 16A:
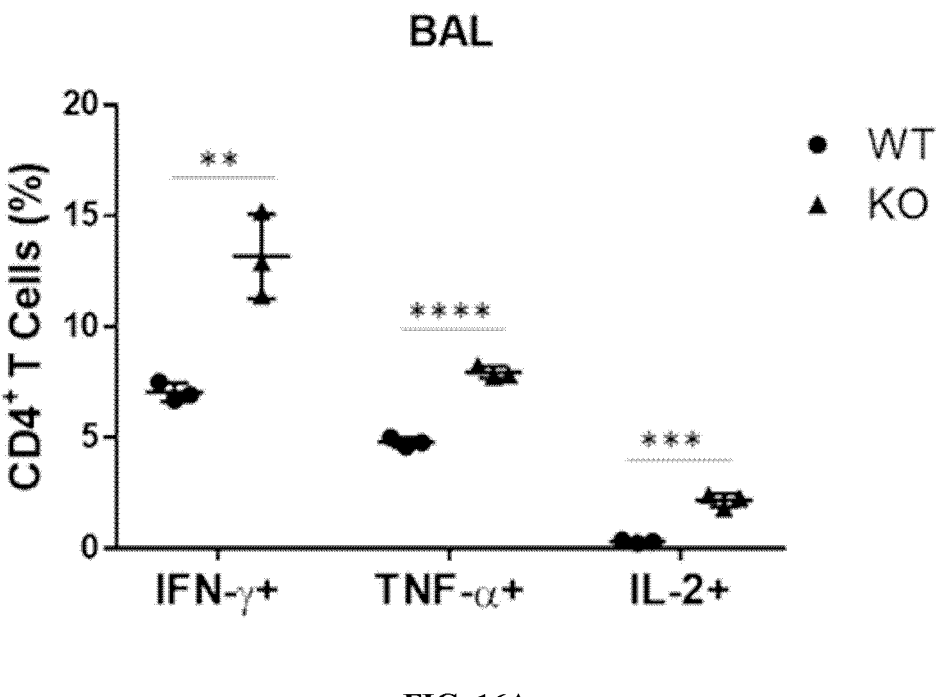
FIGS. 16A-16B are graphs showing HK68-specific CD4+ (FIG. 16A) and CD8$^+$ (FIG. 16B) T-cell recall responses in BAL of infected mice at day 7 post-infection. Data represent Mean±SD; : p<0.01, *: p<0.001, ****: p<0.0001.
Figure 16B:
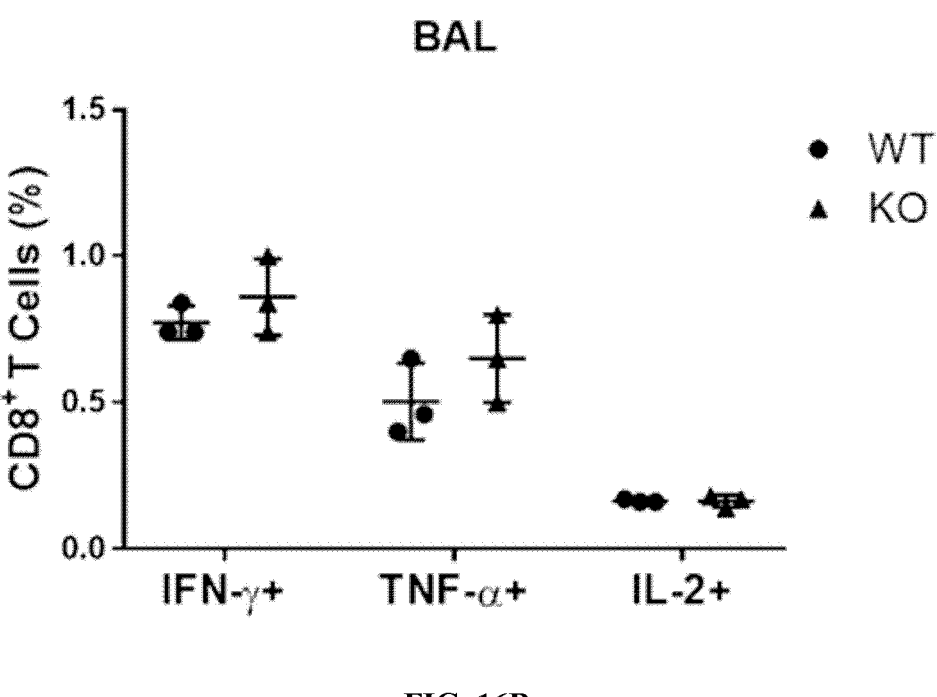
Figure 17A:
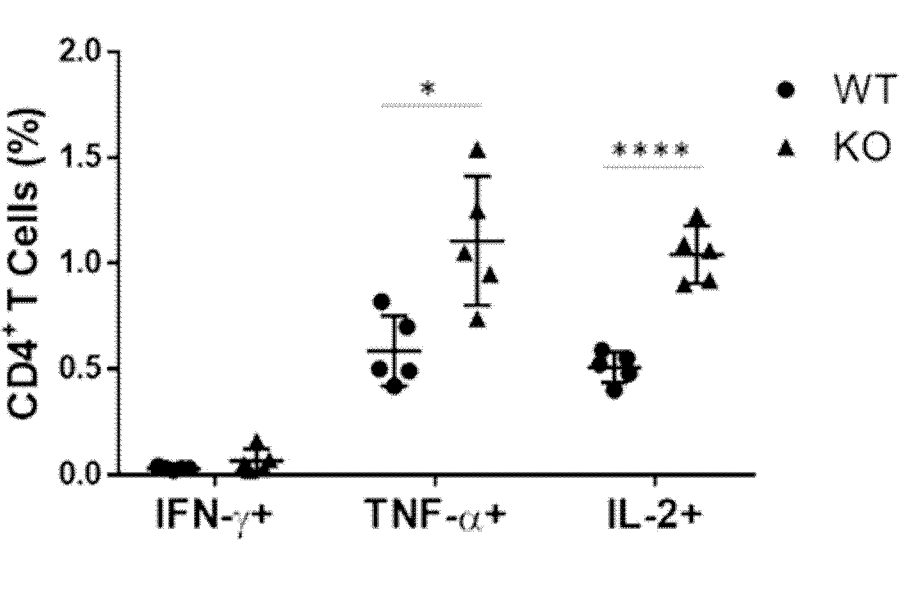
FIGS. 17A-17B are graphs showing HK68-specific CD4+ (FIG. 17A) and CD8$^+$ (FIG. 17B) T-cell recall responses in spleen of infected mice at day 7 post-infection. Dotted line for comparison between KO and WT mice at the same time point (t-test). Data represent Mean±SD; *: p<0.05, ****: p<0.0001.
Figure 17B:
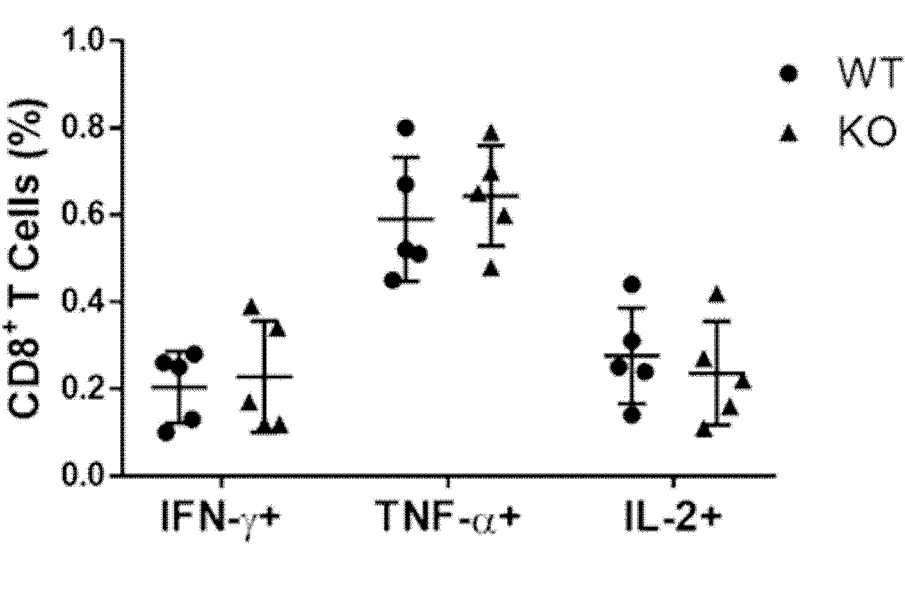

To determine the mechanism of protection in vaccinated KO mice, CD4⁺ and CD8⁺ T-cell responses in vaccinated WT and KO mice at day 7 post-challenge were studied. H3N2 influenza virus-specific CD4⁺ T-cell responses were found to be much stronger in the lung and spleen tissues of vaccinated KO mice than those of vaccinated WT mice (FIG. 16A and FIG. 17A). By contrast, no difference was detected between the CD8⁺ T-cell responses of these two vaccinated groups (FIG. 16B and FIG. 17B).

The DC, neutrophil and macrophage populations in infected lung and spleen tissues were studied. Lung tissues from both vaccinated groups had increased frequencies of DCs after challenge (FIG. 18A) and these were predominantly $CD11b^{hi}$ DC responses (FIG. 18B and FIG. 18C). Interestingly, although the $CD11b^{hi}$ DCs levels between vaccinated WT and KO mice were similar, the $CD11b^{lo/-}$ DCs level of vaccinated KO mouse group was significantly higher than that of vaccinated WT group at day 7 post-challenge (FIG. 18B and FIG. 18C). In spleen, a significant increase of DC population after challenge could not be observed in all vaccinated groups. The neutrophil or macrophage profiles in infected WT and KO mice were also similar.

TABLE 8

NP-specific antibody titres in mice at days 0, 7, and 14 after virus challenge[a].

| Mouse | Vaccination | Days Post-infection | Endpoint titer against NP |
|---|---|---|---|
| WT | – | 0 | <40 |
| | + | 0 | <40 |
| | + | 7 | <40 |
| | + | 14 | 320 |
| KO | – | 0 | <40 |
| | + | 0 | <40 |
| | + | 7 | 320 |
| | + | 14 | 1280 |

[a]antibody levels were studies by ELISA assays.

Figure 19A:
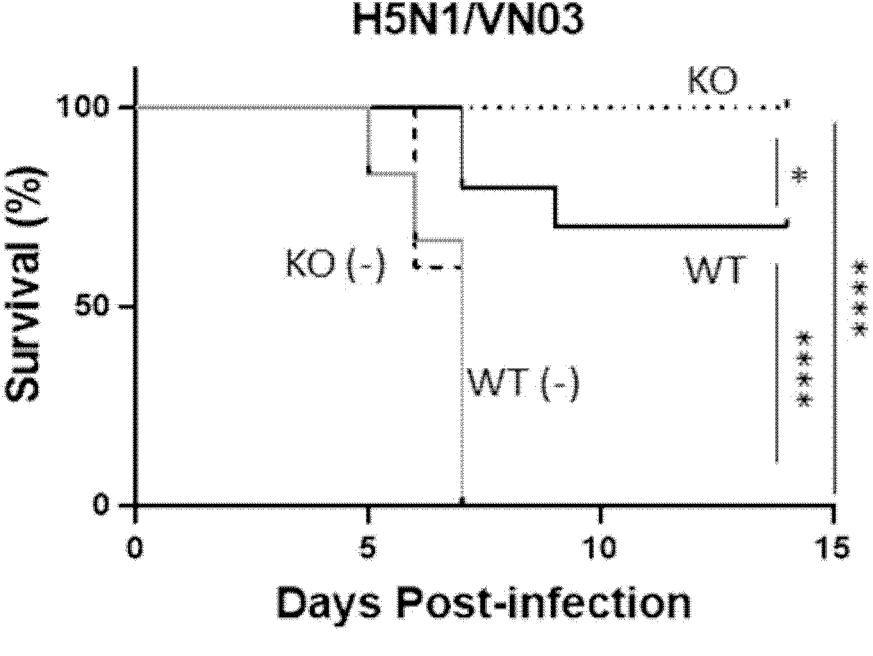
FIGS. 19A-19C are graphs showing protection of mice by NAGT mutant against a lethal heterosubtypic H5N1 challenge. Vaccinated and unvaccinated (–) mice were challenged with a lethal dose of H5N1 virus (VN1203; 10 $MLD_{50}$) at 3 weeks post-vaccination.
Figure 19B:
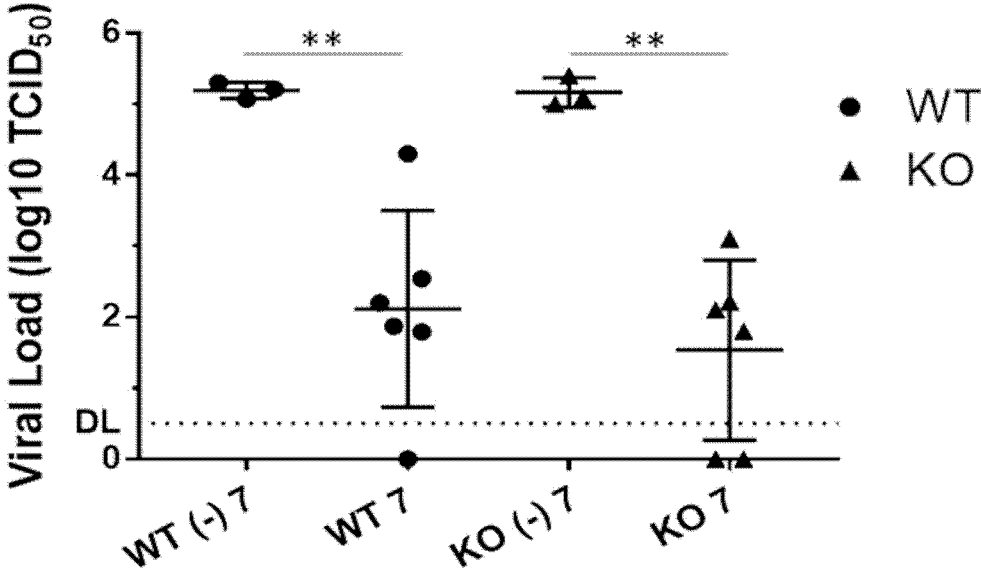
Figure 19C:
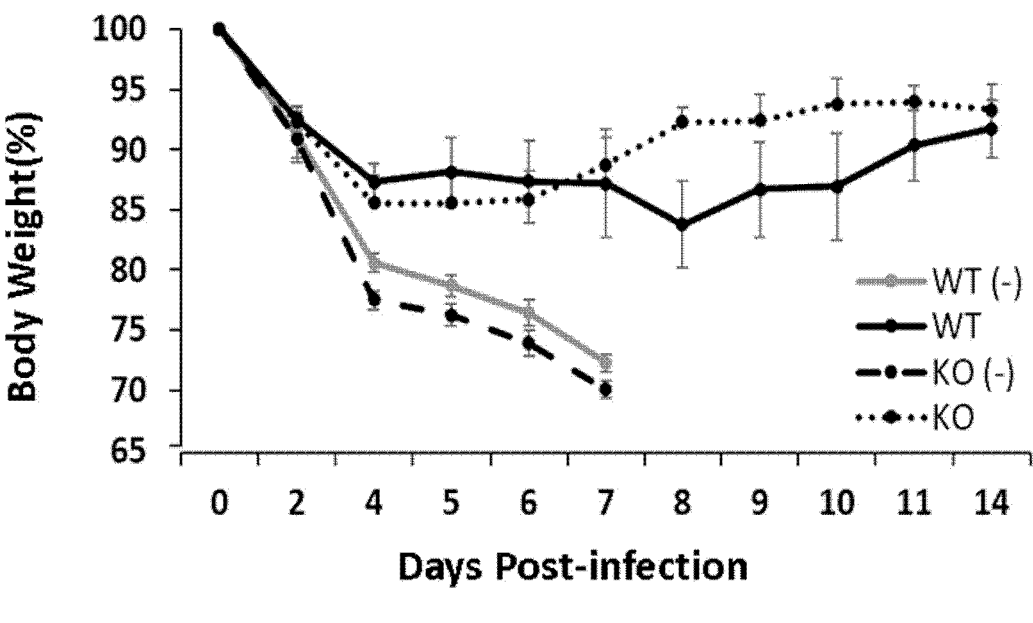

NAGT Mutant can Protect Mice Against a Lethal Highly Pathogenic H5N1 Virus Challenge The protective effect of NAGT mutant against highly pathogenic H5N1 avian influenza virus infection was studied in the mouse model (A/VN/1203/04; 10 $MLD_{50}$). All vaccinated KO mice survived from a lethal virus challenge (FIG. 19A), whereas vaccinated WT mice had a significantly reduced survival rate (70%; p<0.05). The lung virus titres between these two vaccinated groups at day 7 post-challenge was not significantly different (FIG. 19B). However, a more rapid recovery was observed in the vaccinated KO group in week 2 post-challenge (FIG. 19C).

Thus, these results, together with those from the above H3N2 studies, show that the NAGT mutant can elicit strong broadly cross-reactive immune responses against both Group 1 (H1 and H5) and Group 2 (H3) influenza virus infections.

With only a single intranasal vaccination, vaccinated KO mice could develop enhanced humoral and/or cell-mediated responses after virus challenge. The vaccinated mice did not have detectable pre-existing neutralizing antibody against H3N2 virus before challenge. Results from the H3 virus challenge model demonstrate that the vaccinated KO mice could develop prompt and robust antibody responses against both viral surface and internal proteins after the challenge (FIG. 15D and Table 8). These results demonstrate that NAGT-primed KO mice have effective cross-reactive memory responses to heterosubtypic influenza viruses, thereby activating an early humoral response to control the infection. With the enhanced T-cell responses observed in the mouse models, it is likely that the enhanced protection involves interactions between both T and B cell compartments.

Figure 21A:
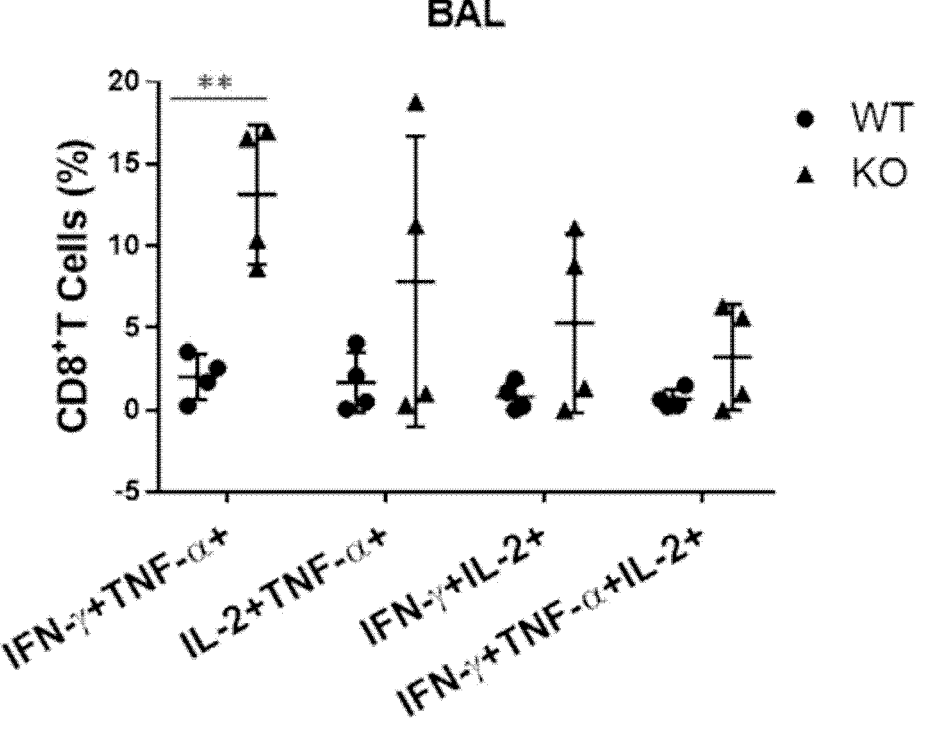
FIGS. 21A-21B are graphs showing enhanced polyfunctional T cell responses by NAGT mutant vaccination in BAL upon virus challenge.
Figure 21B:
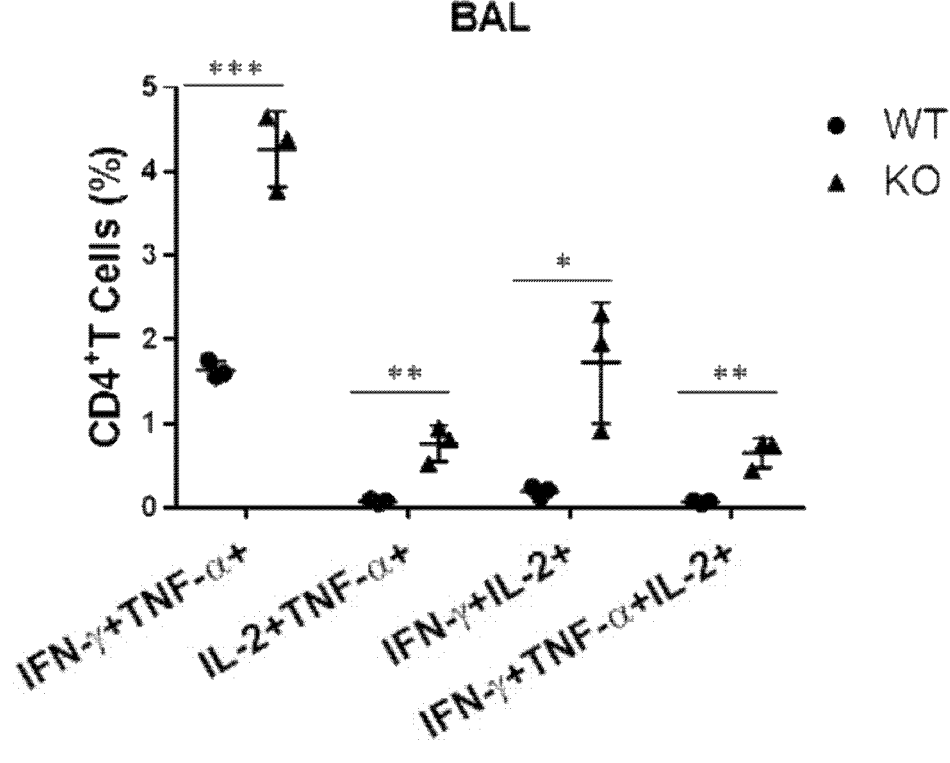

In vaccinated KO mice, a homologous challenge could trigger robust CD8⁺ T-cell recall responses (FIG. 13A and FIG. 13B), whereas a heterosubtypic challenge could induce robust CD4+ T-cell recall responses (FIG. 16A and FIG. 16B). Many T cells in the BAL of these mice are polyfunctional cytokine producing T cells (FIG. 21A and FIG. 21B), demonstrating that vaccinated KO mice had better T-cell responses than vaccinated WT mice to control virus infection. These differential CD4⁺ and CD8⁺ responses in vaccinated KO mice also shows that the protective mechanisms of NAGT mutant in the studied H1 and H3 models are different. Specifically, there were enhanced CD4⁺ T-cell recall responses in the BAL and spleen samples of vaccinated KO mice after a H3 virus challenge. Memory CD4⁺ T cells are crucial for heterosubtypic influenza protection (Valkenburg, et al., *PNAS*, 111:5676-81 (2014); Richards, et al., *J. Virol.*, 83:6566-77 (2009)). Depleting memory CD4⁺ T cells in mice vaccinated with a vaccinia-vectored universal influenza vaccine can increase mortality, delay antibody production and reduce CD8⁺ T-cell recall response after a heterosubtypic challenge (Valkenburg, et al., *Vaccine*, 36:4198-4206 (2018)). The results from the H3 model demonstrate these findings.

Figure 15C:
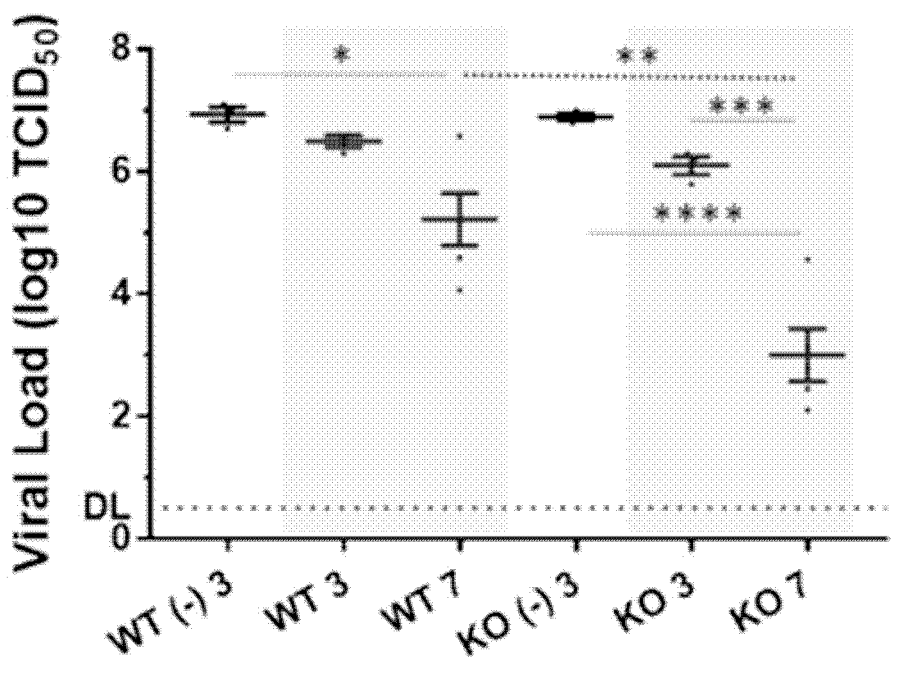
Figure 15D:
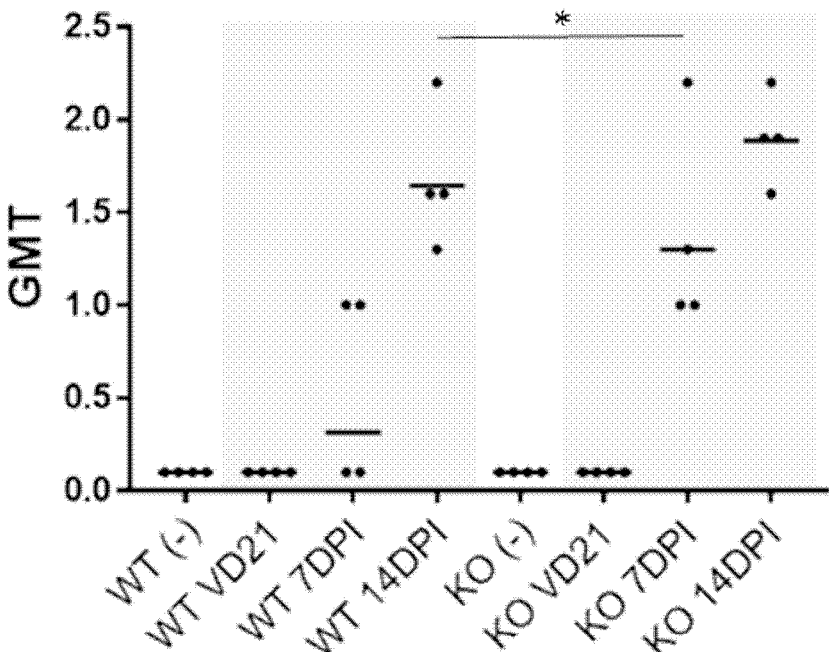

An increased CD1 $b^{lo/-}$ DC frequency was observed in vaccinated KO mice after a heterosubtypic challenge (FIG. 15C). The gating strategy for DCs also shows that these were classical DCs (cDCs). Non-lymphoid cDCs have two major subsets: CD103⁺ CD11b⁻ and CD103-CD11b⁺ cDCs. Hence, the $CD11b^{lo/-}$ DCs in this study were considered as CD103⁺ cDCs (Condon, et al., *J. Leukoc. Biol.*, 90:883-95 (2011); Desch, et al., *Immunologic Research*, 55:178-186 (2013); Heath and Carbone, *Nat. Immunol.*, 10:1237 (2009); Merad, et al., *Annual Rev. Immunol.*, 31:563-604 (2013)). CD1 $1b^{hi}$ and $CD11b^{lo/-}$ cDCs have distinct functions. Briefly, lung $CD11b^{hi}$ cDCs are potent inducers of Th2 and Th17 responses against extracellular pathogens (Mesnil, et al., *PLoS One*, 7:e53242 (2012); Plantinga, et al., *Immunity*, 38:322-335 (2013)) and CD103⁺ cDCs favour Th1 responses by priming CD4⁺ T cells, and cross-presenting soluble and apoptosis cells-associated antigens to CD8⁺ T cells via MHC I receptors (Desch, et al., *J. Exp. Med.*, 208:1789-1797 (2011); Furuhashi, et al., *Am. J. Respir. Cell Mol. Biol.*, 46:165-72 (2012)). In addition, CD11b[lo/−] cDCs are known to play critical roles for influenza virus clearance (GeurtsvanKessel, et al., *J. Exp. Med.*, 205:1621-34 (2008)). This cell population acquires influenza antigens through phagocytosis of infected cells, but not by infection, and it can facilitate the lung homing capacity of differentiated T cells to lymph nodes (GeurtsvanKessel, et al., *J. Exp. Med.*, 205:1621-34 (2008); Kim, et al., *Immunity*, 40:400-13 (2014); Helft, et al., *J. Clin. Invest.*, 122:4037-47 (2012)). The ability of NAGT to enhance CD11b[lo/−] cDCs responses may therefore be beneficial against influenza virus infection. Further characterization of this CD11b[lo/−] cDC population may help to explain the NAGT mutant-induced heterosubtypic protection.

Example 4. The Enhanced Heterosubtypic Protection Involves Anti-α-Gal Antibody in KO Mice Material and Methods To demonstrate the above enhanced vaccine-induced protective effect in KO mice was due to the recognition of α-Gal epitopes by anti-α-Gal antibody, KO mice with or without prior rabbit RBC injections were vaccinated and challenged using the protocol identical to the one used in the above H3 model.

Results

Figure 20A:
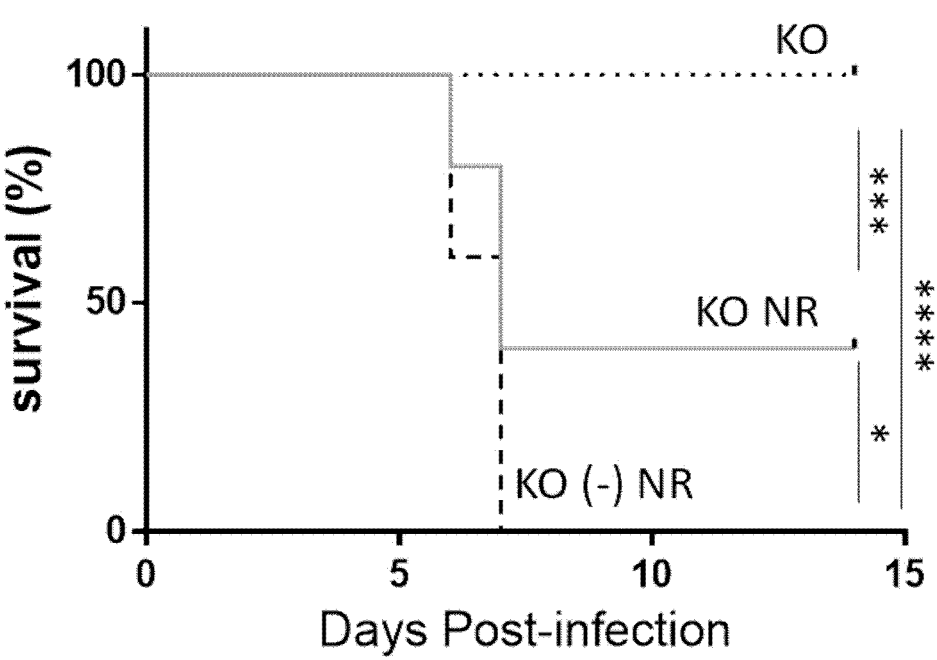
FIGS. 20A-20B are graphs showing enhanced protection by NAGT mutant requires anti-α-Gal antibody in mice.
Figure 20B:
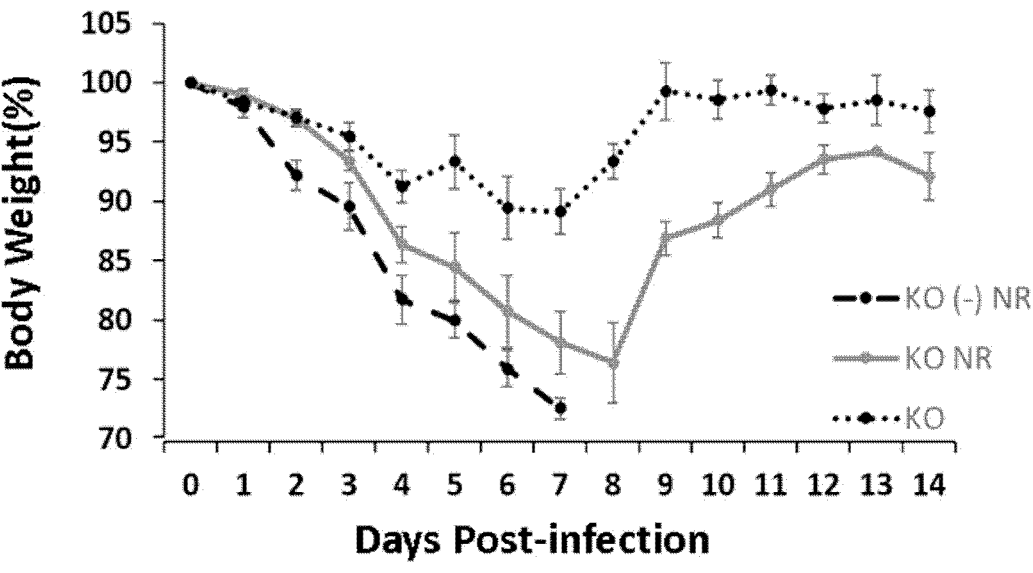

Mice without the RBC treatment did not have detectable levels of anti-α-Gal antibody before vaccination and virus challenge (Table 9). In the absence of anti-α-Gal antibody in vivo, the enhanced heterosubtypic protective effects of NAGT mutant disappeared (FIG. 20A, Group KO NR). The survival rate of this vaccinated group (40%) was similar to the one observed in vaccinated WT mice (38%) (FIG. 15A). Besides, this group of mice had more severe weight loss than the fully protected group (FIG. 20B). These results demonstrate that, without prior rabbit RBC injections, the α-1,3-GT KO and WT mice have similar susceptibilities to influenza virus infection. These results also confirm that the enhanced protective effect of NAGT mutant depends on the presence of anti-α-Gal antibody in vivo.

cells can obviate the above-mentioned enzymatic labelling and its downstream purification steps. Secondly, the administration of NAGT mutant via respiratory route can induce mucosal immune responses. Thirdly, the extent of NAGT virus replication in humans in vivo can be safely controlled by the naturally expressed anti-α-Gal antibody. Fourthly, infected cells labelled by anti-α-Gal antibody can trigger antibody-mediated cellular immune responses. Finally, multiple viral antigens expressed by infected cells can be more readily to be taken up by professional APCs for antigen presentation, thereby enhancing downstream vaccine-induced responses against a wide spectrum of viral proteins.

LIST OF ADDITIONAL REFERENCES

Wu, et al., *Clin. Infect. Dis.*, 51:1184-91 (2010).
Tam, et al., *Paediatr. Child Health*, 23:31-34 (2018).
Misharin, et al., *Am. J. Respir. Cell Mol. Biol.*, 49:503-10 (2013).

It is understood that the disclosed method and compositions are not limited to the particular methodology, protocols, and reagents described as these can vary. It is also to be understood that the terminology used herein is for the purpose of describing particular embodiments only, and is not intended to limit the scope of the present invention which will be limited only by the appended claims.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a virus is disclosed and discussed and a number of modifications that can be made to a number of viruses including the virus are discussed, each and every combination and permutation of virus and the modifications that are possible are specifically contemplated unless specifically indicated to the contrary. Thus, if a class of molecules A, B,

TABLE 9

Anti-α-Gal antibody titres in mice immediate before vaccination and virus challenge[a].

| Group | Mouse | Rabbit RBC injections | Vaccination | Anti-α-Gal antibody titre before vaccination (Age: 8 weeks) | Anti-α-Gal antibody titre before challenge (Age: 11 weeks) |
|---|---|---|---|---|---|
| KO (−) NR[c] | KO | − | − | <10 | <10 |
| KO NR[b] | KO | − | + | <10 | <10 |
| KO[b] | KO | + | + | 160 | 160 |

[a]Serum anti-α-Gal antibody titres of these mouse groups were determined by ELISA.
[b]KO mice with (KO) or without (KO NR) rabbit RBC stimulations were vaccinated at 8 weeks of age.
[c]mock treated KO mice (KO(−)NR) were used as controls.

An attenuated influenza virus that contains a α-1,3-GT gene in order to express α-Gal epitopes in infected cells was generated. The expression of viral RNA and viral proteins in infected cells upon vaccination can further enhance vaccine-induced immune responses. The results demonstrate that this approach is a promising vaccine strategy to induce heterosubtypic protection against influenza.

The use of NAGT mutant as a LAIV has several advantages over in vitro enzymatic labelling of antigens with α-Gal epitopes for making experimental inactivated vaccines. Firstly, the expression of α-Gal epitopes by infected and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. Further, each of the materials, compositions, components, etc. contemplated and disclosed as above can also be specifically and independently included or excluded from any group, subgroup, list, set, etc. of such materials. These concepts apply to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

It must be noted that as used herein and in the appended claims, the singular forms "a," "an," and "the" include plural reference unless the context clearly dictates otherwise. Thus, for example, reference to "a virus" includes a plurality of such viruses, reference to "the virus" is a reference to one or more viruses and equivalents thereof known to those skilled in the art, and so forth.

Throughout the description and claims of this specification, the word "comprise" and variations of the word, such as "comprising" and "comprises," means "including but not limited to," and is not intended to exclude, for example, other additives, components, integers or steps.

"Optional" or "optionally" means that the subsequently described event, circumstance, or material may or may not occur or be present, and that the description includes instances where the event, circumstance, or material occurs or is present and instances where it does not occur or is not present.

Unless the context clearly indicates otherwise, use of the word "can" indicates an option or capability of the object or condition referred to. Generally, use of "can" in this way is meant to positively state the option or capability while also leaving open that the option or capability could be absent in other forms or embodiments of the object or condition referred to. Unless the context clearly indicates otherwise, use of the word "may" indicates an option or capability of the object or condition referred to. Generally, use of "may" in this way is meant to positively state the option or capability while also leaving open that the option or capability could be absent in other forms or embodiments of the object or condition referred to. Unless the context clearly indicates otherwise, use of "may" herein does not refer to an unknown or doubtful feature of an object or condition.

Ranges can be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. It should be understood that all of the individual values and sub-ranges of values contained within an explicitly disclosed range are also specifically contemplated and should be considered disclosed unless the context specifically indicates otherwise. Finally, it should be understood that all ranges refer both to the recited range as a range and as a collection of individual numbers from and including the first endpoint to and including the second endpoint. In the latter case, it should be understood that any of the individual numbers can be selected as one form of the quantity, value, or feature to which the range refers. In this way, a range describes a set of numbers or values from and including the first endpoint to and including the second endpoint from which a single member of the set (i.e. a single number) can be selected as the quantity, value, or feature to which the range refers. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Although the description of materials, compositions, components, steps, techniques, etc. can include numerous options and alternatives, this should not be construed as, and is not an admission that, such options and alternatives are equivalent to each other or, in particular, are obvious alternatives. Thus, for example, a list of different viruses does not indicate that the listed viruses are obvious one to the other, nor is it an admission of equivalence or obviousness.

Every virus disclosed herein is intended to be and should be considered to be specifically disclosed herein. Further, every subgroup that can be identified within this disclosure is intended to be and should be considered to be specifically disclosed herein. As a result, it is specifically contemplated that any virus, or subgroup of the virus can be either specifically included for or excluded from use or included in or excluded from a list of viruses.

Those skilled in the art will recognize, or be able to ascertain using no more than routine experimentation, many equivalents to the specific embodiments of the method and compositions described herein. Such equivalents are intended to be encompassed by the following claims.

The invention claimed is:

1. An attenuated live influenza virus comprising a heterologous nucleic acid encoding α-1,3-galactosyltransferase (α-1,3-GT), wherein, upon infecting a host cell the attenuated live influenza virus expresses α-1,3-GT, wherein the expressed α-1,3-GT synthesizes α-1,3-galactose in the host cell, and wherein the α-1,3-galactose is exposed on the surface of the host cell.

2. The attenuated live influenza virus of claim 1, wherein the heterologous nucleic acid encoding α-1,3-GT is fused to a nucleic acid encoding at least one viral protein expressed by the attenuated live influenza virus.

3. The attenuated live influenza virus of claim 2, wherein the heterologous nucleic acid encoding $\alpha$-1,3-GT is fused to the nucleic acid encoding the viral protein expressed by the attenuated live influenza virus via one or more linkers.

4. The attenuated live influenza virus of claim 3, wherein the one or more linkers are peptide linkers.

5. The attenuated live influenza virus of claim 2, further comprising a nucleic acid encoding a 2A self-cleaving peptide between the heterologous nucleic acid encoding $\alpha$-1,3-GT and the nucleic acid encoding the viral protein.

6. The attenuated live influenza virus of claim 5, wherein the nucleic acid encoding the 2A self-cleaving peptide comprises a protease cleavage site.

7. The attenuated live influenza virus of claim 5, wherein the 2A self-cleaving peptide is derived from porcine teschovirus-1.

8. The attenuated live influenza virus of claim 5, wherein the 2A self-cleaving peptide is flanked by short peptide linkers.

9. The attenuated live influenza virus of claim 8, wherein the short peptides linkers are GSG.

10. The attenuated live influenza virus of claim 2, wherein the viral protein is neuraminidase (NA).

11. The virus of claim 1, wherein the nucleic acid encoding $\alpha$-1,3-GT is incorporated into the genome of the attenuated live influenza virus.

12. The attenuated live influenza virus of claim 1, wherein the heterologous nucleic acid encoding $\alpha$-1,3-GT is a mammalian nucleic acid encoding $\alpha$-1,3-GT.

13. The attenuated live influenza virus of claim 1, wherein the heterologous nucleic acid encoding $\alpha$-1,3-GT is a mouse nucleic acid encoding $\alpha$-1,3-GT.

14. The attenuated live influenza virus of claim 1, wherein the virus is attenuated by serial passage in cultured cells, serial passage in a heterologous host animal, gene deletion in the virus, site-directed mutagenesis of the virus, altering codon usage of the virus, selection of cold-adapted mutants, using a related virus from a heterologous host species, using a naturally occurring attenuated virus strain, or combinations thereof.

15. The virus of claim 14, wherein the virus is attenuated by serial passage in cultured cells, wherein the cultured cells are Madin-Darby Canine Kidney (MDCK) cells.

16. A vaccine comprising the virus of claim 1.

17. A method of vaccination, the method comprising administering to a subject in need thereof a vaccine of claim 16.

18. The method of claim 17, wherein the vaccine is administered intranasally, pulmonarily, orally, subcutaneously, intramuscularly, intradermally, or intraperitoneally.

19. A vaccine comprising one or more viral proteins expressed by the virus of claim 1, wherein the one or more viral proteins comprise $\alpha$-1,3-galactose.

20. A method of making the vaccine of claim 19, the method comprising infecting a cell with the virus, whereby the one or more viral proteins comprising $\alpha$-1,3-galactose are produced.

21. The method of claim 20 further comprising purifying the one or more viral proteins.

* * * * *